(12) United States Patent
Pestell

(10) Patent No.: US 9,453,836 B2
(45) Date of Patent: Sep. 27, 2016

(54) USE OF MODULATORS OF CCR5 IN THE TREATMENT OF CANCER AND CANCER METASTASIS

(71) Applicant: Richard G. Pestell, Philadelphia, PA (US)

(72) Inventor: Richard G. Pestell, Philadelphia, PA (US)

( * ) Notice: Subject to any disclaimer, the term of this patent is extended or adjusted under 35 U.S.C. 154(b) by 0 days.

(21) Appl. No.: 13/893,791

(22) Filed: May 14, 2013

(65) Prior Publication Data
US 2013/0303512 A1  Nov. 14, 2013

Related U.S. Application Data

(60) Provisional application No. 61/646,586, filed on May 14, 2012, provisional application No. 61/646,593, filed on May 14, 2012.

(51) Int. Cl.
| | |
|---|---|
| *A61K 31/506* | (2006.01) |
| *A61K 31/46* | (2006.01) |
| *G01N 33/50* | (2006.01) |
| *G01N 33/574* | (2006.01) |

(52) U.S. Cl.
CPC .......... *G01N 33/5091* (2013.01); *A61K 31/46* (2013.01); *A61K 31/506* (2013.01); *G01N 33/57415* (2013.01); *G01N 33/57492* (2013.01); *G01N 2333/7158* (2013.01); *G01N 2800/56* (2013.01)

(58) Field of Classification Search
CPC .................. A61K 2300/00; A61K 39/39558; A61K 39/0011; A61K 31/519; A61K 38/177; A61K 38/1774; C07K 2317/34
See application file for complete search history.

(56) References Cited

U.S. PATENT DOCUMENTS

| | | | |
|---|---|---|---|
| 5,587,458 A | 12/1996 | King et al. | |
| 5,877,305 A | 3/1999 | Huston et al. | |
| 6,586,430 B1 | 7/2003 | Armour et al. | |
| 6,596,746 B1 | 7/2003 | Das et al. | |
| 6,667,314 B2 | 12/2003 | Perros et al. | |
| 6,689,765 B2 | 2/2004 | Baroudy et al. | |
| 7,384,944 B2 | 6/2008 | Baroudy | |
| 7,872,027 B2 | 1/2011 | Metallo et al. | |
| 2002/0048786 A1 | 4/2002 | Rosen et al. | |
| 2002/0182624 A1 | 12/2002 | Zlotnik | |
| 2004/0151719 A1 | 8/2004 | Li et al. | |
| 2006/0251651 A1 | 11/2006 | Shibayama et al. | |
| 2007/0270429 A1 | 11/2007 | Shibayama et al. | |
| 2009/0118175 A1* | 5/2009 | Macina ................ | C12Q 1/6886 514/1.1 |
| 2009/0131403 A1 | 5/2009 | Kusuda et al. | |
| 2010/0184046 A1 | 7/2010 | Klass et al. | |

FOREIGN PATENT DOCUMENTS

| | | |
|---|---|---|
| WO | 9519970 A1 | 7/1995 |
| WO | 9610028 A1 | 4/1996 |
| WO | 9713760 A1 | 4/1997 |
| WO | 9716452 A1 | 5/1997 |
| WO | 9728161 A1 | 8/1997 |
| WO | 9732879 A1 | 9/1997 |
| WO | 9749706 A1 | 12/1997 |
| WO | 9802434 A1 | 1/1998 |
| WO | 9802437 A1 | 1/1998 |
| WO | 9935132 A1 | 7/1999 |
| WO | 9935146 A1 | 7/1999 |
| WO | 0062778 A1 | 10/2000 |
| WO | 02/081449 A1 | 10/2002 |
| WO | 2006067584 A1 | 6/2006 |
| WO | 2012122499 A2 | 9/2012 |

OTHER PUBLICATIONS

Zhang et al (Oncology Report, 2009, 21:1113-1121).*
Robinson et al (Cancer Research, 63:8360-8365).*
Muller et al (Nature, 2001, 410:50-56).*
Walser et al (Cancer Research, 2006, 66:7701-7707).*
Wu et al (Current Pharmaceutical Design, 2009, 15:742-757).*
Kim et al (Human Pathology, 2006, 37:1217-1226).*
Tan et al (Journal of Immunology, 2009, 182:1746-1755).*
Karnoub et al. (Nature, 2007, 449:557-565).*
Rakha et al. (Journal of Clinical Oncology, 2008, 26:2568-2581).*
Potter, et al. "Systemic chemokine Levels in Breast Cancer Patients and their Relationship with Circulating Menstrual Hormones," Breast Cancer Res Treat 115, 2009, pp. 279-287.
Irizarry, R.A., et al., Summaries of Affymetrix GeneChip probe level data. Nucleic Acids Res, 2003. 31(4): p. e15.
Huang, E., et al., Gene expression phenotypic models that predict the activity of oncogenic pathways. Nat Genet, 2003. 34(2): p. 226-230.
Dai, M., et al., Evolving gene/transcript definitions significantly alter the interpretation of GeneChip data. Nucleic Acids Res, 2005. 33(20): p. e175.
Chen, R., L. Li, and Butte, A.J., Ailun: reannotating gene expression data automatically. Nat Methods, 2007. 4 (11): p. 879.
Parkin, DM, Fernandez, LM. Use of statistics to assess the global burden of breast cancer. Breast J 2006; 12 Suppl 1: S70-80.
Group EBCTC. Effects of chemotherapy and hormonal therapy for early breast cancer on recurrence and 15-year survival: an overview of the randomised trials. Lancet 2005; 365: 1687-717.

(Continued)

*Primary Examiner* — Julie Wu
(74) *Attorney, Agent, or Firm* — Pepper Hamilton LLP

(57) ABSTRACT

This disclosure is directed, in part, to a method of determining whether a subject having cancer is at risk for developing metastasis of the cancer. In one embodiment, the method comprises (a) obtaining a biological sample from the subject having cancer; (b) determining CCR5 expression level and/or expression level of at least one of CCR5 ligands in the biological sample; and (c) if the expression level of CCR5 and/or of at least one of CCR5 ligands determined in step (b) is increased compared to CCR5 expression level and/or expression level of at least one of CCR5 ligands in a control sample, then the subject is identified as likely at risk for developing metastasis of the cancer.

14 Claims, 31 Drawing Sheets

(56) References Cited

OTHER PUBLICATIONS

Meyers, M.O., et al. Impact of breast cancer molecular subtypes on locoregional recurrence in patients treated with neoadjuvant chemotherapy for locally advanced breast cancer. Ann Surg Oncol 2011; 18: 2851-7.
Kennecke, H., et al. Metastatic behavior of breast cancer subtypes. J Clin Oncol 2010; 28: 3271-7.
Perou, C.M., et al. Molecular portraits of human breast tumours. Nature 2000; 406: 747-52.
Reis-Filho, J.S., Lakhani, S.R., Breast cancer special types: why bother? J Pathol 2008; 216: 394-8.
Kakinuma, T., Hwang, S.T., Chemokines, chemokine receptors, and cancer metastasis. J Leukoc Biol 2006; 79: 639-51.
Muller, A., et al. Involvement of chemokine receptors in breast cancer metastasis. Nature 2001; 410: 50-6.
Luboshits, G., et al. Elevated expression of the CC chemokine regulated on activation, normal T cell expressed and secreted (RANTES) in advanced breast carcinoma. Cancer Res 1999; 59: 4681-7.
Niwa, Y., et al. Correlation of tissue and plasma RANTES levels with disease course in patients with breast or cervical cancer. Clin Cancer Res 2001; 7: 285-9.
Zhang, Y., et al. Role of CCL5 in invasion, proliferation and proportion of CD44+/CD24< phenotype of MCF-7 cells and correlation of CCL5 and CCR5 expression with breast cancer progression. Oncol Rep 2009; 21: 1113-21. Medline.
Jilao, X., et al. c-Jun induces mammary epithelial cellular invasion and breast cancer stem cell expansion. J Biol Chem 2010; 285: 8218-26.
Karnoub, A.E., et al. Mesenchymal stem cells within tumour stroma promote breast cancer metastasis. Nature 2007; 449: 557-63.
Locati, M., et al. Analysis of the gene expression profile activated by the CC chemokine ligand 5/RANTES and by lipopolysaccharide in human monocytes. J Immunol 2002; 168: 3557-62.
Robinson, S.C., et al., Chemokine stimulation of monocyte matrix metalloproteinase-9 requires endogenous TNF-alpha. Eur J Immunol 2002; 32: 404-12.
Robinson, S.C., et al., A chemokine receptor antagonist inhibits experimental breast tumor growth. Cancer Res 2003; 63: 8360-5.
Manes, S., et al. CCR5 expression influences the progression of human breast cancer in a p53-dependent manner. J Exp Med 2003; 198: 1381-9.
Murooka, T.T., et al. CCL5 promotes proliferation of MCF-7 cells through mTOR-dependent mRNA translation. Biochem Biophys Res Commun 2009; 387: 381-6.
Stormes, K.A., et al. Inhibition of metastasis by inhibition of tumor-derived CCL5. Breast Cancer Res Treat 2005; 89:209-12.
Jayasinghe, M.M., et al., Tumor-derived CCL5 does not contribute to breast cancer progression. Breast Cancer Res Treat 2008; 111: 511-21.
Ertel, A., et al. RB-pathway disruption in breast cancer: differential association with disease subtypes, disease-specific prognosis and therapeutic response. Cell Cycle 2010; 9: 4153-63.
Wilkin, T.J., et al. Three-year safety and efficacy of vicriviroc, a CCR5 antagonist, in HIV-1-infected treatment-experienced patients. J Acquir Immune Defic Syndr 2010; 54: 470-6.
Barrett, T., et al. NCBI GEO: mining tens of millions of expression profiles-database and tools update. Nucleic Acids Res 2007; 35: D760-5.
Brazma, A., et al. ArrayExpress—a public repository for microarray gene expression data at the EBI. Nucleic Acids Res 2003; 31: 68-71.
Hu, Z., et al. The molecular portraits of breast tumors are conserved across microarray platforms. BMC Genomics 2006; 7: 96.
Nguyen, D.H.,et al., Cholesterol is essential for macrophage inflammatory protein 1 beta binding and conformational integrity of CC chemokine receptor 5. Blood 2002; 99: 4298-306.
Janowski, E., et al. c-Jun is required for TGF-beta-mediated cellular migration via nuclear Ca(2) signaling. Int J Biochem Cell Biol 2011; 43: 1104-13.

Velasco-Velazquez, M.A., et al. 4-Hydroxycoumarin disorganizes the actin cytoskeleton in B16-F10 melanoma cells but not in B82 fibroblasts, decreasing their adhesion to extracellular matrix proteins and motility. Cancer Lett 2003; 198: 179-86.
Liu, H., et al. Cancer stem cells from human breast tumors are involved in spontaneous metastases in orthotopic mouse models. Proc Natl Acad Sci USA 2010; 107: 18115-20.
Zahler, M.H., et al. The application of a lentiviral vector for gene transfer in fetal human hepatocytes. J Gene Med 2000; 2: 186-93.
Walker, D.K., et al., Species differences in the disposition of the CCR5 antagonist, UK-427,857, a new potential treatment for HIV. Drug Metab Dispos 2005; 33: 587-95.
Wu, K., et al. Dachshund inhibits oncogene-induced breast cancer cellular migration and invasion through suppression of interleukin-8. Proc Natl Acad Sci USA 2008; 105: 6924-9.
Charafe-Jauffret, E., et al. Gene expression profiling of breast cell lines identifies potential new basal markers. Oncogene 2006; 25: 2273-84.
Riaz, M., et al., Low-risk susceptibility alleles in 40 human breast cancer cell lines. BMC Cancer 2009; 9: 236.
Hollestelle, A., et al. Distinct gene mutation profiles among luminal-type and basal-type breast cancer cell lines. Breast Cancer Res Treat 2010; 121:53-64.
Kao, J., et al. Molecular profiling of breast cancer cell lines defines relevant tumor models and provides a resource for cancer gene discovery. PLoS ONE 2009; 4: e6146.
Mueller, A., et al., Pharmacological characterization of the chemokine receptor, CCR5. Br J Pharmacol 2002; 135: 1033-43.
Petkovic, Y., et al., I-TAC/CXCL11 is a natural antagonist for CCR5. J Leukoc Biol 2004; 76: 701-8.
Miyashita, M., et al., Effects of serum, transforming growth factor type beta, or 12-O-tetradecanoyl-phorbol-13-acetate on ionized cytosolic calcium concentration in normal and transformed human bronchial epithelial cells. Cancer Res 1989; 49: 63-7.
Prescher, J.A., et al., Guided by the light: visualizing biomolecular processes in living animals with bio luminescence. Curr Opin Chem Biol 2010; 14: 80-9.
Yaal-Hahoshen, N., et al. The chemokine CCL5 as a potential prognostic factor predicting disease progression in stage II breast cancer patients. Clin Cancer Res 2006; 12: 4474-80.
Shideman, C.R., et al., CCL5 evokes calcium signals in microglia through a kinase-, phosphoinositide-, and nucleotide-dependent mechanism. J Neurosci Res 2006; 83: 1471-84.
Dorr, P., et al. Maraviroc (UK-427,857), a potent, orally bioavailable, and selective small-molecule inhibitor of chemokine receptor CCR5 with broad-spectrum anti-human immunodeficiency virus type 1 activity. Antimicrob Agents Chemother 2005; 49: 4721-32.
Strizki, J.M., et al. Discovery and characterization of vicriviroc (SCH 417690), a CCR5 antagonist with potent activity against human immunodeficiency virus type 1. Antimicrob Agents Chemother 2005; 49: 4911-9.
Isik, N., et al., Fluorescence resonance energy transfer imaging reveals that chemokine-binding modulates heterodimers of CXCR4 and CCR5 receptors. PLoS ONE 2008; 3: e3424.
Mira, E., et al. A role for chemokine receptor transactivation in growth factor signaling. EMBO Rep 2001; 2: 151-6.
International Searching Authority, PCT Office of USPTO, PCT International Search Report regarding corresponding PCT Application No. PCT/US2013/040917 issued Oct. 21, 2013, pp. 1-5.
Pestell, The Role of Cyclin D1 and Androgen Receptor (AR) Mutations in Prostate Cancer. Thomas Jefferson University, Annual Progress Report: 2005 Formula Grant [online]. 2009, pp. 29-39, especially p. 31 to 32; [retrieved on Aug. 27, 2012) 1-6-18 Retrieved from the internet: <URL : http://lwebserver.health.state.pa.us/pdf/cure/2008-2009/thomas jefferson university/2005f grant ann prg rep sfy08 thorn jeff.pdf.
Watson et al. Context-Dependent Hormone-Refractory Progression Revealed through Characterization of a Novel Murine Prostate Cancer Cell Line. Cancer Res., 2005, vol. 65, Iss 24, pp. 11565-11571; abstract; p. 11565, col. 2, para 3-4; p. 11566, col. 1, para 5; col. 2, para 3.

(56) References Cited

OTHER PUBLICATIONS

Gil et al. Immortalization of Primary Human Prostate Epithelial Cells by c-Myc. Cancer Res., 2005, vol. 65, Iss 6, pp. 2179-2185; entire document.
Nagy et al. Overexpression of CD24, c-myc and Phospholipase 2A in Prostate Cancer Tissue Samples Obtained by Needle Biopsy. Pathol. Oncol. Res., 2008, vol. 15, pp. 279-283; entire document.
International Searching Authority, PCT Office of USPTO, PCT International Search Report regarding corresponding PCT Application No. PCT/US2012/028546 issued Sep. 14, 2012, pp. 1-6.
Jemal, A., et al., Cancer statistics, 2003. CA Cancer J Clin, 2003. 53(1): p. 5-26.
Singh, D., et al., Gene expression correlates of clinical prostate cancer behavior. Cancer Cell, 2002. 1(2): p. 203-9.
Lapointe, J., et al., Gene expression profiling identifies clinically relevant subtypes of prostate cancer. Proc Natl Acad Sci USA, 2004. 101(3): p. 811-6.
Kattan, M.W., T.M. Wheeler, and P.T. Scardino, Postoperative nomogram for disease recurrence after radical prostatectomy for prostate cancer. J Clin Oncol, 1999. 17(5): p. 1499-507.
Kattan, M.W., et al., A preoperative nomogram for disease recurrence following radical prostatectomy for prostate cancer. J Natl Cancer Inst, 1998. 90(10): p. 766-71.
Graefen, M., et al., Early prostate-specific antigen relapse after radical retropubic prostatectomy: prediction on the basis of preoperative and postoperative tumor characteristics. Eur Urol, 1999. 36(1): p. 21-30.
Dhanasekaran, S.M., et al., Delineation of prognostic biomarkers in prostate cancer. Nature, 2001. 412(6849): p. 822-6.
Varambally, S., et al., The polycomb group protein EZH2 is involved in progression of prostate cancer. Nature, 2002. 419(6907): p. 624-9.
Henshall S.M., et al., Survival analysis of genome-wide gene expression profiles of prostate cancers identifies new prognostic targets of disease relapse. Cancer Res, 2003. 63(14): p. 4196-203.
Latulippe, E., et al., Comprehensive gene expression analysis of prostate cancer reveals distinct transcriptional programs associated with metastatic disease. Cancer Res, 2002. 62(15): p. 4499-506.
Glinsky, G.V., et al., Gene expression profiling predicts clinical outcome of prostate cancer. J Clin Invest, 2004. 113 (6): p. 913-23.
Jenkins, R.B., et al., Detection of c-Myc oncogene amplification and chromosomal anomloies in metastatic prostatic carcinoma by fluorescence in situ hybridization. Cancer Res., 1997. 57(3): p. 524-31.
Qian J., R.B. Jenkins, and D.G. Bostwick, Detection of chromosomal anomalies and c-myc gene amplification in the cribriform pattern of prostatic intraepithelial neoplasia and carcinoma by fluorescence in situ hybridization. Mod Pathol, 1997. 10(11): p. 1113-9.
Ellwood-Yen, K., et al., Myc-driven murine prostate cancer shares molecular features with human prostate tumors. Cancer Cell, 2003. 4(3): p. 223-38.
Creighton, C.J., Multiple oncogenic pathway signatures show coordinate expression patterns in human prostate tumors. PLoS One, 2008. 3(3): p. e1816.
Gumerlock, P.H., et al., Activated ras alleles in human carcinoma of the prostate are rare. Cancer Res, 1991. 51 (6): p. 1632-7.
Carter, B.S., J.I. Epstein, and W.B. Isaacs, ras gene mutations in human prostate cancer. Cancer Res, 1990. 50 (21): p. 6830-2.
Uzgare, A.R., P.J. Kaplan, and N.M. Greenberg, Differential expression and/or activation of P38MAPK, erk1/2, and jnk during the initiation and progression of prostate cancer. Prostate, 2003. 55(2): p. 128-39.
Le Page, C., et al., Expression and localisation of Akt-1, Akt-2 and Akt-3 correlate with clinical outcome of prostate cancer patients. Br J Cancer, 2006. 94(12): p. 1906-12.
Taylor, B.S., et al., Integrative genomic profiling of human prostate cancer. Cancer Cell, 2010. 18(1): p. 11-22.
Weber, M.J. and D. Gioeli, Ras signaling in prostate cancer progression. J Cell Biochem, 2004. 91(1): p. 13-25.

Ware, J.L., et al., Differential reactivity with anti-c-erbB-2 antiserum among human malignant and benighn prostatic tissue [abstract]. Proc Am Assoc Cancer Res, 1989. 30: p. 1737.
Hughes, C., et al., Molecular pathology of prostate cancer. J Clin Pathol, 2005. 58(7): p. 673-84.
Paronetto, M.P., et al., Expression of a truncated form of the c-Kit tyrosine kinase receptor and activation of Src kinase in human prostatic cancer. Am J Pathol, 2004. 164(4): p. 1243-51.
Bull, J.H., et al., Identification of potential diagnostic markers of prostate cancer and prostatic intraepithelial neoplasia using cDNA microarray. Br J Cancer, 2001. 84(11): p. 1512-9.
Cohen, S. and Rabin, B.S., Psychologic stress, immunity, and cancer. J Natl Cancer Inst, 1998. 90(1): p. 3-4.
Lawson, D.A., et al., Isolation and functional characterization of murine prostate stem cells. Proc Natl Acad Sci USA, 2007. 104(1): p. 181-6.
Huang, E.S., et al., Gene expression phenotypes of oncogenic signaling pathways. Cell Cycle, 2003. 2(5): p. 415-7.
Catalona, W.J., et al., Selection of optimal prostate specific antigen cutoffs for early detection of prostate cancer: receiver operating characteristic curves. J Urol, 1994. 152(6 Pt 1): p. 2037-42.
Thompson, I.M., et al., Effect of finasteride on the sensitivity of PSA for detecting prostate cancer. J Natl Cancer Inst, 2006. 98(16): p. 1128-33.
Akimoto, S., et al., Relationship between prostate-specific antigen, clinical stage, and degree of bone metastasis in patients with prostate cancer: comparison with prostatic acid phosphatase and alkaline phosphatase. Int J Urol, 1997. 4(6): p. 572-5.
Hanley, J.A. and B.J. McNeil, The meaning and use of the area under a receiver operating characteristic (ROC) curve. Radiology, 1982. 143(1): p. 29-36.
Sharma, A., et al., Novel functions of the retinoblastoma tumor suppressor in controlling lethal tumor phenotypes. (In Press). J Clin Invest, 2010: p. (In Press).
Neve, R.M., et al., A collection of breast cancer cell lines for the study of functionally distinct cancer subtypes. Cancer Cell, 2006. 10(6): p. 515-27.
Chin, K., et al., Genomic and transcriptional aberrations linked to breast cancer pathophysiologies. Cancer Cell, 2006. 10(6): p. 529-41.
Welsh, J.B., et al., Analysis of gene expression identifies candidate markers and pharmacological targets in prostate cancer. Cancer Res, 2001. 61(16): p. 5974-8.
Mori, S., et al., Utilization of genomic signatures to identify phenotype-specific drugs. PLoS One, 2009. 4(8): p. e6772.
Sato, K., et al., Clinical significance of alterations of chromosome 8 in high-grade, advanced, nonmetastatic prostate carcinoma. J Natl Cancer Inst, 1999. 91(18): p. 1574-80.
Casimiro, M., et al., ErbB-2 induces the cyclin D1 gene in prostate epithelial cells in vitro and in vivo. Cancer Res, 2007. 67(9): p. 4364-72.
Gioeli, D., Kraus, S., and Weber, M.J., Signal Transduction by the Ras-MAP Kinase Pathway in Prostate Cancer Progression, in Prostate cancer: signaling networks, genetics, and new treatment strategies, R.G. Pestell and M.T. Nevalainen, Editors. 2008, Humana Press: Totowa, NJ. p. 223-256.
Scherl, A., et al., Prostatic intraepithelial neoplasia and intestinal metaplasia in prostates of probasin-RAS transgenic mice. Prostate, 2004. 59(4): p. 448-59.
Ilio, K.Y., et al., The primary culture of rat prostate basal cells. J Androl, 1998. 19(6): p. 718-24.
Li, Z. et al., Cyclin D1 regulates cellular migration through the inhibition of thrombospondin 1 and ROCK signaling. Mol Cell Biol, 2006. 26(11): p. 4240-56.
Liu, M., et al., p21CIP1 attenuates Ras- and c-Myc-dependent breast tumor epithelial mesenchymal transition and cancer stem cell-like gene expression in vivo. Proc Natl Acad Sci USA, 2009. 106(45): p. 19035-9.
Thirkill,T.L., et al., Macaque trophoblast migration is regulated by RANTES. Exp Cell Res 2005; 305: 355-64.
Abel, S., et al. Assessment of the pharmacokinetics, safety and tolerability of maraviroc, a novel CCR5 antagonist, in healthy volunteers. Br J Clin Pharmacol 2008; 65 Suppl 1: 5-18.

(56) References Cited

OTHER PUBLICATIONS

Vaday, G.G., et al., Expression of CCL5 (RANTES) and CCR5 in prostate cancer. Prostate 2006; 66: 124-34.
Perret, G.Y., et al., New pharmacological strategies against metastatic spread. Fundam Clin Pharmacol 2008; 22: 465-92.
Sugasawa, H., et al. Prognostic significance of expression of CCL5/RANTES receptors in patients with gastric cancer. J Surg Oncol 2008; 97: 445-50.
Thompson, I.M., et al. ("Prevalence of prostate cancer among men with a prostate-specific antigen level < or = 4.0 ng per milliliter," New England Journal of Medicine 2004, 350(22), 2239-2246.
Smith, D.S., et al. ("The early detection of prostatecarcinoma with prostate specific antigen: The Washington University experience," Cancer 1997, 80(9), 1853-1856.
Scher, H. I., et al., J Clin Oncol 2005, 23, 8253-8261.
Schindler, T., et al. In Molecular Cell, 1999 (3), 639, 647.
Hamby, J., et al., J. Med. Chem. 40, 1997, 2296-2303.
Panek, R. L., et al., J. Pharmacal. Exp. Ther. 283, 1997, 1433-1444.
Klutchko, S.R., et al., J. Med. Chem. 41, 1998, 3276-3292.
Gamse, R., et al.—J. Bone Miner. Res. 14 (Suppl 1) 1999, S487.
Cambien, B. et al., "CCL5 Neutralization Restricts Cancer Growth and Potentiates the Targeting of PDGFR$\beta$ in Colorectal Carcinoma", PLoS ONE, Dec. 2011, vol. 6, Issue 12, e28842-1 to e28842-11.
Van Deventer, H. W. et al., "C-C Chemokine Receptor 5 on Stromal Cells Promotes Pulmonary Metastasis", Cancer Res 2005; 65: (8), Apr. 15, 2005, 3374-3379.
Momse, K. et al., "Close Resembleance between Chemokine Receptor Expression Profiles of Lymphoproliferative Disease of Granular Lymphocytes and Their Normal Counterparts in Association with Elevated Serum Concentrations of IP-10 and MIG", International Journal of Hematology, 86 (2007), 174-179.
Makishima, H. et al., "Significance of chemokine receptor expression in aggressive NK cell leukemia", Leukemia (2005) 19, 1169-1174.
Partial European Search Report issued on Mar. 17, 2016 for corresponding European Patent Application No. 13790117.9.

\* cited by examiner

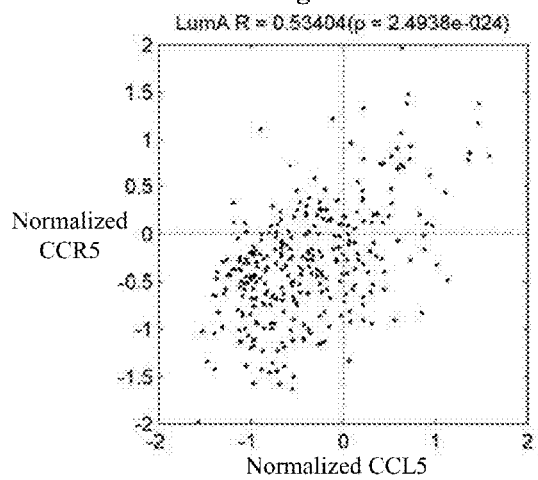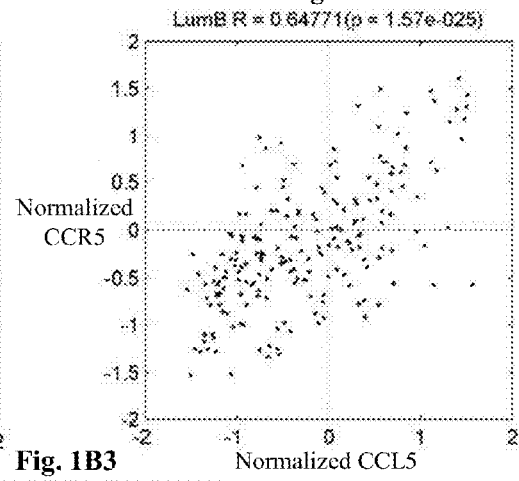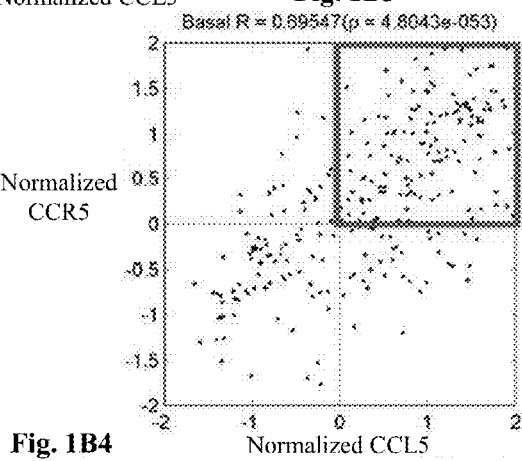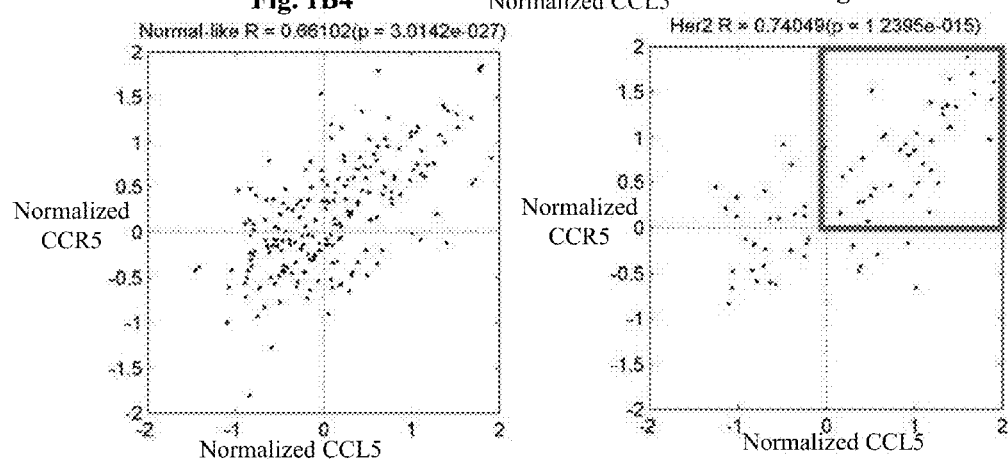

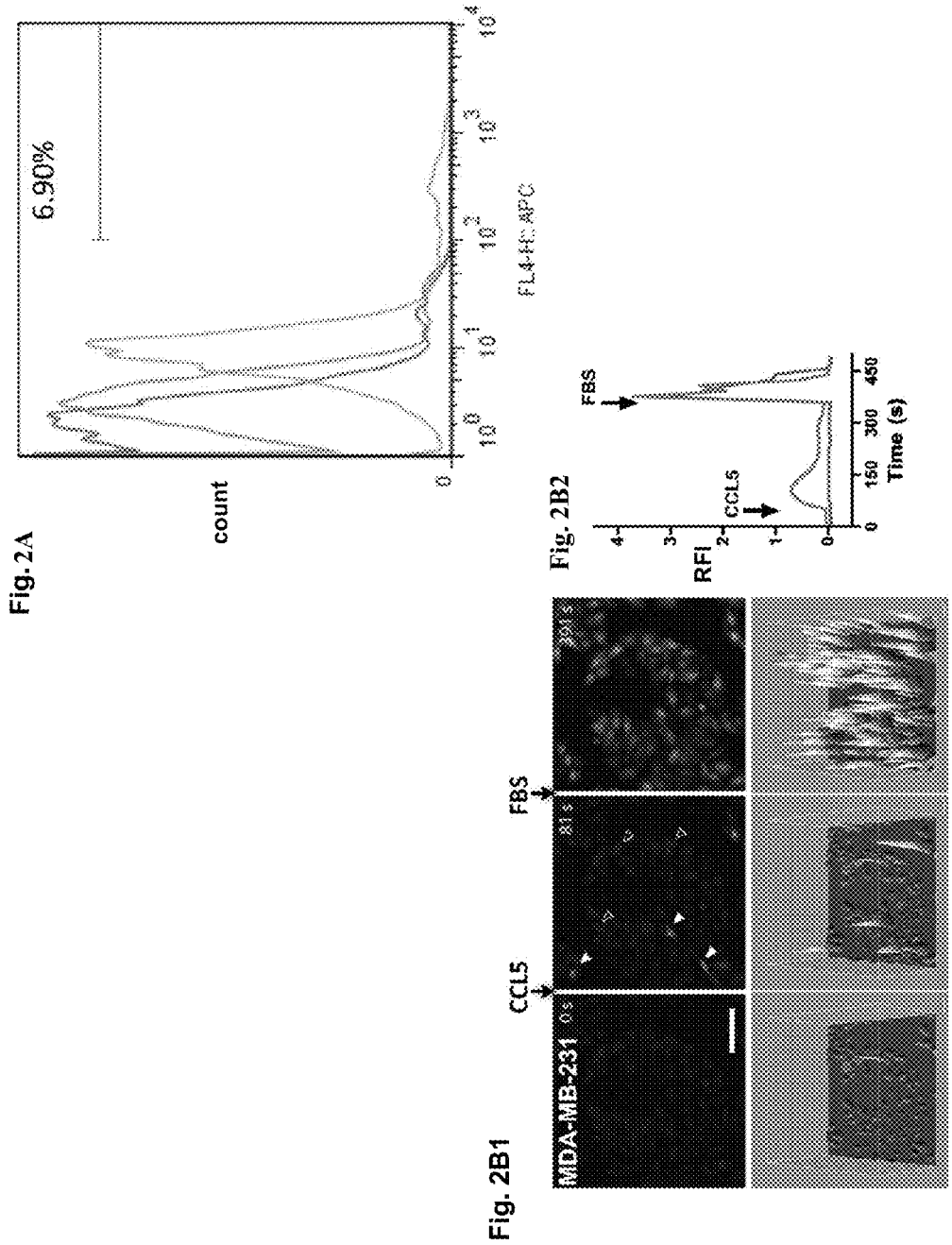

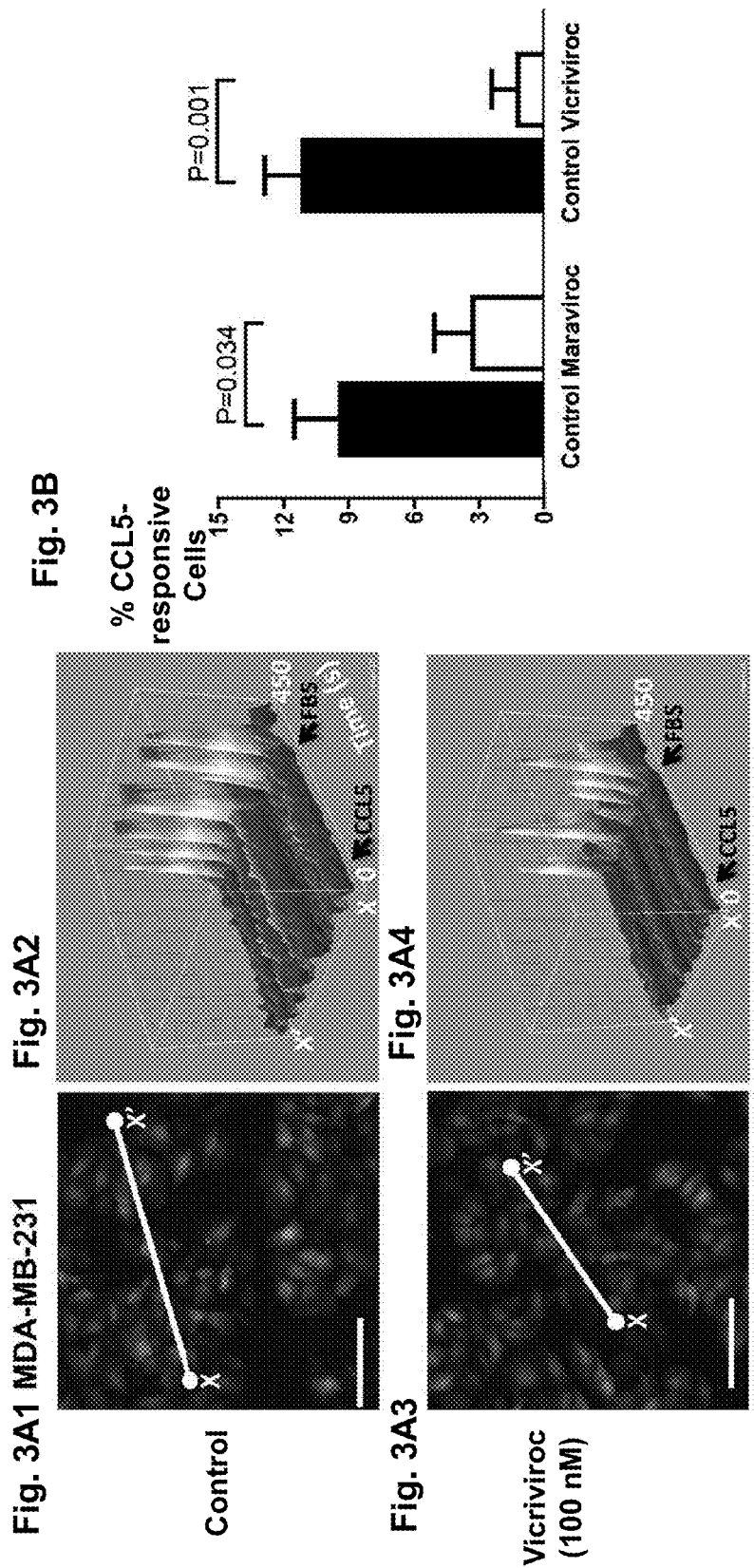

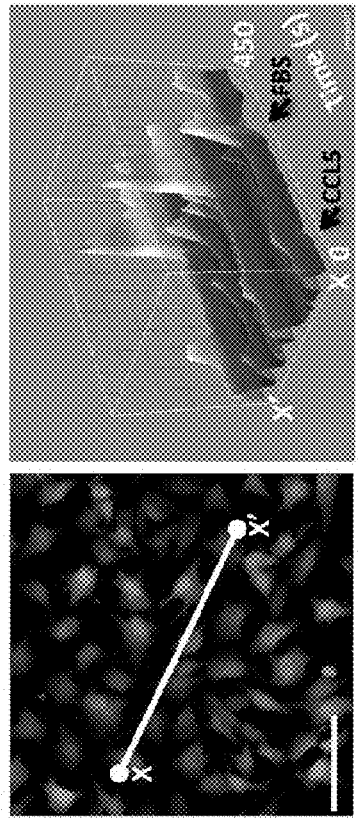
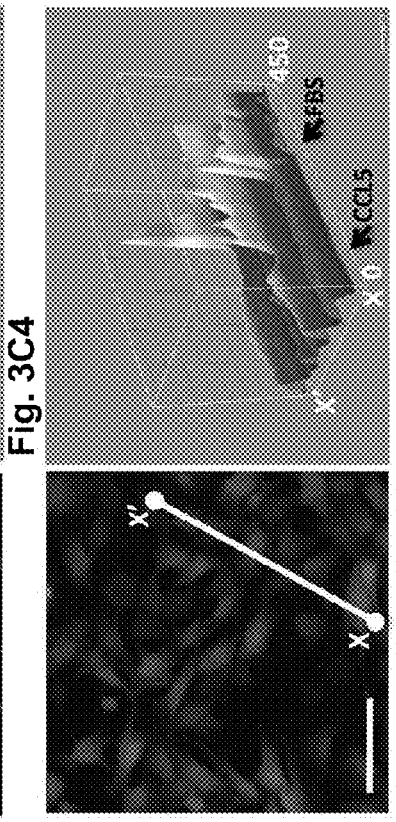
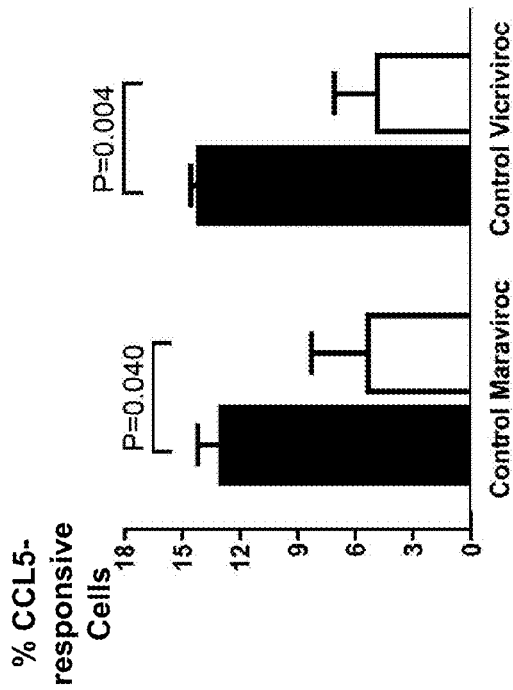
Fig. 3C1 Hs578T Control
Fig. 3C2
Fig. 3C3 Maraviroc (100 nM)
Fig. 3C4
Fig. 3D

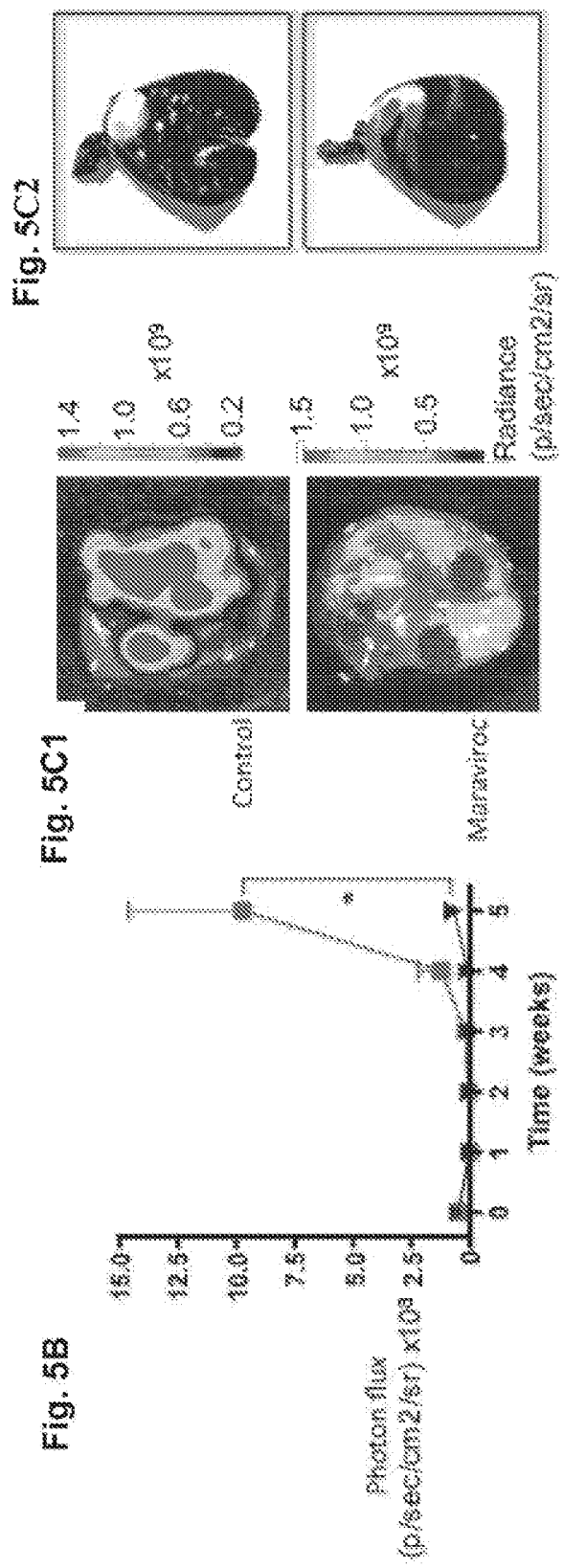

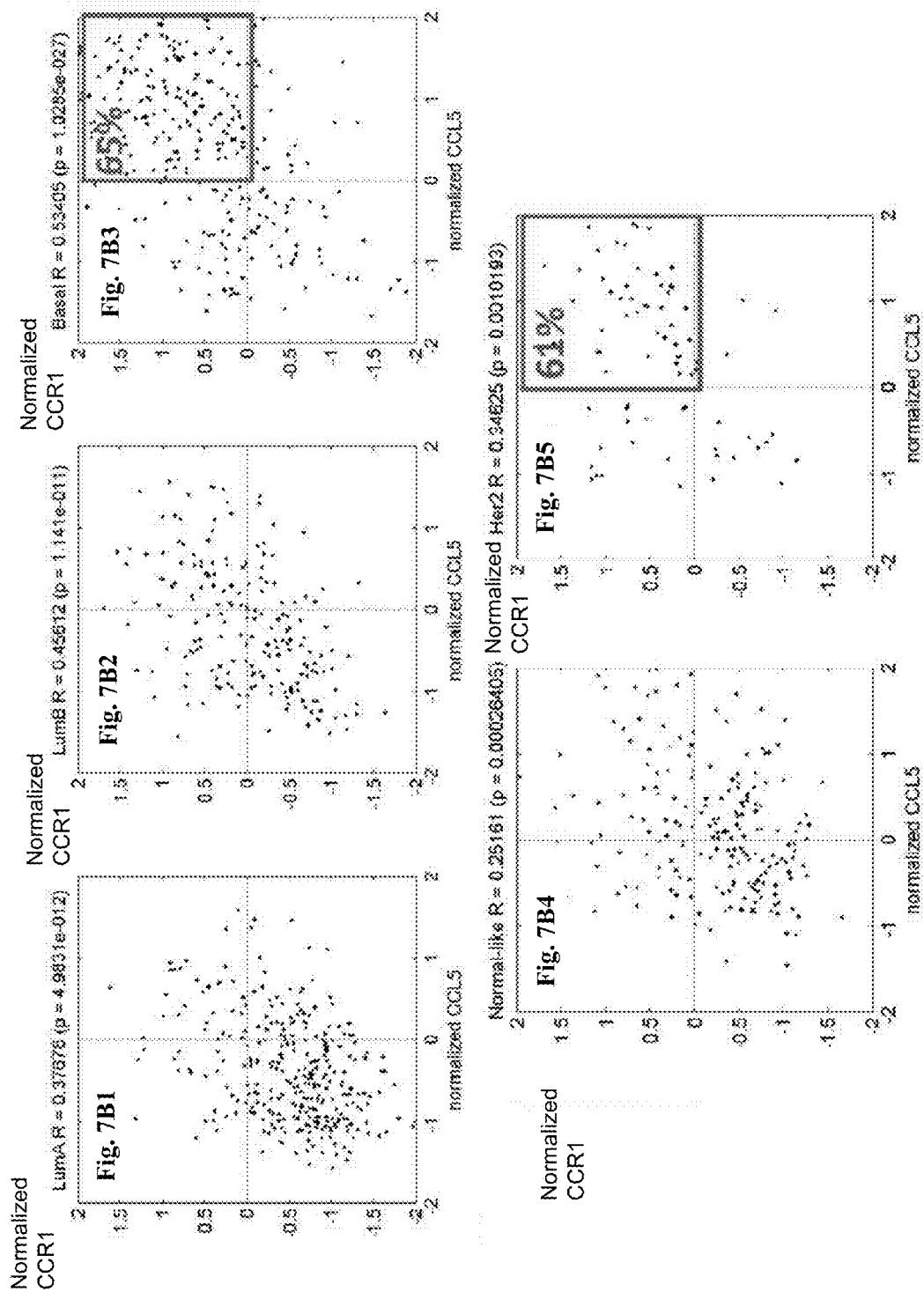

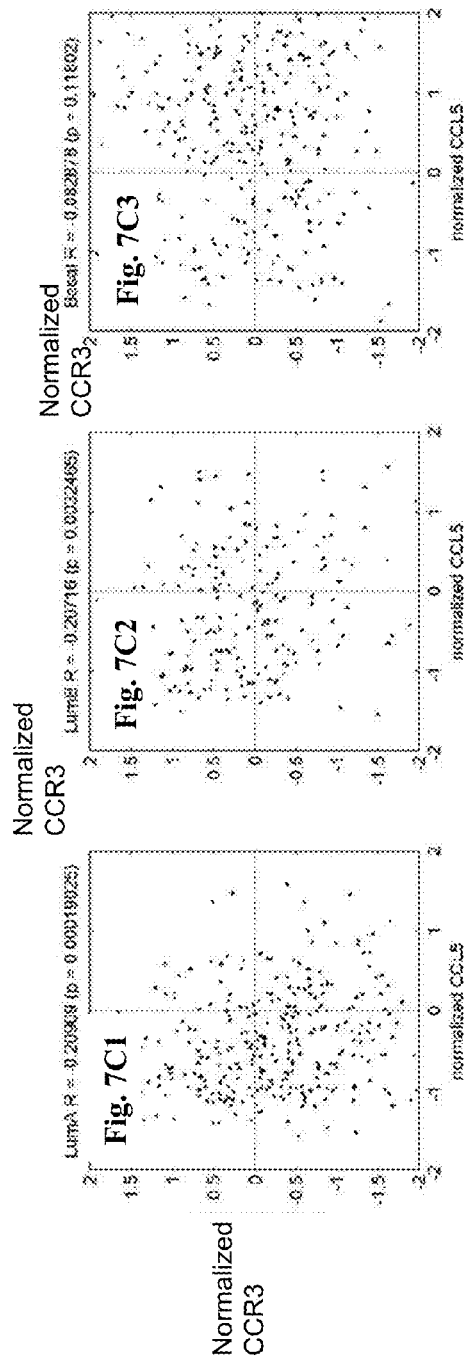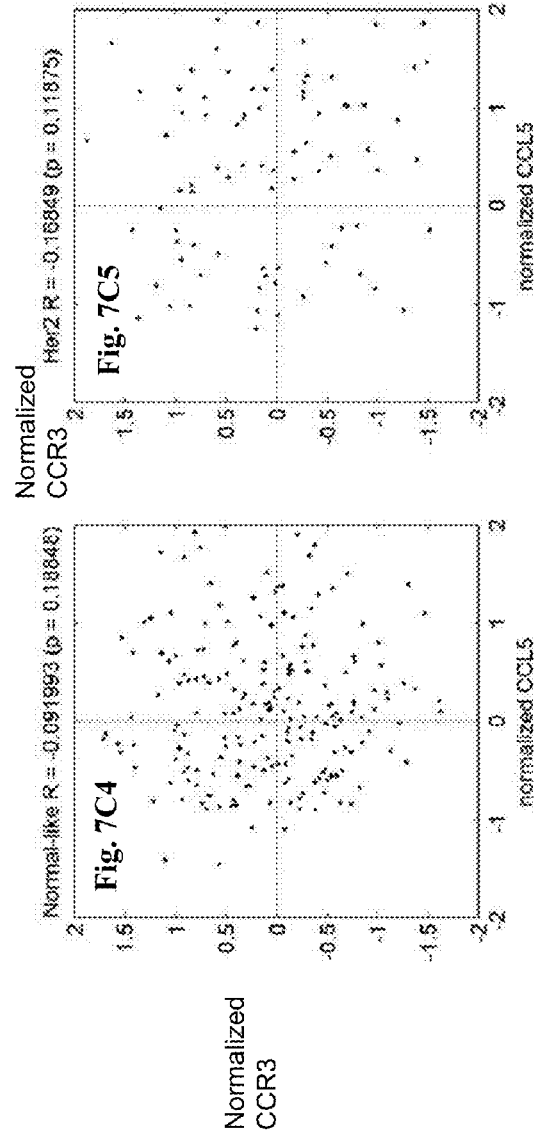

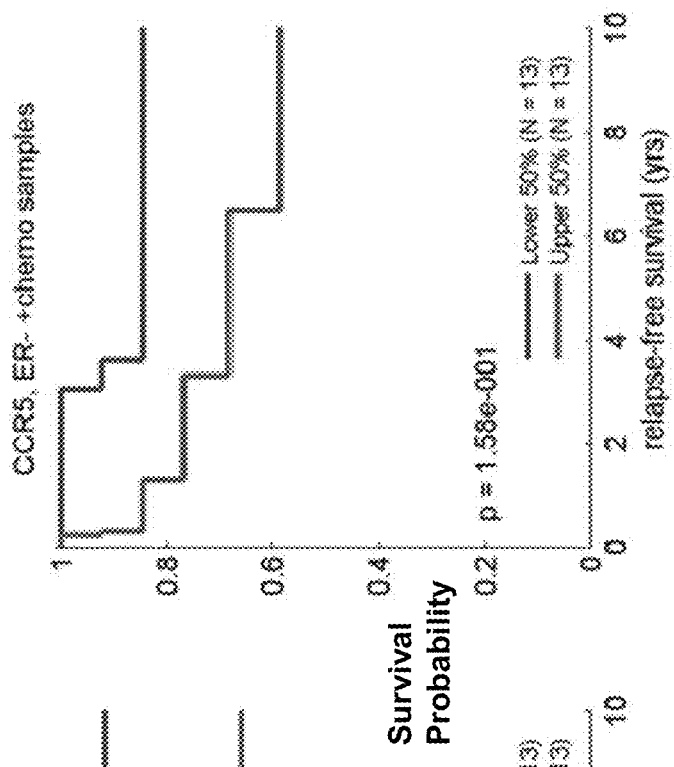
Fig. 7D2
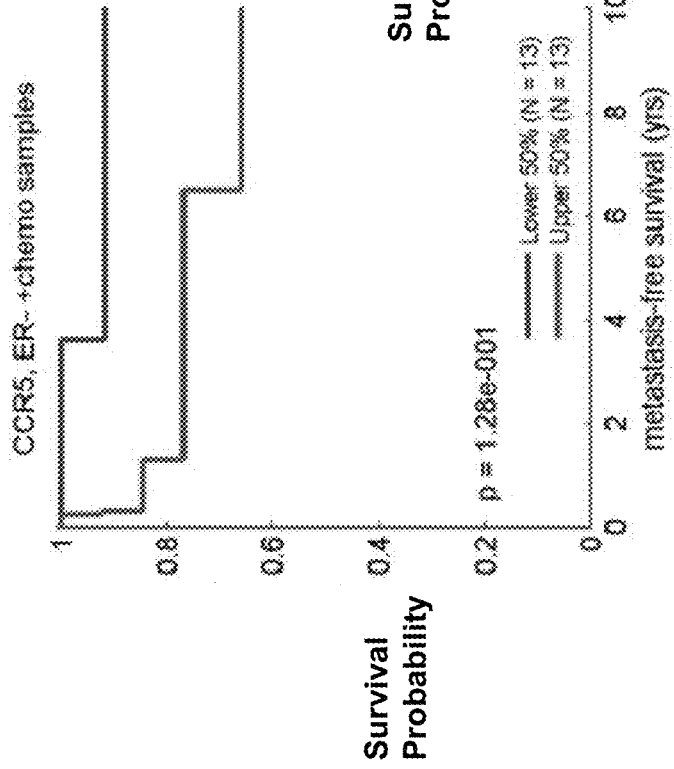
Fig. 7D1

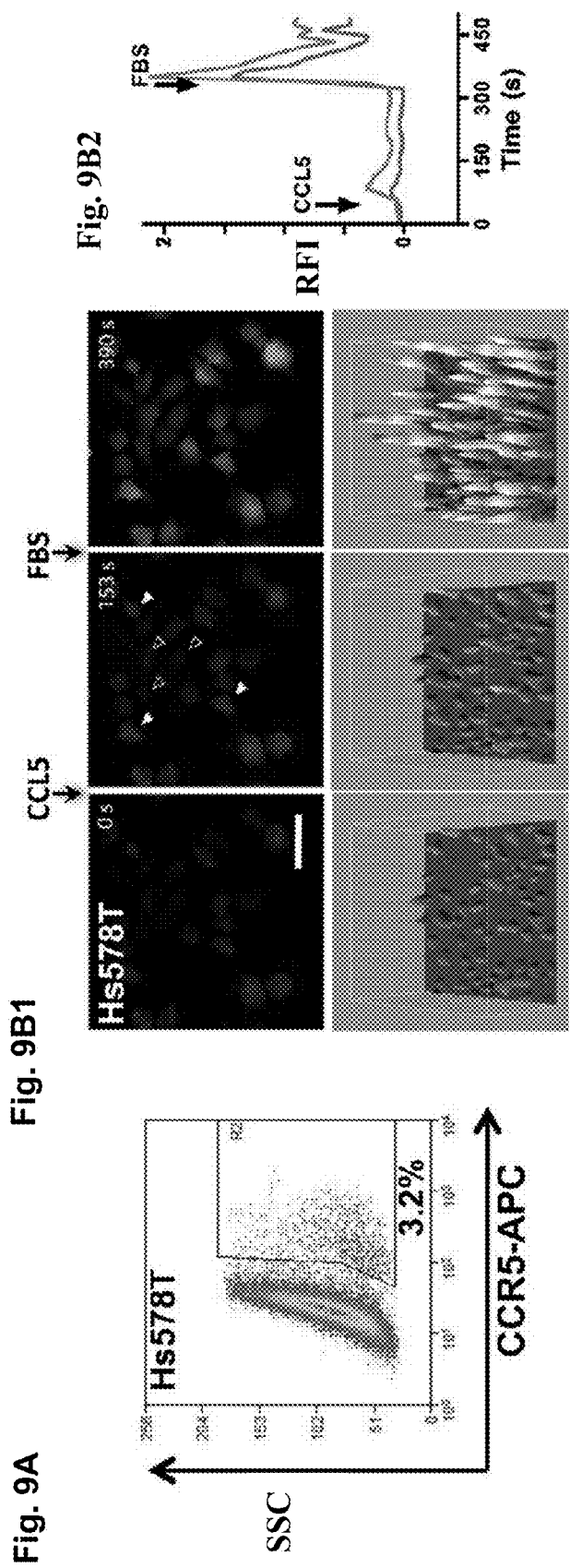

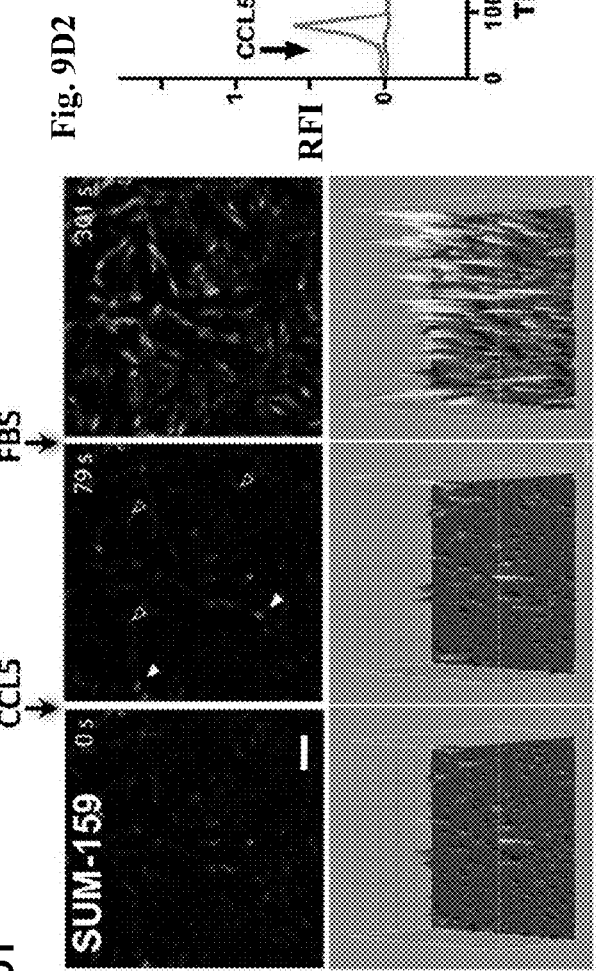
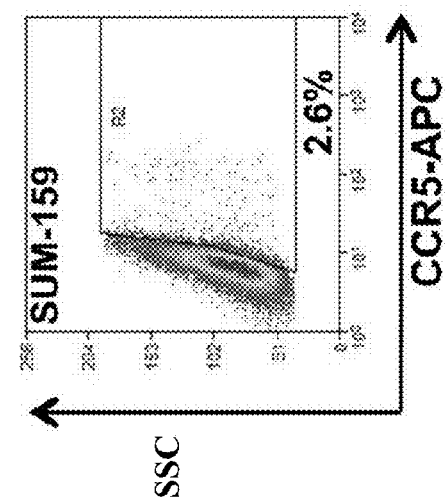

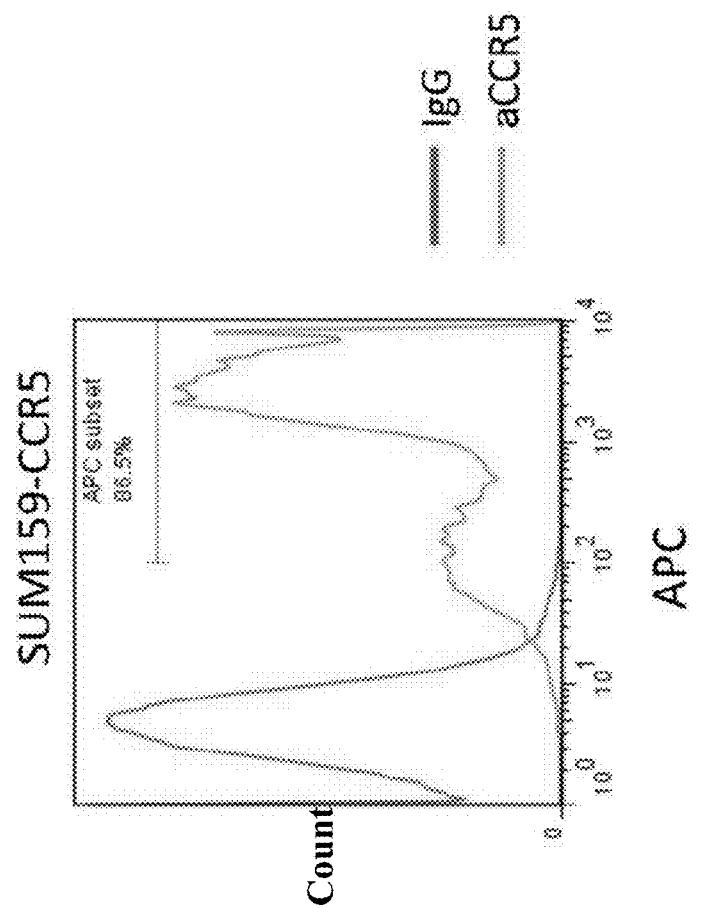
Fig. 10A1
Fig. 10A2
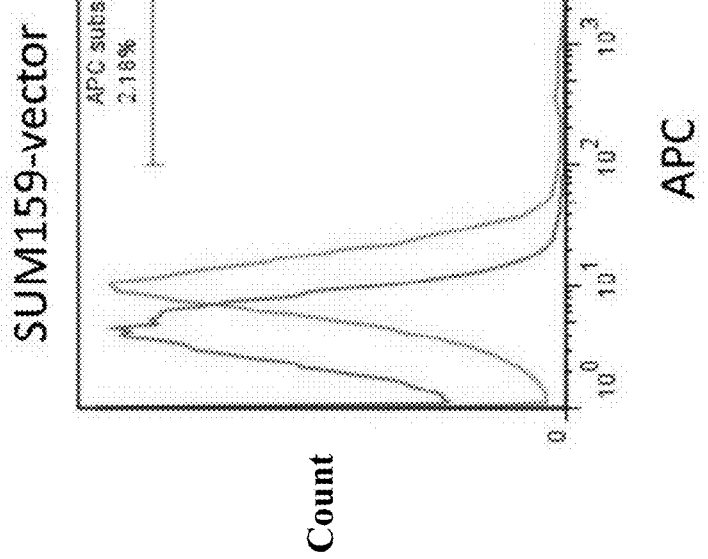

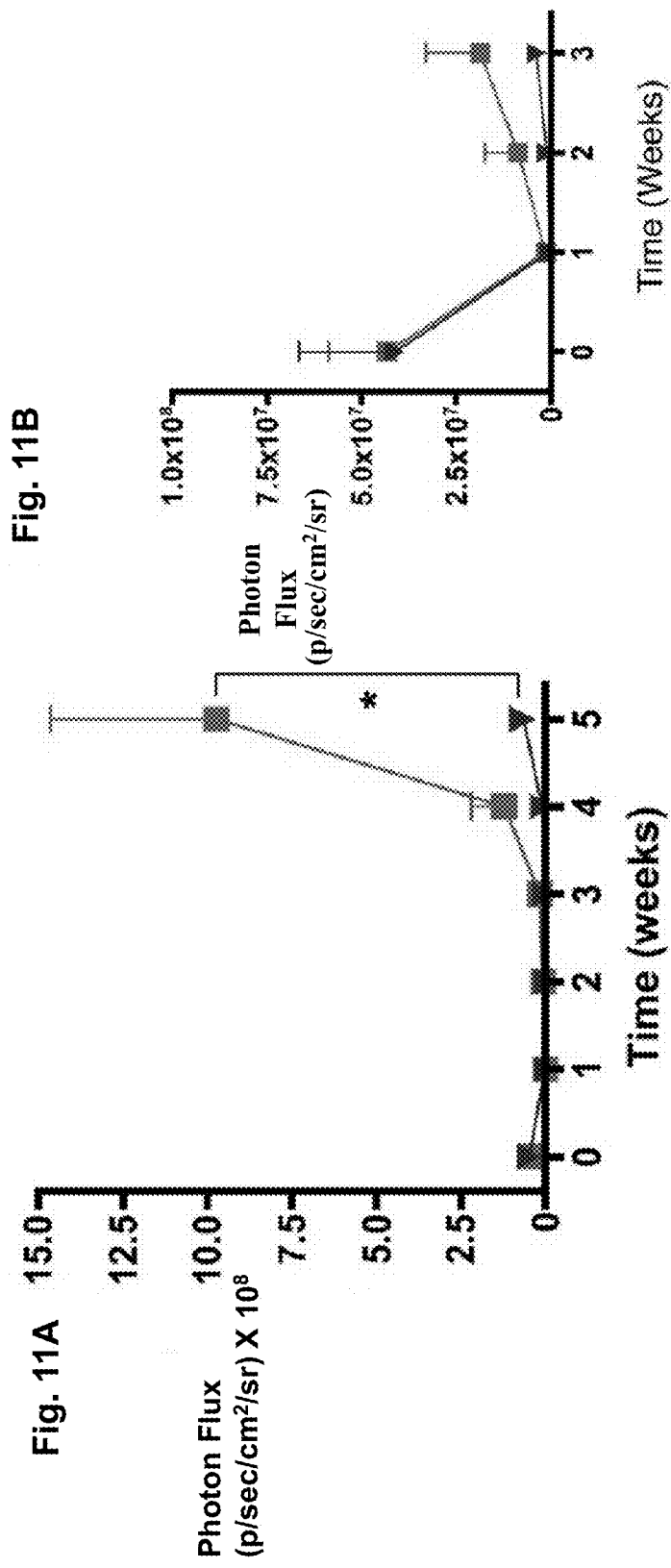

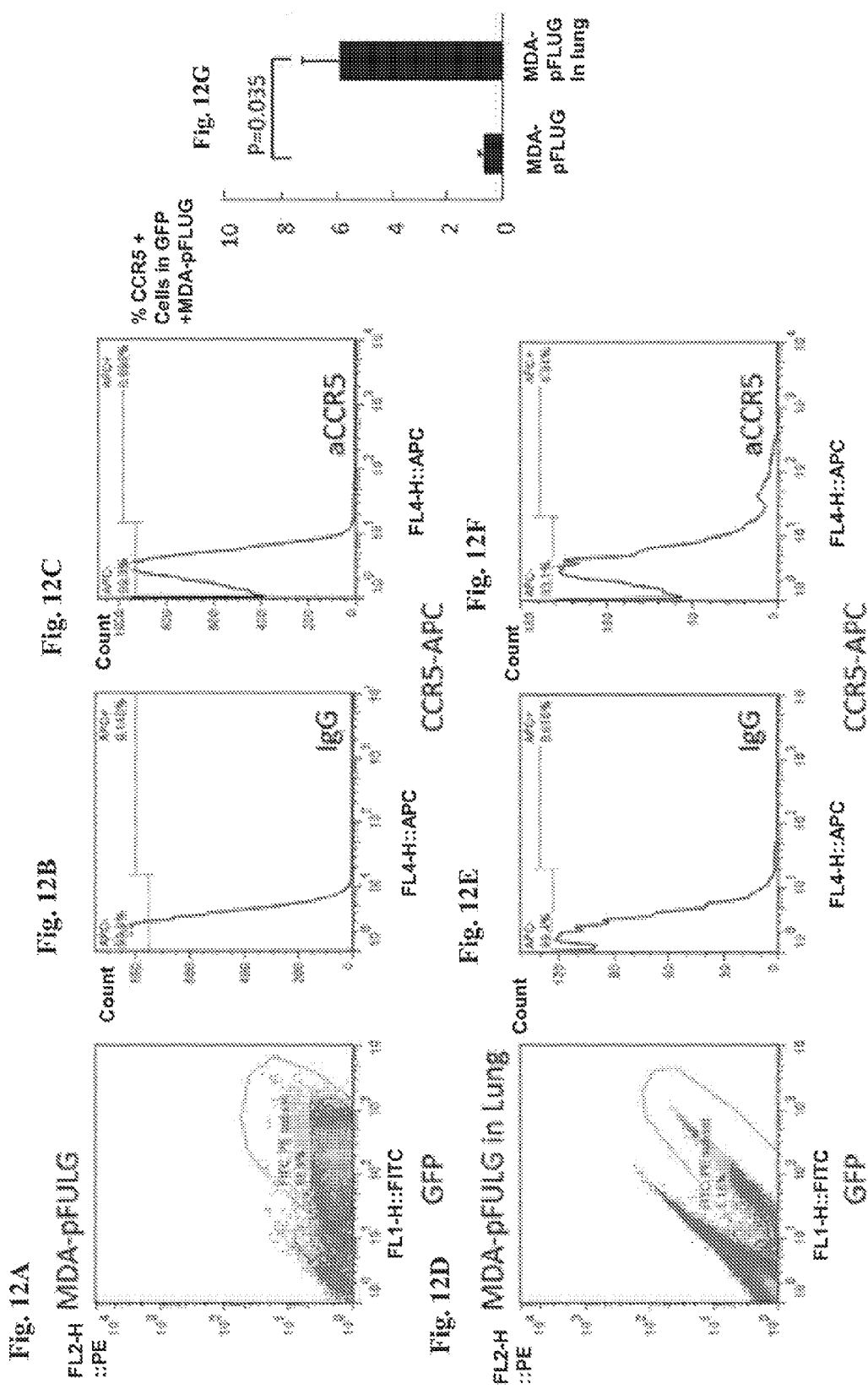

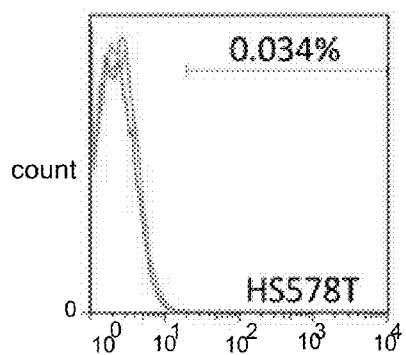
Fig. 13A1
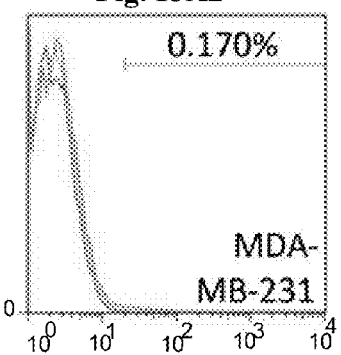
Fig. 13A2
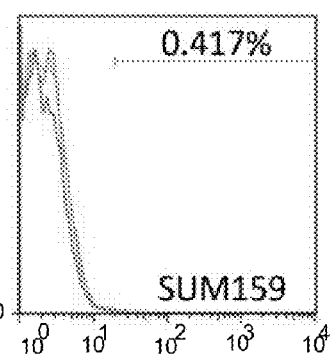
Fig. 13A3
CCR1-APC
Fig. 13A4 — No stain     IgG     aCCR1     Fig. 13A5
CCR1-APC

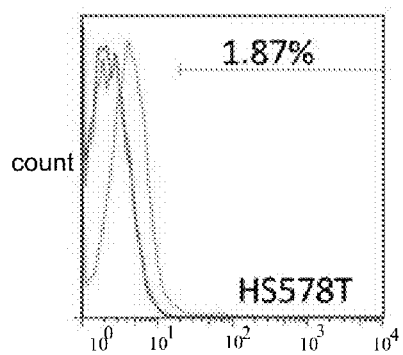
Fig. 13B1
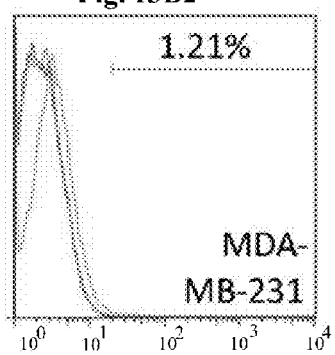
Fig. 13B2
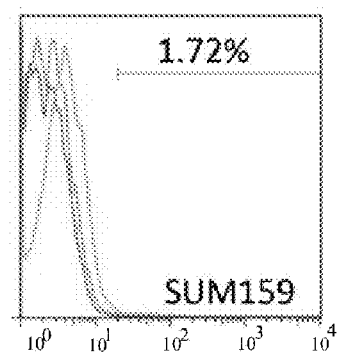
Fig. 13B3
CCR3-APC
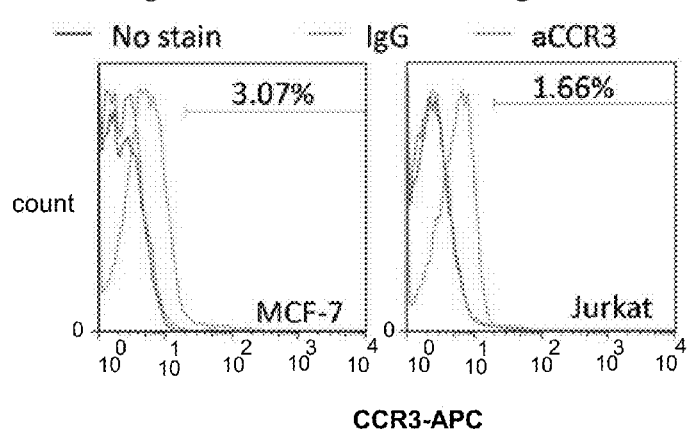
Fig. 13B4   Fig. 13B5
CCR3-APC

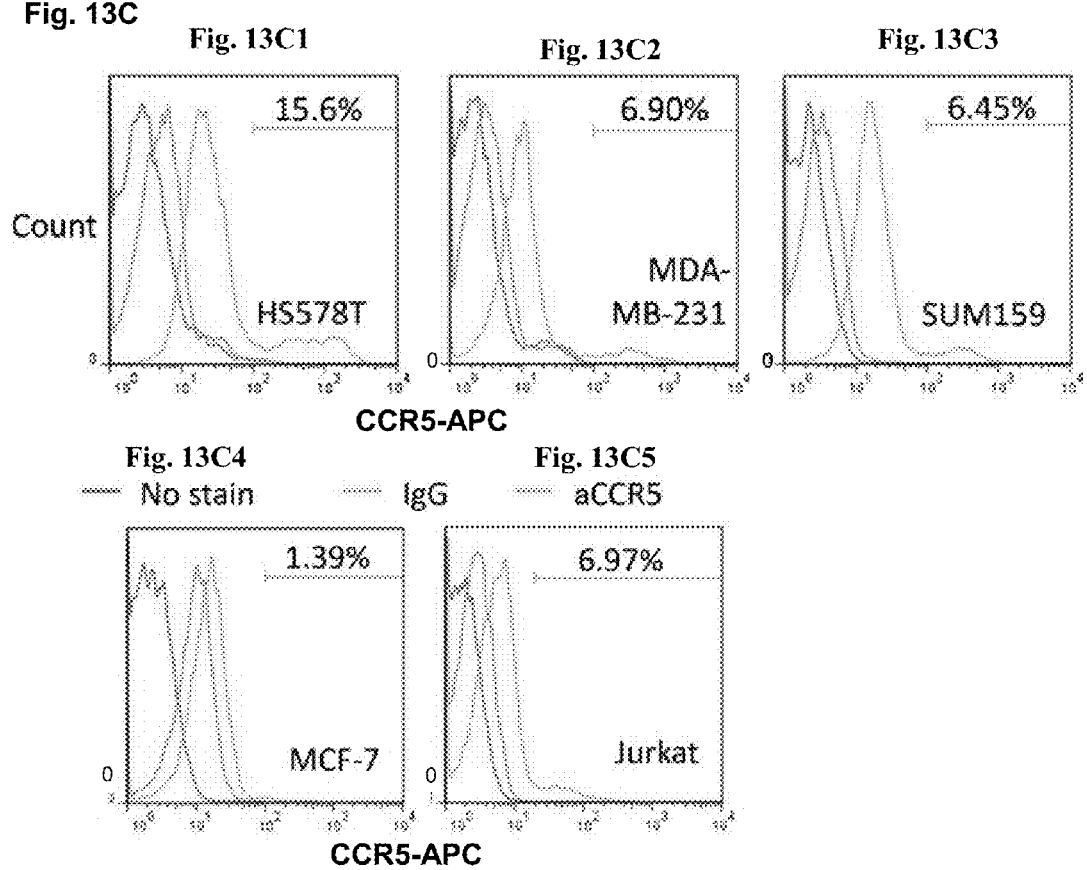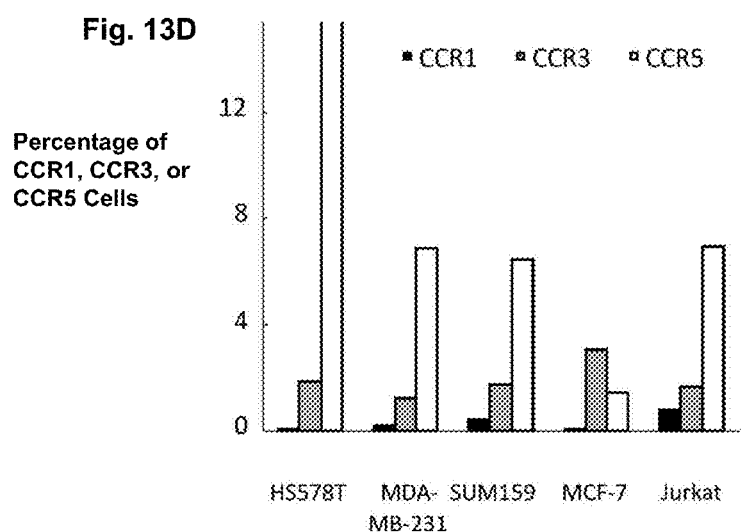

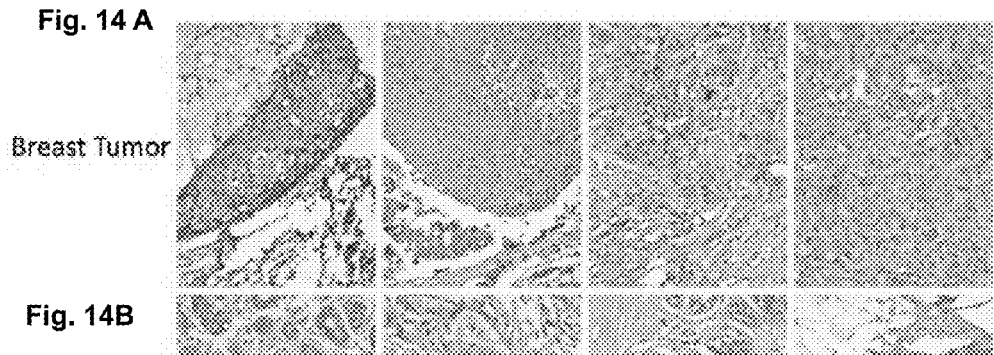
Fig. 14 A
Breast Tumor
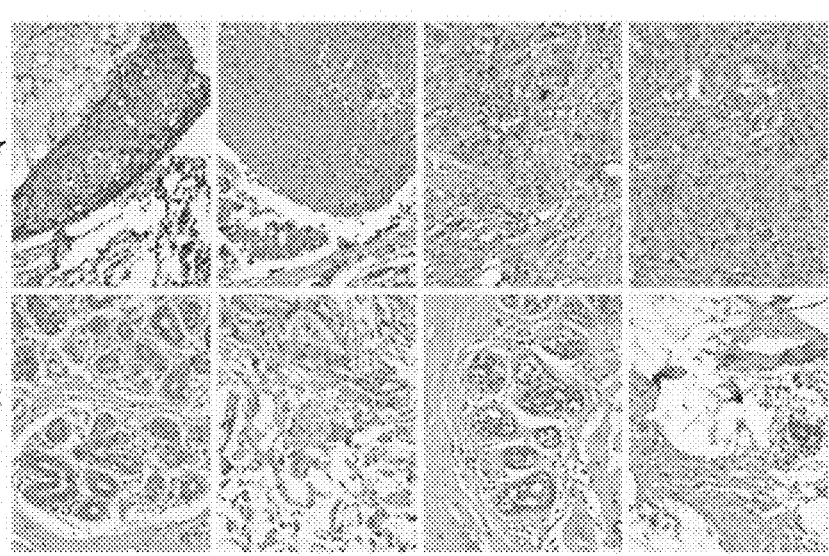
Fig. 14B
Normal Breast
Fig. 14C
Breast Tumor
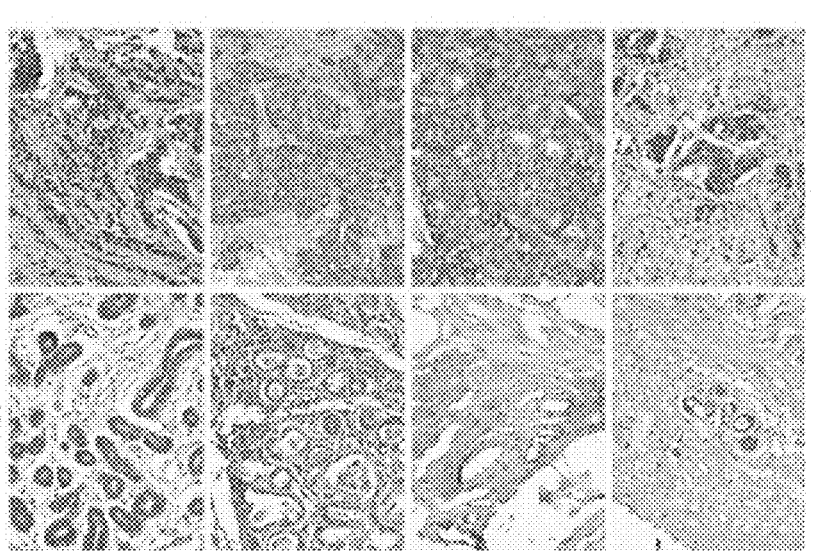
Fig. 14D
Normal Breast

USE OF MODULATORS OF CCR5 IN THE TREATMENT OF CANCER AND CANCER METASTASIS

CROSS-REFERENCE TO RELATED APPLICATIONS

This application claims the benefit of U.S. Provisional Patent Application Nos. 61/646,586, filed May 14, 2012, and entitled "Use Of Modulators Of CCR5 In The Treatment Of Cancer And Cancer Metastasis"; and 61/646,593, filed May 14, 2012, and entitled "Use Of Modulators Of CCR5 In The Treatment Of Cancer And Cancer Metastasis", both of which are incorporated by reference herein in their entirety.

STATEMENT REGARDING FEDERALLY SPONSORED R&D

This invention was supported in part by PASPA-UNAM (M.A.V-V.), NIH grants R01CA070896, R01CA075503, R01CA132115, R01CA107382, R01CA086072 (R.G.P.), R01CA120876 (M.P.L), the Kimmel Cancer Center NIH Cancer Center Core grant P30CA056036 (R.G.P.), generous grants from the Dr. Ralph and Marian C. Falk Medical Research Trust and the Margaret Q. Landenberger Research Foundation, and a grant from Pennsylvania Department of Health (R.G.P.). Accordingly, the United States government has certain rights in the invention.

FIELD OF THE INVENTION

This disclosure is directed, in part, to a method of determining whether a subject having cancer is at risk for developing metastasis of the cancer and a method of blocking cancer methastasis.

BACKGROUND OF THE INVENTION

Breast cancer causes the death of 40,000 women in the USA and 410,000 women in the world annually.[1] Despite advances in the treatment of the disease, 20% to 30% of patients with early breast cancers will experience relapse with distant metastatic disease.[2] In those patients, metastasis is the main cause of death. Patients with basal tumors have increased risk of metastasis and lower survival rate.[3, 4] Kennecke et al. studied 3,726 breast cancer patients and reported that the basal tumors have higher frequencies of metastases and reduced time from identification of metastases to death compared to that of patients with luminal A or B tumors.[4] The absence of AR, ER, and HER-2 commonly found in basal breast tumors[5] means that they are unlikely to respond to hormone therapies or HER-2 targeted therapies. Currently, chemotherapy, radiation, and surgery are the only choices for patients with basal breast cancers, but all demonstrate poor outcomes.[6] The need for a specific targeted therapy for basal breast cancer remains urgent.

BRIEF SUMMARY OF THE INVENTION

Certain aspects of embodiments disclosed herein by way of example are summarized below. It should be understood that these aspects are presented merely to provide the reader with a brief summary of certain forms an invention disclosed and/or claimed herein might take and that these aspects are not intended to limit the scope of any invention disclosed and/or claimed herein. Indeed, any invention disclosed and/or claimed herein may encompass a variety of aspects that may not be set forth below.

The present disclosure generally relates to various methods, including methods of determining whether a subject has cancer or is at risk for developing cancer and/or is at risk for developing cancer metastasis. In some embodiments, the methods of the present invention include methods of treating, preventing, or managing a neoplasm or a cancer metastasis in a patient. In some embodiments, the methods of the present invention include in vivo methods for down regulating CCR5 expression in a set of one or more prostate cancer cell lines derived from transduction of murine epithelial or prostate epithelial cells and transformed by at least one oncogene selected from the group consisting of NeuT, Ha-Ras, and c-Src. In some exemplary embodiments drugs that target the HIV receptor CCR5, which the virus uses to enter and infect host cells, are used to prevent migration and spread of cancer cells from their primary tissue to secondary sites in the body of the patient. In one embodiment, a drug that targets the HIV receptor CCR5 may be used as an adjuvant therapy, or adjuvant care, wherein the drug is administered to the patient in addition to a primary, main or initial treatment for cancer. In some embodiments, such adjuvant therapy may be administered concomitantly or concurrently as other therapies for cancer. In one embodiment, such adjuvant therapy may be given concurrently as other adjuvant therapies or following other adjuvant therapies.

In some embodiments, when CCR5 receptor antagonists are used as adjuvant therapy they improve prognosis in cancer patients. In some embodiments, where a plurality of anticancer drugs are used in combination for cancer therapy, a CCR5 receptor antagonist may be included as an adjuvant therapy in order to improve the therapeutic effect by blocking metastasis of the cancer being treated, thereby contributing to improving clinical outcomes of the cancer therapy.

BRIEF DESCRIPTION OF THE SEVERAL VIEWS OF THE DRAWINGS

The foregoing summary, as well as other features, aspects, and advantages of the present invention and the following detailed description of embodiments of the invention, will e better understood when read in conjunction with the claims and the appended drawings of an exemplary embodiments, wherein:

FIGS. 1B1 to 1B5 illustrate scatter plots and correlation analysis (Student t test) of the expression of CCL5 and CCR5 among the breast cancer molecular subtypes of luminal A, luminal B, basal, normal-like, and Her-2;

FIG. 2A illustrates flow cytometric histograms of the CCR5 expression in MDA-MB-231 breast cancer cells identified a subpopulation of CCR5$^+$ cells;

FIGS. 2B1 and 2B2 illustrate induction of calcium signaling in cells loaded with Fluo-4-AM before the sequential addition of CCL5 (60 μg/mL) and FBS (5%);

FIG. 2E, 3D invasion assays for MCF-10A cells and MCF-10A-NeuT, -Ras, and -Src derivatives showing that CCL5-induced invasion is activated by oncogenic transformation;

FIGS. 3A1 to 3A4 illustrate(s) intensity versus time analysis of Fluo-4 AM-loaded MDA-MB-231 cells treated with the CCR5 antagonists maraviroc or vicriviroc (100 nmol/L) for 30 minutes before the addition of CCL5 (60 μg/mL);

FIG. 3B illustrates a comparison of the fraction of cells with increased fluorescence intensity upon addition of CCL5;

FIG. 3C1 to 3C4 show CCL5-induced calcium signaling blocked by CCR5 antagonists in Hs578T cells;

FIG. 3D illustrates quantification (mean±SEM) of 3 to 4 independent experiments shown in FIGS. 3A-3C;

FIG. 5B shows quantification (mean±SEM, n=6) of in vivo bioluminescent images (BLIs) in the control (vehicle-treated NOD/SCID mice, red line/squares) and treated groups (maraviroc-treated NOD/SCID mice, blue line/triangles);

FIGS. 5C1 and 5C2 show the presence of pulmonary tumors and the differences between treatments corroborated by ex vivo imaging (5C1) and India ink staining (5C2);

FIGS. 7B1 to 7B5 illustrate scatter plots and correlation analysis using students' t-tests for the expression of CCR1 and CCR5 among the breast cancer molecular subtypes from a set of 2250 human breast cancer data shown in FIG. 1A;

FIGS. 7C1 to 7C5 and show scatter plots and correlation analysis for the expression of CCR3 and CCL5 among the breast cancer molecular subtypes from a set of 2250 human breast cancer data shown in FIG. 1A;

FIGS. 7D1 and 7D2 show Kaplan Meier curves for patients with breast cancer samples enriched for the highest level of CCR5 (up of 50%) versus the lower level CCR5 expression (lower 50%);

FIG. 9A illustrates flow cytometry plot of the CCR5 expression in HS578T cells stably transfected with allophycocyanin (APC)-labeled antibody to CCR5;

FIGS. 9B1 and 9B2 illustrate induction of calcium signaling in HS578T cells loaded with Fluo-4-AM before the sequential addition of CCL5 (60 µg/mL) and fetal bovine serum (FBS) (5%), wherein RFI represents relative fluorescence intensities. The red traces are of cells that did not respond to the addition of CCL5 ligand—but do respond to FBS (fetal bovine serum), the green line is the trace for the cells that do respond to the additions of CCL5, and also respond to FBS. This data tells us that the MDA-MB-231 cells are a population of cells in which some cells have the receptor and respond to CCL5—and some cells that do not have the CCR5 receptor and do not respond to its ligand CCL5;

FIG. 9C illustrates flow cytometry plot of the CCR5 expression in SUM159 cells stably transfected with allophycocyanin (APC)-labeled antibody to CCR5.

FIGS. 9D1 and 9D2 illustrate induction of calcium signaling in SUM159 cells loaded with Fluo-4-AM before the sequential addition of CCL5 (60 µg/mL) and fetal bovine serum (FBS) (5%), wherein RFI represents relative fluorescence intensities. The red traces are of cells that did not respond to the addition of CCL5 ligand-but do respond to FBS (fetal bovine serum), the green line is the trace for the cells that do respond to the addition of CCL5, and also respond to FBS. This data tells us that the SUM-159 cells are a population of cells in which some cells have the receptor and respond to CCL5—and some cells that do not have the CCR5 receptor and do not respond to its ligand CCL5;

FIGS. 10A1 and 10A2 and illustrates fluorescence-activated cell sorting (FACS) analysis for the abundance of CCR5 receptor in either the SUM159-vector control cells or SUM 159 cells stably overexpressing the CCR5 receptor. APC-labeled antibody to CCR5 was used to follow the CCR5 positive cells;

FIG. 11A illustrates that fact that maraviroc reduces MDA-MB-231 breast cancer lung metastasis burden as evidenced by the quantification results of weekly BLI, conducted for 5 weeks on maraviroc-treated NOD/SCID mice, wherein the lung metastatic tumor radiance antemortem was used as a surrogate measurement of tumor burden to the lungs (per FIG. 5B).

FIG. 11B illustrates the fact that maraviroc reduces MDA-MB-231 breast cancer lung metastasis burden as evidenced by the quantification illustrates results of weekly BLI, conducted for 5 weeks on vehicle-treated NOD/SCID mice, wherein the lung metastatic tumor radiance antemortem was used as a surrogate measurement of tumor burden.

FIGS. 12A to 12G illustrate the fact that pulmonary tumors are enriched in $CCR5^{+4}$ cells as evidenced by the FACS analysis of the proportion of CCR5+ cells into metastatic tumors caused by tail vein injection of MDA.pFULG cells. The proportion of CCR5+ cells within eGFP+ MDA.p-FULG cells in culture (FIGS. 12A, 12B and 12C) was compared with that of cells isolated from metastatic tumors (FIGS. 12D, 12E and 12F). Analysis of data (FIG. 12G) showed an eight-fold increase in CCR5+ fraction in tumors (mean±SEM, n=6; Student's t test).

FIGS. 13A1 to 13A5 and illustrates cell surface expression of CCR1 protein in cell lines MDA-MB-23, HS578T, SUM159, MCF-7, Jurkat cells by FACS analysis;

FIGS. 13B1 to 13B5 and illustrate cell surface expression of CCR3 in cell lines MDA-MB-23, HS578T, SUM159, MCF-7, Jurkat cells by FACS analysis;

FIGS. 13C1 to 13C5 illustrate cell surface expression of CCR5 protein in cell lines MDA-MB-23, HS578T, SUM159, MCF-7, Jurkat cells by FACS analysis;

FIG. 13D shows relative abundance of cell surface expression of CCR1, CCR3 and CCR5 of cell lines MDA-MB-23, HS578T, SUM159, MCF-7, Jurkat cells as determined by FACS analysis;

FIG. 14A illustrates immunohistochemical staining of CCR5 in breast cancer tissue, showing staining was localized primarily to the breast cancer epithelial cell compared with normal breast tissue;

FIG. 14B illustrates immunohistochemical staining of CCR5 in normal breast tissue, showing staining of CCR5 in normal breast tissue is very low, demonstrating lack of CCR5 in normal breast compared with breast tumor;

FIG. 14C Immunohistochemical staining of CCR5 in breast cancer tissue, demonstrating CCR5 immunohistochemical staining being localized primarily to the breast cancer epithelial cell compared with normal breast tissue; and FIG. 14D shows immunohistochemical staining of CCR5 in normal breast tissue, demonstrating lack of CCR5 in normal breast tissue (of different patients than shown in FIG. 14B) compared with breast tumor.

DETAILED DESCRIPTION OF THE INVENTION

Figure 1A:
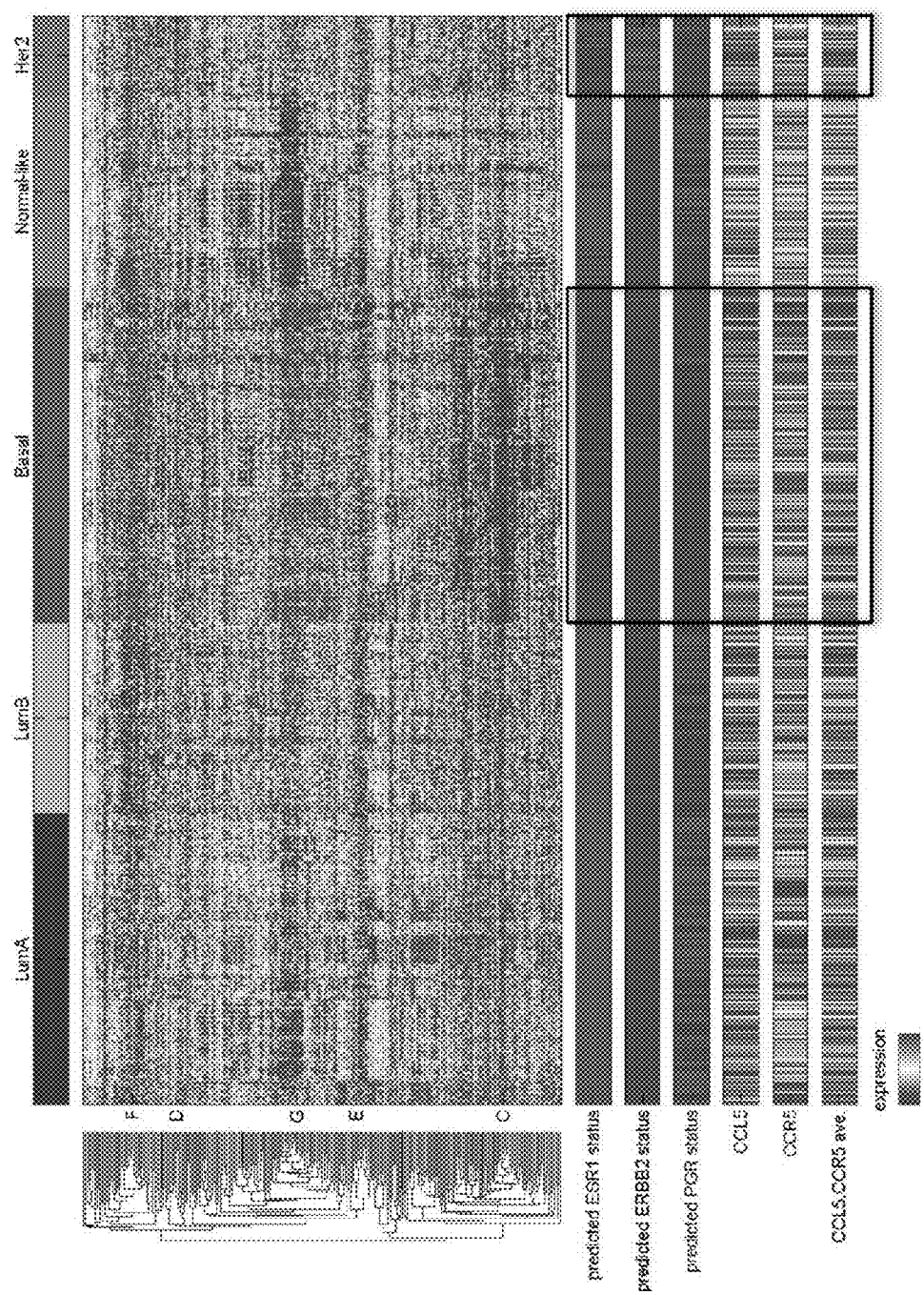
FIG. 1A illustrates a heatmap of the expression of CCL5 and its receptor CCR5 in samples from patients with breast cancer divided by molecular subtype (luminal A, luminal B, basal, normal-like, and Her-2) based on their gene expression pattern.

Chemokine (C-C motif) ligand 5 ("CCL5"), also known as RANTES (an acronym for Regulated on Activation, Normal T cell Expressed and Secreted) is a protein which in humans is encoded by the CCL5 gene. Its receptor, C-C chemokine receptor type 5 ("CCR5" or "CD195") is a protein found on the white blood cells. CCR5 is the main coreceptor used by macrophage (M)-tropic strains of human immunodeficiency virus type 1 (HIV-1) and HIV-2, which are responsible for viral transmission. CCR5 therefore plays an essential role in HIV pathogenesis. A number of inflammatory CC-chemokines, including MIP-1 alpha, MIP-1 beta, RANTES, MCP-2, and HCC-1[9-74] act as CCR5 agonists, while MCP-3 is a natural antagonist of the receptor. CCR5 is mainly expressed in memory T-cells, macrophages, and immature dendritic cells, and is upregulated by proinflammatory cytokines.

Classes of antiretroviral medications with activity against HIV include nucleoside analogs, nonnucleoside reverse transcriptase inhibitors, protease inhibitors, fusion inhibitors, integrase inhibitors, and CCR5 receptor antagonists. CCR5 antagonists exert their antiviral activity against HIV by blocking entry of CCR5-tropic viruses into the CD4 T cell. As a result, CCR5 antagonists have historically only been associated with expression in inflammatory cells in the immune system.

Prior to the present disclosure, the roles of the chemokine CCL5 and its receptor CCR5 in cancer progression were unclear. As disclosed herein, patients with cancers expressing CCL5 and its receptor CCR5, present new drug targets. As disclosed herein, treating cancers that expressed CCL5 and its receptor CCR5 with drugs that blocking their activities respecting CCL5 and its receptor CCR5 selectively affect these cancer cells that express mutant chemokine CCL5 and its receptor CCR5. In one embodiment, a subpopulation of human breast cancer cell lines were found to express CCR5 displayed a functional response to CCL5.

A microarray analysis conducted on 2,254 human breast cancer specimens found increased expression of CCL5 and its receptor CCR5, but not CCR3, in the basal and HER-2 genetic subtypes. The subpopulation of human breast cancer cell lines found to express CCR5 displayed a functional response to CCL5. Also, oncogene transformation induced CCR5 expression, and the subpopulation of cancer cells that expressed functional CCR5 also displayed increased invasiveness.

In one embodiment, the CCR5 antagonists developed initially to block CCR5 HrV co-receptor function, reduced in vitro invasion of cancer cells without affecting cell proliferation or viability. In one embodiment, the CCR5 antagonists include maraviroc and vicriviroc. In one embodiment, the subpopulation of cancer cells that expressed functional CCR5 include basal breast cancer cells. In one embodiment, the CCR5 antagonists include maraviroc and vicriviroc reduced in vitro invasion of basal cancer cells without affecting the basal cancer cell proliferation or viability. In one embodiment, the CCR5 antagonists include maraviroc and vicriviroc reduced in vivo invasion of basal cancer cells without affecting the basal cancer cell proliferation or viability.

However, as disclosed herein, CCL5 and its receptor CCR5 were found to be expressed in cancer cells, including breast cancer cells, were also found to regulate cancer metastasis, spread of cancer from its primary site to other sites in the body (e.g., brain, liver, lung). Moreover, it was found that blocking the CCR5 receptor with CCR5 antagonists, such as Maraviroc and Vicriviroc, prevented migration and spread of the cancer from its primary site to other sites in the body.

As described herein, CCR5 and CCL5 were found to play a key role in cancer invasiveness. For example, it was shown that CCR5 antagonists slowed down and/or prevented the invasion of secondary sites in the body by cancers that express CCL5 and/or its receptor CCR5, demonstrating usefulness of CCR5 antagonists as viable adjuvant therapy for reducing the risk of metastasis in cancer patients, including patients having basal breast cancer molecular subtype that express CCL5 and/or its receptor CCR5.

Cell receptor status can determine whether or not a cancer patient is susceptible to a particular anti-cancer treatment. For example, patients diagnosed with the basal breast cancer subtype, where the basal breast cancer subtype does not express the androgen or estrogen receptors or HER-2, current treatment choices, including chemotherapy, radiation, or surgery, are not only the only choices for these patients, but all show poor outcomes for these patients. Notwithstanding the fact that currently there are no other effective therapies available to them, the patients with this variant of basal breast cancer are further disadvantaged by the fact that this variant of basal breast cancer is also typically associated with metastasis. New cancer treatments present the only hope of cancer free survival for these patients. Accordingly, an urgent need exists for a specific targeted therapy for the basal breast cancer subtype.

In one aspect the present invention relates to the use of CCR5 modulators to treat, prevent, or manage a neoplasm or metastasis of the neoplasm. In one embodiment the neoplasm is cancer. Exemplary cancers and related disorders that can be treated, prevented, or managed in accordance with the exemplary embodiments of the methods of the present invention include, but are not limited to, leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In one embodiment, antagonists of CCR5 are used to treat CCR5-expressing neoplasm or metastasis of the CCR5-expressing neoplasm. In one embodiment, antagonists of CCR5 are used to prevent the neoplasm or metastasis of said neoplasm. In one embodiment, antagonists of CCR5 are used to manage the neoplasm metastasis of said neoplasm. In one embodiment, antagonists of CCR5 are used slow the progression of the CCR5-expressing neoplasm or metastasis of the CCR5-expressing neoplasm. In one embodiment, antagonists of CCR5 are used to delay metastasis of the CCR5-expressing neoplasm.

In one embodiment, antagonists of CCR5 that are suitable for use in accordance with the exemplary methods of the present invention include, but are not limited to, the chemical compounds that are described in U.S. Pat. No. 6,667,314 by Perros et al. The chemical compounds of Perros et al. and all formulations and dosage forms including them are incorporated by reference into the present application. Preferred examples of the compounds by Perros et al. include:

4,4-difluoro-N-[(1S)-3-[(1R,5S)-3-(3-methyl-5-propan-2-yl-1,2,4-triazol-4-yl)-8-azabicyclo[3.2.1]octan-8-yl]-1-phenylpropyl]cyclohexane-1-carboxamide ("Maraviroc");

N-(1S)-3-3-(3-Isopropyl-5-methyl-4H-1,2,4-triazol-4-yl)-exo-8-azabicyclo[3.2.1]oct-8-yl-1-phenylpropylcyclobutanecarboxamide;

N-(1S)-3-3-(3-Isopropyl-5-methyl-4H-1,2,4-triazol-4-yl)-exo-8-azabicyclo[3.2.1]oct-8-yl-1-phenylpropylcyclopentanecarboxamide;

N-(1S)-3-3-3-(3-Isopropyl-5-methyl-4H-1,2,4-triazol-4-yl)-exo-8-azabicyclo[3.2.1]oct-8-yl-1-phenylpropyl-4,4,4-trifluorobutanamide;

N-(1S)-3-3-(3-Isopropyl-5-methyl-4H-1,2,4-triazol-4-yl)-exo-8-azabicyclo[3.2.1]oct-8-yl-1-phenylpropyl-4,4-difluorocyclohexanecarboxamide;

N-(1S)-3-3-(3-Isopropyl-5-methyl-4H-1,2,4-triazol-4-yl)-exo-8-azabicyclo[3.2.1]oct-8-yl-1(3-fluorophenyl)propyl-4,4-difluorocyclohexanecarboxamide; and pharmaceutically acceptable salts or solvates thereof.

In one embodiment, the modulators of CCR5 receptor that are suitable for treating the neoplasm or metastasis of said neoplasm; or preventing the neoplasm or metastasis of said neoplasm; or managing the neoplasm metastasis of said neoplasm; or slowing the progression of the neoplasm or metastasis of said neoplasm; or delaying the neoplasm or metastasis of said neoplasm; include, but are not limited to the chemical compounds that are described in U.S. Pat. No. 6,586,430 by Armour et al. The chemical compounds of Armour et al. and all formulations or dosage forms including them are incorporated by reference into the present application. Preferred examples of the compounds by Armour et al. include:

N-{3-[3-exo-(2-Methyl-1H-benzimidazol-1-yl)-8-azabicyclo[3.2.1]oct-8-yl]-1-phenylpropyl}cyclobutanecarboxamide;

N-{(1S)-3-[3-exo-2-Methyl-1H-benzimidazol-1-yl)-8-azabicyclo[3.2.1]oct-8-yl]-1-phenylpropyl}cyclobutanecarboxamide;

N-{(1S)-3-[3-endo-(2-Methyl-1H-benzimidazol-1-yl)-8-azabicyclo[3.2.1]oct-8-yl]-1-phenylpropyl}cyclobutanecarboxamide;

N-{(1S)-3-[3-exo-(2-Methyl-1H-benzimidazol-1-yl)-8-azabicyclo[3.2.1]oct-8-yl]-1-phenylpropyl}tetrahydro-2H-pyran-4-carboxamide;

1-Acetyl-N-{(1S)-3-[3-exo-(2-methyl-1H-benzimidazol-1-yl)-8-azabicyclo[3.2.1]oct-8-yl]-1-phenylpropyl}3-azetidine carboxamide;

1-Hydroxy-N-{(1S)-3-[3-exo-2-methyl-1H-benzimidazol-1-yl)-8-azabicyclo[3.2.1]oct-8-yl]-1-phenylpropyl}cyclopentanecarboxamide;

2-Methyl-N-{(1S)-3-[3-exo-(2-methyl-1H-benzimidazol-1-yl)-8-azabicyclo[3.2.1]oct-8-yl]-1-phenylpropyl}cyclopropanecarboxamide;

2-Cyclopropyl-N-{1S)-3-[3-exo-(2-methyl-1H-benzimidazol-1-yl)-8-azabicyclo[3.2.1]oct-8-yl]-1-phenylpropyl}acetamide;

N-{(1S)-3-[3-exo-(2-methyl-1H-benzimidazol-1-yl)-8-azabicyclo[3.2.1]oct-8-yl]-1-phenylpropyl}tetrahydro-3-furancarboxamide;

3,3,3-Trifluoro-N-{(1S)-3-[3-exo-(2-methyl-1H-benzimidazol-1-yl)-8-azabicyclo[3.2.1]oct-8-yl]-1-phenylpropyl}propanamide;

N-{(1S)-3-[3-exo-(2-Methyl-1H-benzimidazol-1-yl)-8-azabicyclo[3.2.1]oct-8-yl]-1-phenylpropyl}tetrahydro-2-furancarboxamide;

1-(Acetylamino)-N-{(1S)-3-[3-exo-(2-methyl-1H-benzimidazol-1-yl)-8-azabicyclo[3.2.1]oct-8-yl]-1-phenylpropyl}cyclopentanecarboxamide;

N-{(1S)-3-[3-exo-(2-Methyl-1H-benzimidazol-1-yl)-8-azabicyclo[3.2.1]oct-8-yl]-1-phenylpropyl}acetamide;

1-Methoxy-N-{(1S)-3-[3-exo-(2-methyl-1H-benzimidazol-1-yl)-8-azabicyclo[3.2.1]oct-8-yl]-1-phenylpropyl}cyclopentanecarboxamide;

1-Amino-N-{(1S)-3-[3-exo-(2-methyl-1H-benzimidazol-1-yl)-8-azabicyclo[3.2.1]oct-8-yl]-1-phenylpropyl}cyclopentanecarboxamide;

1-Methyl-N-{(1S)-3-[3-exo-(2-methyl-1H-benzimidazol-1-yl)-8-azabicyclo[3.2.1]oct-8-yl]-1-phenylpropyl}-2-oxo-4-pyrrolidinecarboxamide;

1-Acetyl-N-{(1S)-3-[3-endo-(2-methyl-1H-benzimidazol-1-yl)-8-azabicyclo[3.2.1]oct-8-yl]-1-phenylpropyl)3-azetidinecarboxamide;

N-{(1S)-3-[3-endo-(2-Methyl-1H-benzimidazol-1-yl)-8-azabicyclo[3.2.1]oct-8-yl]-1-phenylpropyl}acetamide;

N-{(1S)-3-[6-(2-Methyl-1H-benzimidazol-1-yl)-3-azabicyclo[3.1.0]hex-3-yl]-1-phenylpropyl}cyclobutanecarboxamide;

2-Cyclopropyl-N-{(1S)-3-[3-exo-(3-{4-[(methylsulfonyl)amino]benzyl}-1,2,4-oxadiazol-5-yl)-8-azabicyclo[3.2.1]oct-8-yl]-1-phenylpropyl}acetamide;

N-{(1S)-3-[7-exo-(2-Methyl-1H-benzimidazol-1-yl)-3-oxa-9-azabicyclo[3.3.1]non-9-yl]-1-phenylpropyl}cyclobutanecarboxamide;

2-Cyclopropyl-N-{(1S)-3-[7-exo-(2-methyl-1H-benzimidazol-1-yl)-3-oxa-9-azabicyclo[3.3.1]non-9-yl]-1-phenylpropyl}acetamide;

3,3,3-Trifluoro-N-{(1S)-3-[7-exo-(2-methyl-1H-benzimidazol-1-yl)-3-oxa-9-azabicyclo[3.3.1]non-9-yl]-1-phenylpropyl}propanamide;

N-{(1S)-3-[7-endo-(2-Methyl-1H-benzimidazol-1-yl)-3-oxa-9-azabicyclo[3.3.1]non-9-yl]-1-phenylpropyl}cyclobutanecarboxamide;

2-Cyclopropyl-N-{(1S)-3-[7-endo-(2-methyl-1H-benzimidazol-1-yl)-3-oxa-9-azabicyclo[3.3.1]non-9-yl]-phenylpropyl}acetamide;

N-{(1S)-3-[7-exo-(2-Methyl-1H-benzimidazol-1-yl)-3-thia-9-azabicyclo[3.3.1]non-9-yl]-1-phenylpropyl}cyclobutanecarboxamide;

2-Cyclopropyl-N-[(1S)-3-(3-endo-{[2-(4-fluorophenyl)acetyl]amino}-8-azabicyclo[3.2.1]oct-8-yl)-1-phenylpropyl]acetamide;

N-[(1S)-3-(3-{[3-endo-(4-Fluorophenyl)ppropanoyl]amino}-8-azabicyclo[3.2.1]oct-8-yl)-1-phenylpropyl]cyclobutanecarboxamide;

N-[(1S)-3-(3-{[3-exo-(4-Fluorophenyl)prpropanoyl]amino}-8-azabicyclo[3.2.1]oct-8-yl)-1-phenylpropyl]cyclobutanecarboxamide;

2-Cyclopropyl-N-[(1S)-3-(3-exo-{[2-(4-fluorophenyl)acetyl]amino}-8-azabicyclo[3.2.1]oct-8-yl)-1-phenylpropyl]acetamide;

N-{(1S)-3-[3-exo-(2-Methyl-1H-benzimidazol-1-yl)-8-azabicyclo[3.2.1]oct-8-yl]-1-phenylpropyl)}1-propionyl-3-azetidinecarboxamide;

N-{(1S)-3-[3-endo-(2-Methyl-1H-benzimidazol-1-yl)-8-azabicyclo[3.2.1]oct-8-yl]-1-phenylpropyl}tetrahydro-3-furancarboxamide;

N-{(1S)-3-[3-endo-(2-Methyl-1H-benzimidazol-1-yl)-8-azabicyclo[3.2.1]oct-8-yl]-1-phenylpropyl}tetrahydro-2H-pyran4-carboxamide;

N-{(1S)-3-[3-endo-(2-Methyl-1H-benzimidazol-1-yl)-8-azabicyclo[3.2.1]oct-8-yl]-1-phenylpropyl}tetrahydro-2-furancarboxamide;

1-Acetyl-N-{(1S)-3-[3-endo-(1H-benzimidazol-1-yl)-8-azabicyclo[3.2.1]oct-8-yl]-1-phenylpropyl}-3-azetidinecarboxamide;

N-{(1S)-3-[3-endo-(1H-Benzimidazol-1-yl)-8-azabicyclo[3.2.1]oct-8-yl]-1-phenylpropyl}-1-propionyl-3-azetidinecarboxamide;

Methyl 3-[({(1S)-3-[3-exo-(2-methyl-1H-benzimidazol-1-yl)-8-azabicyclo[3.2.1]oct-8-yl]-1-phenylpropyl}amino)carbonyl]-1-azetidinecarboxylate;

N-{(1S)-3-[3-endo-(2-Methyl-1H-benzimidazol-1-yl)-8-azabicyclo-[3.2.1]oct-8-yl]-1-phenylpropyl}-1-propionyl-3-azetidinecarboxamide 1-Acetyl-N-{(1S)-3-[3-endo-(2-methyl-1H-benzimidazol-1-yl)-8-azabicyclo[3.2.1]oct-8-yl]-1-phenylpropyl}-2-azetidinecarboxamide;

2-[Acetyl(methyl)amino]-N-{(1S)-3-[3-endo-(2-methyl-1H-benzimidazol-1-yl)-8-azabicyclo[3.2.1]oct-8-yl]-1-phenylpropyl}acetamide;

3-[Acetyl(methyl)amino]-N-{(1S)-3-[3-endo-(2-methyl-1H-benzimidazol-1-yl)-8-azabicyclo[3.2.1]oct-8-yl]-1-phenylpropyl}propanamide;

2-Methoxy-N-{(1S)-3-[3-endo-(2-methyl-1H-benzimidazol-1-yl)-8-azabicyclo[3.2.1]oct-8-yl]-1-phenylpropyl}acetamide;

3-Methoxy-N-{(1S)-3-[3-endo-2-methyl-1H-benzimidazol-1-yl)-8-azabicyclo[3.2.1]oct-8-yl]-1-phenylpropyl}propanamide;

1-Acetyl-N-{(1S)-3-[3-endo-(2-methyl-1H-benzimidazol-1-yl)-8-azabicyclo[3.2.1]oct-8-yl]-1-phenylpropyl}-3-pyrrolidinecarboxamide;

1-Methyl-N-{(1S)-3-[3-endo-(2-methyl-1H-benzimidazol-1-yl)-8-azabicyclo[3.2.1]oct-8-yl]-1-phenylpropyl}-2-oxo-4-pyrrolidinecarboxamide;

1-Acetyl-N-{(1S)-3-[3-exo-(2-ethyl-1H-benzimidazol-1-yl)-8-azabicyclo[3.2.1]oct-8-yl]-1-phenyylpropyl}-3-azetidinecarboxamide;

N-{(1S)-3-[3-exo-(2-Ethyl-1H-benzimidazol-1-yl)-8-azabicyclo[3.2.1]oct-8-yl]-1-phenylpropyl}-1-propionyl-3-azetidinecarboxamide;

1-Acetyl-N-((1S)-1-phenyl-3-{3-exo-[2-(trifluoromethyl)-1H-benzimidazol-1-yl]-8-azabicyclo[3.2.1]oct-8-yl}propyl)-3-azetidinecarboxamide;

N-((1S)-1-Phenyl-3-{3-exo-[2-(trifluoromethyl)-1H-benzimidazol-1-yl]-8-azabicyclo[3.2.1]oct-8-yl}propyl)-1-propionyl-3-azetidinecarboxamide;

N-((1S)-1-Phenyl-3-{3-exo[2-(trifluoromethyl)-1H-benzimidazol-1-yl]-8-azabicyclo[3.2.1]oct-8-yl}propyl)acetamide;

2-[Acetyl(methyl)amino]-N-((1S)-1-phenyl-3-{3-exo-[2-(trifluoromethyl)-1H-benzimidazol-1-yl]-8-azabicyclo[3.2.1]oct-8-yl}propyl)acetamide;

1-Acetyl-N-{(1S)-3-[3-exo-(1H-benzimidazol-1-yl)-8-azabicyclo[3.2.1]oct-8-yl]-1-phenylpropyl}-3-azetidinecarboxamide;

N(1S)-3-[3-exo-(1H-Benzimidazol-1-yl)-8-azabicyclo[3.2.1]oct-8-yl]-1-phenylpropyl}-1-propionyl-3-azetidinecarboxamide;

1-acetyl-N(1S)-3-[3-exo-(5-fluoro-1H-benzimidazol-1-yl)-8-azabicyclo[3.2.1]oct-8-yl]-1-phenylpropyl)3-azetidinecarboxamide;

N-{(1S)-3-[3-exo-(5-Fluoro-1H-benzimidazol-1-yl)-8-azabicyclo[3.2.1]oct-8-yl]-1-phenylpropyl}-1-propionyl-3-azetidinecarboxamide;

1-Acetyl-N-{(1S)-3-[3-exo-(5-fluoro-2-methyl-1H-benzimidazol-1-yl)-8-azabicyclo[3.2.1]oct-8-yl]-1-phenylpropyl}3-azetidinecarboxamide;

N-{(1S)-3-[3-exo-(5-Fluoro-2-methyl-1H-benzimidazol-1-yl)-8-azabicyclo[3.2.1]oct-8-yl]-1-phenylpropyl}-1-propionyl-3-azetidinecarboxamide;

N-{(1S)-3-[3-exo-(2-methyl-1H-benzimidazol-1-yl)-8-azabicyclo[3.2.1]oct-8-yl]-1-phenylpropyl}-3-azetidinecarboxamide;

1-methyl-N-{(1S)-3-[3-exo-(2-methyl-1H-benzimidazol-1-yl)-8-azabicyclo[3.2.1]oct-8-yl]-1-phenylpropyl}-3-azetidinecarboxamide;

(2S)-1-acetyl-N-{(1S)-3-[3-exo-(2-methyl-1H-benzimidazol-1-yl)-8-azabicyclo[3.2.1]oct-8-yl]-1-phenylpropyl}-2-azetidinecarboxamide;

(2R)-1-acetyl-N-{(1S)-3-[3-exo-(2-methyl-1H-benzimidazol-1-yl)-8-azabicyclo[3.2.1]oct-8-yl]-1-phenylpropyl}-2-azetidinecarboxamide;

2-[acetyl(methyl)amino]-N-{(1S)-3-[3-exo-(2-methyl-1H-benzimidazol-1-yl)-8-azabicyclo[3.2.1]oct-8-yl]-1-phenylpropyl}acetamide;

3-[acetyl(methyl)amino]-N-{(1S)-3-[3-exo-(2-methyl-1H-benzimidazol-1-yl)-8-azabicyclo[3.2.1]oct-8-yl]-1-phenylpropyl}propanamide;

1-acetyl-N-{(1S)-3-[3-exo-(2-methyl-1H-benzimidazol-1-yl)-8-azabicyclo[3.2.1]oct-8-yl]-1-phenylpropyl}-3-pyrrolidinecarboxamide;

N-{(1S)-3-[3-exo-(2-methyl-1H-benzimidazol-1-yl)-8-azabicyclo[3.2.1]oct-8-yl]-1-phenylpropyl}-1-(trifluoromethyl)cyclopropanecarboxamide;

2-methoxy-N-{(1S)-3-[3-exo-(2-methyl-1H-benzimidazol-1-yl)-8-azabicyclo[3.2.1]oct-8-yl]-1-phenylpropyl}acetamide;

3-methoxy-N-{(1S)-3-[3-exo-(2-methyl-1H-benzimidazol-1-yl)-8-azabicyclo[3.2.1]oct-8-yl]-1-phenylpropyl}propanamide;

1-Acetyl-N-{(1S)-3-[3-exo-(4-fluoro-2-methyl-1H-benzimidazol-1-yl)-8-azabicyclo[3.2.1]oct-8-yl]-1-phenylpropyl}-3-azetidinecarboxamide;

N-{(1S)-3-[3-exo-(4-Fluoro-2-methyl-1H-benzimidazol-1-yl)-8-azabicyclo[3.2.1]oct-8-yl]-1-phenylpropyl}-3-azetidinecarboxamide;

1-Methyl-N-{(1S)-3-[3-exo-(4-fluoro-2-methyl-1H-benzimidazol-1-yl)-8-azabicyclo[3.2.1]oct-8-yl]-1-phenylpropyl}-3-azetidinecarboxamide;

N-{(1S)-3-[3-exo-(4-Fluoro-2-methyl-1H-benzimidazol-1-yl)-8-azabicyclo[3.2.1]oct-8-yl]-1-phenylpropyl}-1-propionyl-3-azetidinecarboxamide;

2-Methoxy-N-{(1S)-3-[3-exo-(4-Fluoro-2-methyl-1H-benzimidazol-1-yl)-8-azabicyclo[3.2.1]oct-8-yl]-1-phenylpropyl}acetamide;

N-{(1S)-3-[3-exo-(4-Fluoro-2-Methyl-1H-benzimidazol-1-yl)-8-azabicyclo[3.2.1]oct-8-yl]-1-phenylpropyl}acetamide;

3-Methoxy-N-{(1S)-3-[3-exo-(4-fluoro-2-methyl-1H-benzimidazol-1-yl)-8azabicyclo[3.2.1]oct-8-yl]-1-phenylpropyl}propanamide;

2-[Acetyl(methyl)amino]-N-{(1S)-3-[3-exo-(4-fluoro-2-methyl-1H-benzimidazol-1-yl)-8-azabicyclo[3.2.1]oct-8-yl]-1-phenylpropyl}acetamide;

3-[Acetyl(methyl)amino]-N-{(1S)-3-[3-exo-(4-fluoro-2methyl-1H-benzimidazol-1-yl)-8-azabicyclo[3.2.1]oct-8-yl]-1-phenylpropyl}propanamide;

N-{(1S)-3-[3-exo-(4-fluoro-1H-benzimidazol-1-yl)-8-azabicyclo[3.2.1]oct-8-yl]-1-phenylpropyl}-3-methyl-3-oxetanecarboxamide;

3-Ethyl-N-{(1S)-3-[3-exo-(4-fluoro-2-methyl-1H-benzimidazol-1-yl)-8-azabicyclo[3.2.1]oct-8-yl]-1-phenylpropyl}-3-oxetanecarboxamide;

N-{(1S)-3-[3-exo-(4-Fluoro-2-methyl-1H-benzimidazol-1-yl)-8-azabicyclo[3.2.1]oct-8-yl]-1-phenylpropyl}-3-oxetanecarboxamide;

3-Ethyl-N-{(1S)-3-[3-exo-(4-fluoro-1H-benzimidazol-1-yl)-8-azabicyclo[3.2.1]oct-8-yl]-1-phenylpropyl}-3-oxetanecarboxamide;

N-{(1S)-3-[3-exo-(4-Fluoro-1H-benzimidazol-1-yl)-8-azabicyclo[3.2.1]oct-8-yl]-1-phenylpropyl}-3-methyl-3-oxetanecarboxamide;

N-{(1S)-3-[3-exo-(4-Fluoro-1H-benzimidazol-1-yl)-8-azabicyclo[3.2.1]oct-8-yl]-1-phenylpropyl}-3-oxetanecarboxamide;

N-{(1S)-3-[3-exo-(4-Fluoro-1H-benzimidazol-1-yl)-8-azabicyclo[3.2.1]oct-8-yl]-1-phenylpropyl}-3-azetidinecarboxamide;

N-{(1S)-3-[3-exo-(4-Fluoro-1H-benzimidazol-1-yl)-8-azabicyclo[3.2.1]oct-8-yl]-1-phenylpropyl}-1-methyl-3-azetidinecarboxamide;

1-Acetyl-N-{(1S)-3-[3-exo-(4-fluoro-1H-benzimidazol-1-yl)-8-azabicyclo[3.2.1]oct-8-yl]-1-phenylpropyl}-3-azetidinecarboxamide;

N-{(1S)-3-[3-exo-(4-Fluoro-1H-benzimidazol-1-yl)-8-azabicyclo[3.2.1]oct-8-yl]-1-phenylpropyl}-1-propionyl-3-azetidinecarboxamide;

N-{(1S)-3-[3-exo-(4-Fluoro-1H-benzimidazol-1-yl)-8-azabicyclo[3.2.1]oct-8-yl]-1-phenylpropyl}-2-methoxyacetamide;

N-{(1S)-3-[3-exo-(4-Fluoro-1H-benzimidazol-1-yl)-8-azabicyclo[3.2.1]oct-8-yl]-1-phenylpropyl}acetamide;

N{-1S)-3-[3-exo-(4-fluoro-1H-benzimidazol-1-yl)-8-azabicyclo[3.2.1]oct-8-yl]-1-phenylpropyl}-3-methoxypropanamide;

2-[Acetyl(methyl)amino]-N-{(1S)-3-[3-exo-(4-fluoro-1H-benzimidazol-1-yl)-8-azabicyclo[3.2.1]oct-8-yl]-1-phenylpropyl}acetamide;

3-[Acetyl(methyl)amino]-N-{(1S)-3-[3-exo-(4-fluoro-1H-benzimidazol-1-yl)-8-azabicyclo[3.2.1]oct-8-yl]-1-phenylpropyl}propanamide; and pharmaceutical acceptable salts thereof.

In yet another embodiment, modulators of CCR5 receptor that are suitable for treating neoplasm or metastasis of the neoplasm; or preventing the neoplasm or metastasis of the neoplasm; or managing the neoplasm metastasis of the neoplasm; or slowing the progression of the neoplasm or metastasis of the neoplasm; or delaying the neoplasm or metastasis of said neoplasm; include, but are not limited to the chemical compounds that are described in U.S. Pat. Nos. 6,689,765 and 7,384,944 both by Baroudy et al. The chemical compounds of Baroudy et al. and all formulations or dosage forms including them are incorporated by reference into the present application. A preferred example of the compounds by Baroudy el al. includes: (4,6-dimethylpyrimidin-5-yl)-[4-[(3S)-4-[(1R)-2-methoxy-1-[4-(trifluoromethyl)phenyl]ethyl]-3-methylpiperazin-1-yl]-4-methylpiperidin-1-yl]methanone (Vicriviroc, also previously named SCH 417690 and SCH-D), which has an alternative IUPAC name of 5-({4-[(3S)-4-{2-methoxy-1-[4-(trifluoromethyl)phenyl]ethyl}-3-methylpiperazin-1-yl]-4-methylpiperidin-1-yl}carbonyl)-4,6-dimethylpyrimidine; and pharmaceutically acceptable salts or solvates thereof.

In one aspect, the present invention provides a method of determining whether a subject has cancer or is at risk for developing cancer and/or is at risk for developing metastasis of. In one embodiment, the method includes obtaining a biological sample from a subject having or suspected of having cancer and assessing the level of expression of CCR5 and/or of at least one of CCR5 ligands in the biological sample. In one embodiment, the expression level of CCR5 and/or of at least one of CCR5 ligands in the biological sample is compared to an expression level of CCR5 and/or of at least one of CCR5 ligands in a control sample. In one embodiment, if the expression level of CCR5 and/or of at least one of CCR5 ligands in the biological sample is higher than the level of expression of CCR5 and/or of at least one of CCR5 ligands in the control sample, then the subject is diagnosed as likely to have cancer. In one embodiment, if the expression level of CCR5 and/or of at least one of CCR5 ligands in the biological sample is higher than the level of expression of CCR5 and/or of at least one of CCR5 ligands in the control sample, then the subject is diagnosed as at increased risk for developing cancer. In one embodiment, if the expression level of CCR5 and/or of at least one of CCR5 ligands in the biological sample is higher than the level of expression of CCR5 and/or of at least one of CCR5 ligands in the control sample, then the subject is diagnosed as at increased risk for developing cancer metastasis.

The term "subject" as used herein is intended to include animals. In particular embodiments, the subject is a mammal, a human or nonhuman primate, a dog, a cat, a horse, a cow or a rodent.

In another aspect, the present invention provides a method for molecular classification of cancer based on a level of expression of CCR5 and/or of at least one of CCR5 ligands in the biological sample of the cancer. In one embodiment, the method for molecular classification of cancer comprises (a) obtaining a biological sample of cancer from subject; (b) determining level of expression of CCR5 and/or level of expression of at least one of CCR5 ligands in the biological sample; and (c) if the level of expression of CCR5 and/or level of expression of at least one of CCR5 ligands determined in step (b) is higher than the level of expression of CCR5 and/or of at least one of CCR5 ligands in a control sample, then the cancer is classified as CCR5-expressing cancer. In one embodiment, a cancer subject whose cancer has been classified as CCR5-expressing cancer is diagnosed as likely at risk for developing metastasis of the cancer. In one embodiment, the cancer is breast cancer. In one embodiment, the cancer is prostate cancer. In one embodiment, the cancer is selected from the group consisting of leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In another aspect, the present invention provides for a method of treating, preventing, or managing a CCR-5 expressing neoplasm or a metastasis of the CCR5-expressing neoplasm in a subject. In one embodiment, the a method of treating or managing a CCR-5 expressing neoplasm or a metastasis of the CCR5-expressing neoplasm in subject having the CCR5-expressing neoplasm or at risk for developing metastasis of the CCR5-expressing neoplasm, comprises administering to the subject a CCR5 modulator. In one embodiment, the CCR5 modulator comprises a CCR5 antagonist. In one embodiment, the CCR5 antagonist comprises 4,4-difluoro-N-[(1S)-3-[(1R,5S)-3-(3-methyl-5-propan-2-yl-1,2,4-triazol-4-yl)-8-azabicyclo[3.2.1]octan-8-yl]-1-phenylpropyl]cyclohexane-1-carboxamide ("Maraviroc"). In one embodiment, the CCR5 modulator comprises a CCR5 antagonist. In one embodiment, the CCR5 antagonist comprises (4,6-dimethylpyrimidin-5-yl)-[4-[(3S)-4-[(1R)-2-methoxy-1-[4-(trifluoromethyl)phenyl]ethyl]-3-methylpiperazin-1-yl]-4-methylpiperidin-1-yl]methanone ("Vicriviroc"). In one embodiment, the CCR5 antagonist antagonist is selected from the group consisting of 4,4-difluoro-N-[(1S)-3-[(1R,5S)-3-(3-methyl-5-propan-2-yl-1,2,4-triazol-4-yl)-8-azabicyclo[3.2.1]octan-8-yl]-1-phenylpropyl]cyclohexane-1-carboxamide ("Maraviroc") and (4,6-dimethylpyrimidin-5-yl)-[4-[(3S)-4-[(1R)-2-methoxy-1-[4-(trifluoromethyl)phenyl]ethyl]-3-methylpiperazin-1-yl]-4-methylpiperidin-1-yl]methanone ("Vicriviroc").

In one embodiment, suitable CCR5 antagonist is selected from the group consisting of:
4,4-difluoro-N-[(1S)-3-[(1R,5S)-3-(3-methyl-5-propan-2-yl-1,2,4-triazol-4-yl)-8-azabicyclo[3.2.1]octan-8-yl]-1-phenylpropyl]cyclohexane-1-carboxamide ("Maraviroc");
N-(1S)-3-3-(3-Isopropyl-5-methyl-4H-1,2,4-triazol-4-yl)-exo-8-azabicyclo[3.2.1]oct-8-yl-1-phenylpropylcyclobutanecarboxamide;
N-(1S)-3-3-(3-Isopropyl-5-methyl-4H-1,2,4-triazol-4-yl)-exo-8-azabicyclo[3.2.1]oct-8-yl-1-phenylpropylcyclopentanecarboxamide;
N-(1S)-3-3-(3-Isopropyl-5-methyl-4H-1,2,4-triazol-4-yl)-exo-8-azabicyclo[3.2.1]oct-8-yl-1-phenylpropyl-4,4,4-trifluorobutanamide;
N-(1S)-3-3-(3-Isopropyl-5-methyl-4H-1,2,4-triazol-4-yl)-exo-8-azabicyclo[3.2.1]oct-8-yl-1-phenylpropyl-4,4-difluorocyclohexanecarboxamide;
N-(1S)-3-3-(3-Isopropyl-5-methyl-4H-1,2,4-triazol-4-yl)-exo-8-azabicyclo[3.2.1]oct-8-yl-1-(3-fluorophenyl)propyl-4,4-difluorocyclohexanecarboxamide; and pharmaceutically acceptable salts or solvates thereof.

In one embodiment, suitable CCR5 antagonist is selected from the group consisting of:
N-{3-[3-exo-(2-Methyl-1H-benzimidazol-1-yl)-8-azabicyclo[3.2.1]oct-8-yl]-1-phenylpropyl}cyclobutanecarboxamide;
N-{(1S)-3-[3-exo-(2-Methyl-1H-benzimidazol-1-yl)-8-azabicyclo[3.2.1]oct-8-yl]-1-phenylpropyl}cyclobutanecarboxamide;
N-{(1S)-3-[3-endo-(2-Methyl-1H-benzimidazol-1-yl)-8-azabicyclo[3.2.1]oct-8-yl]-1-phenylpropyl}cyclobutanecarboxamide;
N-{(1S)-3-[3-exo-(2-Methyl-1H-benzimidazol-1-yl)-8-azabicyclo[3.2.1]oct-8-yl]-1-phenylpropyl}tetrahydro-2H-pyran-4-carboxamide;
1-Acetyl-N-{(1S)-3-[3-exo-(2-methyl-1H-benzimidazol-1-yl)-8-azabicyclo[3.2.1]oct-8-yl]-1-phenylpropyl}3-azetidine carboxamide;
1-Hydroxy-N-{(1S)-3-[3-exo-(2-methyl-1H-benzimidazol-1-yl)-8-azabicyclo[3.2.1]oct-8-yl]-1-phenylpropyl}cyclopentanecarboxamide;
2-Methyl-N-{(1S)-3-[3-exo-(2-methyl-1H-benzimidazol-1-yl)-8-azabicyclo[3.2.1]oct-8-yl]-1-phenylpropyl}cyclopropanecarboxamide;
2-Cyclopropyl-N-{1S)-3-[3-exo-(2-methyl-1H-benzimidazol-1-yl)-8-azabicyclo[3.2.1]oct-8-yl]-1-phenylpropyl}acetamide;
N-{(1S)-3-[3-exo-(2-methyl-1H-benzimidazol-1-yl)-8-azabicyclo[3.2.1]oct-8-yl]-1-phenylpropyl}tetrahydro-3-furancarboxamide;
3,3,3-Trifluoro-N-{(1S)-3-[3-exo-(2-methyl-1H-benzimidazol-1-yl)-8-azabicyclo[3.2.1]oct-8-yl]-1-phenylpropyl}propanamide;
N-{(1S)-3-[3-exo-(2-Methyl-1H-benzimidazol-1-yl)-8-azabicyclo[3.2.1]oct-8-yl]-1-phenylpropyl}tetrahydro-2-furancarboxamide;
1-(Acetylamino)-N-{(1S)-3-[3-exo-(2-methyl-1H-benzimidazol-1-yl)-8-azabicyclo[3.2.1]oct-8-yl]-1-phenylpropyl}cyclopentanecarboxamide;
N-{(1S)-3-[3-exo-(2-Methyl-1H-benzimidazol-1-yl)-8-azabicyclo[3.2.1]oct-8-yl]-1-phenylpropyl}acetamide;
1-Methoxy-N-{(1S)-3-[3-exo-(2-methyl-1H-benzimidazol-1-yl)-8-azabicyclo[3.2.1]oct-8-yl]-1-phenylpropyl}cyclopentanecarboxamide;
1-Amino-N-{(1S)-3-[3-exo-(2-methyl-1H-benzimidazol-1-yl)-8-azabicyclo[3.2.1]oct-8-yl]-1-phenylpropyl}cyclopentanecarboxamide;
1-Methyl-N-{(1S)-3-[3-exo-(2-methyl-1H-benzimidazol-1-yl)-8-azabicyclo[3.2.1]oct-8-yl]-1-phenylpropyl}-2-oxo-4-pyrrolidinecarboxamide;
1-Acetyl-N-{(1S)-3-[-endo-(2-methyl-1H-benzimidazol-1-yl)-8-azabicyclo[3.2.1]oct-8-yl]-1-phenylpropyl)3-azetidinecarboxamide;
N-{(1S)-3-[3-endo-(2-Methyl-1H-benzimidazol-1-yl)-8-azabicyclo[3.2.1]oct-8-yl]-1-phenylpropyl}acetamide;
N-{(1S)-3-[6-(2-Methyl-1H-benzimidazol-1-yl)-3-azabicyclo[3.1.0]hex-3-yl]-1-phenylpropyl}cyclobutanecarboxamide;
2-Cyclopropyl-N-{(1S)-3-[3-exo-(3-{4-[(methylsulfonyl)amino]benzyl}-1,2,4-oxadiazol-5-yl)-8-azabicyclo[3.2.1]oct-8-yl]-1-phenylpropyl}acetamide;
N-{(1S)-3-[7-exo-(2-Methyl-1H-benzimidazol-1-yl)-3-oxa-9-azabicyclo[3.3.1]non-9-yl]-1-phenylpropyl}cyclobutanecarboxamide;
2-Cyclopropyl-N-{(1S)-3-[7-exo-(2-methyl-1H-benzimidazol-1-yl)-3-oxa-9-azabicyclo[3.3.1]non-9-yl]-1-phenylpropyl}acetamide;
3,3,3-Trifluoro-N-{(1S)-3-[7-exo-(2-methyl-1H-benzimidazol-1-yl)-3-oxa-9-azabicyclo[3.3.1]non-9-yl]-1-phenylpropyl}propanamide;
N-{(1S)-3-[7-endo-(2-Methyl-1H-benzimidazol-1-yl)-3-oxa-9-azabicyclo[3.3.1]non-9-yl]-1-phenylpropyl}cyclobutanecarboxamide;
2-Cyclopropyl-N-{(1S)-3-[7-endo-(2-methyl-1H-benzimidazol-1-yl)-3-oxa-9-azabicyclo[3.3.1]non-9-yl]-1-phenylpropyl}acetamide;
N-{(1S)-3-[7-exo-(2-Methyl-1H-benzimidazol-1-yl)-3-thia-9-azabicyclo[3.3.1]non-9-yl]-1-phenylpropyl}cyclobutanecarboxamide;
2-Cyclopropyl-N-[(1S)-3-(3-endo-{[2-(4-fluorophenyl)acetyl]amino}-8-azabicyclo[3.2.1]oct-8-yl)-1-phenylpropyl]acetamide;
N-[(1S)-3-(3-{[3-endo-(4-Fluorophenyl)ppropanoyl]amino}-8-azabicyclo[3.2.1]oct-8-yl)-1-phenylpropyl]cyclobutanecarboxamide;

N-[(1S)-3-(3-{[3-exo-(4-Fluorophenyl)prpropanoyl]amino}-8-azabicyclo[3.2.1]oct-8-yl)-1-phenylpropyl]cyclobutanecarboxamide;

2-Cyclopropyl-N-[(1S)-3-(3-exo-{[2-(4-fluorophenyl)acetyl]amino}-8-azabicyclo[3.2.1]oct-8-yl)-1-phenylpropyl]acetamide;

N-{(1S)-3-[3-exo-(2-Methyl-1H-benzimidazol-1-yl)-8-azabicyclo[3.2.1]oct-8-yl]-1-phenylpropyl)}1-propionyl-3-azetidinecarboxamide;

N-{(1S)-3-[3-endo-(2-Methyl-1H-benzimidazol-1-yl)-8-azabicyclo[3.2.1]oct-8-yl]-1-phenylpropyl}tetrahydro-3-furancarboxamide;

N-{(1S)-3-[3-endo-(2-Methyl-1H-benzimidazol-1-yl)-8-azabicyclo[3.2.1]oct-8-yl]-1-phenylpropyl}tetrahydro-2H-pyran4-carboxamide;

N-{(1S)-3-[3-endo-(2-Methyl-1H-benzimidazol-1-yl)-8-azabicyclo[3.2.1]oct-8-yl]-1-phenylpropyl}tetrahydro-2-furancarboxamide;

1-Acetyl-N-{(1S)-3-[3-endo-(1H-benzimidazol-1-yl)-8-azabicyclo[3.2.1]oct-8-yl]-1-phenylpropyl}-3-azetidinecarboxamide;

N-{(1S)-3-[3-endo-(1H-Benzimidazol-1-yl)-8-azabicyclo[3.2.1]oct-8-yl]-1-phenylpropyl}-1-propionyl-3-azetidinecarboxamide;

Methyl 3-[({(1S)-3-[3-exo-(2-methyl-1H-benzimidazol-1-yl)-8-azabicyclo[3.2.1]oct-8-yl]-1-phenylpropyl}amino)carbonyl]-1-azetidinecarboxylate;

N-{(1S)-3-[3-endo-(2-Methyl-1H-benzimidazol-1-yl)-8-azabicyclo[3.2.1]oct-8-yl]-1-phenylpropyl}-1-propionyl-3-azetidinecarboxamide 1-Acetyl-N-{(1S)-3-[3-endo-(2-methyl-1H-benzimidazol-1-yl)-8-azabicyclo[3.2.1]oct-8-yl]-1-phenylpropyl}-2-azetidinecarboxamide;

2-[Acetyl(methyl)amino]-N-{(1S)-3-[3-endo-(2-methyl-1H-benzimidazol-1-yl)-8-azabicyclo[3.2.1]oct-8-yl]-1-phenylpropyl}acetamide;

3-[Acetyl(methyl)amino]-N-{(1S)-3-[3-endo-(2-methyl-1H-benzimidazol-1-yl)-8-azabicyclo[3.2.1]oct-8-yl]-1-phenylpropyl}propanamide;

2-Methoxy-N-{(1S)-3-[3-endo-(2-methyl-1H-benzimidazol-1-yl)-8-azabicyclo[3.2.1]oct-8-yl]-1-phenylpropyl}acetamide;

3-Methoxy-N-{(1S)-3-[3-endo-(2-methyl-1H-benzimidazol-1-yl)-8-azabicyclo[3.2.1]oct-8-yl]-1-phenylpropyl}propanamide;

1-Acetyl-N-{(1S)-3-[3-endo-(2-methyl-1H-benzimidazol-1-yl)-8-azabicyclo[3.2.1]oct-8-yl]-1-phenylpropyl}-3-pyrrolidinecarboxamide;

1-Methyl-N-{(1S)-3-[3-endo-(2-methyl-1H-benzimidazol-1-yl)-8-azabicyclo[3.2.1]oct-8-yl]-1-phenylpropyl}-2-oxo-4-pyrrolidinecarboxamide;

1-Acetyl-N-{(1S)-3-[3-exo-(2-ethyl-1H-benzimidazol-1-yl)-8-azabicyclo[3.2.1]oct-8-yl]-1-phenylpropyl}-3-azetidinecarboxamide;

N-{(1S)-3-[3-exo-(2-Ethyl-1H-benzimidazol-1-yl)-8-azabicyclo[3.2.1]oct-8-yl]-1-phenylpropyl}-1-propionyl-3-azetidinecarboxamide;

1-Acetyl-N-((1S)-1-phenyl-3-{3-exo-[2-(trifluoromethyl)-1H-benzimidazol-1-yl]-8-azabicyclo[3.2.1]oct-8-yl}propyl)-3-azetidinecarboxamide;

N-((1S)-1-Phenyl-3-{3-exo-[2-(trifluoromethyl)-1H-benzimidazol-1-yl]-8-azabicyclo[3.2.1]oct-8-yl}propyl)-1-propionyl-3-azetidinecarboxamide;

N-((1S)-1-Phenyl-3-{3-exo[2-(trifiuoromethyl)-1H-benzimidazol-1-yl]-8-azabicyclo[3.2.1]oct-8-yl}propyl)acetamide;

2-[Acetyl(methyl)amino]-N-((1S)-1-phenyl-3-{3-exo-[2-(trifluoromethyl)-1H-benzimidazol-1-yl]-8-azabicyclo[3.2.1]oct-8-yl}propyl)acetamide;

1-Acetyl-N-{(1S)-3-[3-exo-(1H-benzimidazol-1-yl)-8-azabicyclo[3.2.1]oct-8-yl]-1-phenylpropyl}-3-azetidinecarboxamide;

N(1S)-3-[3-exo-(1H-Benzimidazol-1-yl)-8-azabicyclo[3.2.1]oct-8-yl]-1-phenylpropyl}-1-propionyl-3-azetidinecarboxamide;

1-acetyl-N(1S)-3-[3-exo-(5-fluoro-1H-benzimidazol-1-yl)-8-azabicyclo[3.2.1]oct-8-yl]-1-phenylpropyl)3-azetidinecarboxamide;

N-{(1S)-3-[3-exo-(5-Fluoro-1H-benzimidazol-1-yl)-8-azabicyclo[3.2.1]oct-8-yl]-1-phenylpropyl}-1-propionyl-3-azetidinecarboxamide;

1-Acetyl-N-{(1S)-3-[3-exo-(5-fluoro-2-methyl-1H-benzimidazol-1-yl)-8-azabicyclo[3.2.1]oct-8-yl]-1-phenylpropyl}3-azetidinecarboxamide;

N-{(1S)-3-[3-exo-(5-Fluoro-2-methyl-1H-benzimidazol-1-yl)-8-azabicyclo[3.2.1]oct-8-yl]-1-phenylpropyl}-1-propionyl-3-azetidinecarboxamide;

N-{(1S)-3-[3-exo-(2-methyl-1H-benzimidazol-1-yl)-8-azabicyclo[3.2.1]oct-8-yl]-1-phenylpropyl}-3-azetidinecarboxamide;

1-methyl-N-{(1S)-3-[3-exo-(2-methyl-1H-benzimidazol-1-yl)-8-azabicyclo[3.2.1]oct-8-yl]-1-phenylpropyl}-3-azetidinecarboxamide;

(2S)-1-acetyl-N-{(1S)-3-[3-exo-(2-methyl-1H-benzimidazol-1-yl)-8-azabicyclo[3.2.1]oct-8-yl]-1-phenylpropyl}-2-azetidinecarboxamide;

(2R)-1-acetyl-N-{(1S)-3-[3-exo-(2-methyl-1H-benzimidazol-1-yl)-8-azabicyclo[3.2.1]oct-8-yl]-1-phenylpropyl}-2-azetidinecarboxamide;

2-[acetyl(methyl)amino]-N-{(1S)-3-[3-exo-(2-methyl-1H-benzimidazol-1-yl)-8-azabicyclo[3.2.1]oct-8-yl]-1-phenylpropyl}acetamide;

3-[acetyl(methyl)amino]-N-{(1S)-3-[3-exo-(2-methyl-1H-benzimidazol-1-yl)-8-azabicyclo[3.2.1]oct-8-yl]-1-phenylpropyl}propanamide;

1-acetyl-N-{(1S)-3-[3-exo-(2-methyl-1H-benzimidazol-1-yl)-8-azabicyclo[3.2.1]oct-8-yl]-1-phenylpropyl}-3-pyrrolidinecarboxamide;

N-{(1S)-3-[3-exo-(2-methyl-1H-benzimidazol-1-yl)-8-azabicyclo[3.2.1]oct-8-yl]-1-phenylpropyl}-1-(trifluoromethyl)cyclopropanecarboxamide;

2-methoxy-N-{(1S)-3-[3-exo-(2-methyl-1H-benzimidazol-1-yl)-8-azabicyclo[3.2.1]oct-8-yl]-1-phenylpropyl}acetamide;

3-methoxy-N-{(1S)-3-[3-exo-(2-methyl-1H-benzimidazol-1-yl)-8-azabicyclo[3.2.1]oct-8-yl]-1-phenylpropyl}propanamide;

1-Acetyl-N-{(1S)-3-[3-exo-(4-fluoro-2-methyl-1H-benzimidazol-1-yl)-8-azabicyclo[3.2.1]oct-8-yl]-1-phenylpropyl}-3-azetidinecarboxamide;

N-{(1S)-3-[3-exo-(4-Fluoro-2-methyl-1H-benzimidazol-1-yl)-8-azabicyclo[3.2.1]oct-8-yl]-1-phenylpropyl}-3-azetidinecarboxamide;

1-Methyl-N-{(1S)-3-[3-exo-(4-fluoro-2-methyl-1H-benzimidazol-1-yl)-8-azabicyclo[3.2.1]oct-8-yl]-1-phenylpropyl}-3-azetidinecarboxamide;

N-{(1S)-3-[3-exo-(4-Fluoro-2-methyl-1H-benzimidazol-1-yl)-8-azabicyclo[3.2.1]oct-8-yl]-1-phenylpropyl}-1-propionyl-3-azetidinecarboxamide;

2-Methoxy-N-{(1S)-3-[3-exo-(4-Fluoro-2-methyl-1H-benzimidazol-1-yl)-8-azabicyclo[3.2.1]oct-8-yl]-1-phenylpropyl}acetamide;

N-{(1S)-3-[3-exo-(4-Fluoro-2-Methyl-1H-benzimidazol-1-yl)-8-azabicyclo[3.2.1]oct-8-yl]-1-phenylpropyl}acetamide;
3-Methoxy-N-{(1S)-3-[3-exo-(4-fluoro-2-methyl-1H-benzimidazol-1-yl)-8-azabicyclo[3.2.1]oct-8-yl]-1-phenylpropyl}propanamide;
2-[Acetyl(methyl)amino]-N-{(1S)-3-[3-exo-(4-fluoro-2-methyl-1H-benzimidazol-1-yl)-8-azabicyclo[3.2.1]oct-8-yl]-1-phenylpropyl}acetamide;
3-[Acetyl(methyl)amino]-N-{(1S)-3-[3-exo-(4-fluoro-2-methyl-1H-benzimidazol-1-yl)-8-azabicyclo[3.2.1]oct-8-yl]-1-phenylpropyl}propanamide;
N-{(1S)-3-[3-exo-(4-fluoro-2-methyl-1H-benzimidazol-1-yl)-8-azabicyclo[3.2.1]oct-8-yl]-1-phenylpropyl}-3-methyl-3-oxetanecarboxamide;
3-Ethyl-N-{(1S)-3-[3-exo-(4-fluoro-2-methyl-1H-benzimidazol-1-yl)-8-azabicyclo[3.2.1]oct-8-yl]-1-phenylpropyl}-3-oxetanecarboxamide;
N-{(1S)-3-[3-exo-(4-Fluoro-2-methyl-1H-benzimidazol-1-yl)-8-azabicyclo[3.2.1]oct-8-yl]-1-phenylpropyl}-3-oxetanecarboxamide;
3-Ethyl-N-{(1S)-3-[3-exo-(4-fluoro-1H-benzimidazol-1-yl)-8-azabicyclo[3.2.1]oct-8-yl]-1-phenylpropyl}-3-oxetanecarboxamide;
N-{(1S)-3-[3-exo-(4-Fluoro-1H-benzimidazol-1-yl)-8-azabicyclo[3.2.1]oct-8-yl]-1-phenylpropyl}-3-methyl-3-oxetanecarboxamide;
N-{(1S)-3-[3-exo-(4-Fluoro-1H-benzimidazol-1-yl)-8-azabicyclo[3.2.1]oct-8-yl]-1-phenylpropyl}-3-oxetanecarboxamide;
N-{(1S)-3-[3-exo-(4-Fluoro-1H-benzimidazol-1-yl)-8-azabicyclo[3.2.1]oct-8-yl]-1-phenylpropyl}-3-azetidinecarboxamide;
N-{(1S)-3-[3-exo-(4-Fluoro-1H-benzimidazol-1-yl)-8-azabicyclo[3.2.1]oct-8-yl]-1-phenylpropyl}-1-methyl-3-azetidinecarboxamide;
1-Acetyl-N-{(1S)-3-[3-exo-(4-fluoro-1H-benzimidazol-1-yl)-8-azabicyclo[3.2.1]oct-8-yl]-1-phenylpropyl}-3-azetidinecarboxamide;
N-{(1S)-3-[3-exo-(4-Fluoro-1H-benzimidazol-1-yl)-8-azabicyclo[3.2.1]oct-8-yl]-1-phenylpropyl}-1-propionyl-3-azetidinecarboxamide;
N-{(1S)-3-[3-exo-(4-Fluoro-1H-benzimidazol-1-yl)-8-azabicyclo[3.2.1]oct-8-yl]-1-phenylpropyl}-2-methoxyacetamide;
N-{(1S)-3-[3-exo-(4-Fluoro-1H-benzimidazol-1-yl)-8-azabicyclo[3.2.1]oct-8-yl]-1-phenylpropyl}acetamide;
N{-1S)-3-[3-exo-(4-fluoro-1H-benzimidazol-1-yl)-8-azabicyclo[3.2.1]oct-8-yl]-1-phenylpropyl}-3-methoxypropanamide;
2-[Acetyl(methyl)amino]-N-{(1S)-3-[3-exo-(4-fluoro-1H-benzimidazol-1-yl)-8-azabicyclo[3.2.1]oct-8-yl]-1-phenylpropyl}acetamide;
3-[Acetyl(methyl)amino]-N-{(1S)-3-[3-exo-(4-fluoro-1H-benzimidazol-1-yl)-8-azabicyclo[3.2.1]oct-8-yl]-1-phenylpropyl}propanamide; and pharmaceutically acceptable salts thereof.

As disclosed herein, one aspect of the present invention provides for a method of treating, preventing, or managing a CCR-5 expressing neoplasm or a metastasis of the CCR5-expressing neoplasm in a subject by administering to the subject a CCR5 receptor antagonist. In one embodiment, CCR5 receptor antagonists are administered in the form of pharmaceutical formulations or dosage forms that include the CCR5 receptor antagonists. In one embodiment, the CCR5 receptor antagonists are used in the form of acids, esters, or other suitable chemical derivatives. In one embodiment, the CCR5 receptor antagonists are in the form of pharmaceutically acceptable salts derived from various organic and inorganic acids and bases in accordance with procedures well known in the art. In one embodiment, the expression "pharmaceutically acceptable salt" as used herein is intended to mean an active ingredient comprising a CCR5 receptor antagonist utilized in the form of a salt thereof, especially where the salt form confers on the CCR5 receptor antagonist improved pharmacokinetic properties as compared to the free form of the CCR5 receptor antagonist or other previously disclosed salt form. In one embodiment, a pharmaceutically acceptable salt form of the CCR5 receptor antagonist may also initially confer a desirable pharmacokinetic property on the CCR5 receptor antagonist which, it did not previously possess, and may even positively affect the pharmacodynamics of the CCR5 receptor antagonist with respect to its therapeutic activity in the body. In one embodiment, the pharmacokinetic properties of the CCR5 receptor antagonist which may be favorably affected include, e.g., the manner in which the CCR5 receptor antagonist is transported across cell membranes, which in turn may directly and positively affect the absorption, distribution, biotransformation or excretion of the CCR5 receptor antagonist. While the route of administration of the pharmaceutical composition is important and various anatomical, physiological and pathological factors can critically affect bioavailability, the solubility of the CCR5 receptor antagonist is usually dependent upon the character of the particular salt form thereof which it utilized. Further, an aqueous solution may provide the most rapid absorption of an active ingredient into the body of a patient being treated, while lipid solutions and suspensions, as well as solid dosage forms, may result in less rapid absorption. Oral ingestion of the CCR5 receptor antagonist is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of the CCR5 receptor antagonist into different pharmaceutically acceptable salt forms may be effective in overcoming or alleviating one or more of the above-recited problems encountered with absorption of oral dosage forms. Well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

Base salts of the compounds of suitable CCR5 receptor antagonists include, but are not limited to ammonium, salts; alkali metal salts such as sodium and potassium; alkaline earth metal salts such as calcium and magnesium; salts with organic bases such as dicyclohexylamine, meglumine, N-methyl-D-glucamine, trishydroxymethyl)methylamine (tromethamine), and salts with amino acids such as arginine, lysine, etc. Compounds of the present invention which comprise basic nitrogen-containing groups may be quaternized with such agents as ($C_1$-$C_4$) alkyl halides, e.g., methyl, ethyl, iso-propyl and tert-butyl chlorides, bromides and iodides; di($C_1$-$C_4$) alkyl sulfate, e.g., dimethyl, diethyl and diamyl sulfates; ($C_{10}$-$C_{18}$) alkyl halides, e.g., decyl, dodecyl, lauryl, myristyl and stearyl chlorides, bromides and iodides; and aryl-($C_1$-$C_4$) alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, subsalicylate, tartrate, thiomalate, tosylate and tromethamine.

Multiple salts forms are included within the scope of the present invention where a CCR5 receptor antagonist contains more than one group capable of forming such pharmaceutically acceptable salts. Examples of typical multiple salt forms include, but are not limited to bitartrate, diacetate, difumarate, dimeglumine, diphosphate, disodium, and trihydrochloride. Suitable CCR5 receptor antagonists can be administered alone but will generally be administered in admixture with one or more suitable pharmaceutical excipients, diluents or carriers selected with regard to the intended route of administration and standard pharmaceutical practice.

For example, a CCR5 receptor antagonist can be administered orally or sublingually in the form, of tablets, capsules, ovules, elixirs, solutions or suspensions, which may contain, flavouring or colouring agents, for immediate or controlled release applications. Such tablets may contain excipients such as microcrystalline cellulose, lactose, sodium citrate, calcium carbonate, dicalcium phosphate and glycine, disintegrants such as starch (preferably corn, potato or tapioca starch), alginic acid and certain complex silicates, and granulation binders such as polyvinylpyrrolidone, sucrose, gelatin and acacia. Additionally, lubricating agents such as magnesium stearate, sodium lauryl sulfate and talc may be included. Solid compositions of a similar type may also be employed as fillers in gelatin capsules. Preferred excipients in this regard include lactose or milk sugar as well as high molecular weight polyethylene glycols. For aqueous suspensions and/or elixirs, the CCR5 receptor antagonist may be combined with various sweetening or flavouring agents, colouring matter or dyes, with emulsifying and/or suspending agents and with diluents such as water, ethanol, propylene glycol and glycerin, and combinations thereof.

Suitable CCR5 receptor antagonists can also be injected parenterally, for example, intravenously, intraperitoneally, intrathecally, intraventricularly, intrastemally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

For oral and parenteral administration to human subjects, the daily dosage level of the CCR5 receptor antagonist will usually be from 1 micro gram/kg to 25 mg/kg (in single or divided doses). Thus tablets or capsules of the CCR5 receptor antagonist may contain from 0.05 mg to 1.0 g of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. Suitable CCR5 receptor antagonists can also be administered intranasally or by inhalation and are conveniently delivered in the form of a dry powder inhaler or an aerosol spray presentation from a pressurised container or a nebuliser with she use of a suitable propellant, eg dichlorodifluoromethane, trichlorofluoromethane, dichlorotetrafluoroethane, a hydrofluoroalkane such as 1,1,1,2-tetrafluorethane (HFA 134a), carbon dioxide or other suitable gas. In the ease of a pressurised aerosol, the dosage unit may be determined by providing a valve to deliver a metered amount. The pressurized container or nebulizer may contain a solution or suspension of the active compound, eg using a mixture of ethanol and the propellant as the solvent, which may additional contain a lubricant, e.g. sorbitan trioleate. Capsules and cartridges (made, for example, from gelatin) for use in an inhaler or insufflator may be formulated to contain a powder mix of a CCR5 receptor antagonist and a suitable powder base such as lactose or starch.

Aerosol or dry powder formulations are preferably arranged so that each metered dose or "puff" contains from 20 µg to 20 mg of a CCR5 receptor antagonist for delivery to the subject. The overall daily dose with an aerosol will be in the range of from 20 µg to 20 mg which may be administered in a single dose or, more usually, in divided doses throughout the day. Alternatively, Suitable CCR5 receptor antagonists can be administered in the form of a suppository or pessary, or they may be applied topically in the form of a lotion, solution, cream, ointment or dusting powder. The CCR5 receptor antagonist may also be transdermally administered by the use of a skin patch. They may also be administered by the ocular route, particularly for treating neurological disorders of the eye.

For ophthalmic use, the compounds can be formulated as micronised suspensions in isotonic, pH adjusted, sterile saline, or, preferably, as solutions in isotonic, pH adjusted, sterile saline, optionally in combination with a preservative such as benzylalkonium chloride. Alternatively, they maybe formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

In some embodiments, the compounds described herein can modulate CCR5 chemokine receptor activity and consequent or associated pathogenic processes subsequently mediated by the CCR5 receptor and its ligands. The expression "modulate CCR5 chemokine receptor activity" as used herein is intended to refer to manipulation of the basic physiological processes and agencies which involve CCR5 chemokine receptors and their ligands. Included within the scope of this intended meaning are all types and subtypes of CCR5 receptors, in whatever tissues of a particular patient they are found, and in or on whatever components of the cells comprising those tissues they may be located. Most commonly, CCR5 receptors are situated on the cell membranes of particular cell types such as monocytes. CCR5 receptors participate in and define, along with various endogenous ligands to which they are naturally bound, signaling pathways which control important cellular and tissue functions by means of the influence which they exert on the movement of agents such as the chemokines, into and out of those cells and tissues.

The dosage and dose rate of the compounds of Formula (I) effective for treating or preventing diseases and conditions in a patient which are mediated by or associated with modulation of CCR5 chemokine receptor activity as described herein, as well as for favorably affecting the outcome thereof in the patient, in accordance with the methods of treatment of the present invention comprising administering to the patient a therapeutically effective amount of a CCR5 receptor antagonist, will depend on a variety of factors such as the nature of the CCR5 receptor antagonist, the size of the patient, the goal of the treatment, the nature of the pathology being treated, the specific pharmaceutical composition used, the concurrent treatments that the patient may be subject to, and the observations and conclusions of the treating physician.

Generally, however, the effective therapeutic dose of a suitable CCR5 receptor antagonist which will be administered to a subject will be between about 10 μg (0.01 mg)/kg and about 60.0 mg/kg of body weight per day, preferably between about 100 μg (0.1 mg)/kg and about 10 mg/kg of body weight per day, more preferably between about 1.0 mg/kg and about 6.0 mg/kg of body weight per day, and most preferably between about 2.0 mg/kg and about 4.0 mg/kg of body weight per day of the CCR5 receptor antagonist.

Included within the scope of the present invention are embodiments comprising coadministration of, and compositions which contain, in addition to a CCR5 receptor antagonist as active ingredient, additional therapeutic agents and active ingredients. Such multiple drug regimens, often referred to as combination therapy, may be used in the treatment and prevention of any of the diseases or conditions mediated by or associated with CCR5 chemokine receptor modulation, particularly cancer metastasis. The use of such combinations of therapeutic agents is especially pertinent with respect to the treatment, prevention, or management of cancer metastasis within a subject in need of treatment cancer, prevention cancer, or management of risk of cancer metastasis.

Exemplary CCR5 receptor antagonists may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing.

As disclosed in U.S. Pat. No. 6,667,314 by Perros et al. CCR5 antagonists can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The CCR5 receptor antagonists may also be administered as fast-dispersing or fast-dissolving dosage forms or in the form of a high energy dispersion or as coated particles. Suitable formulations of the compounds of the CCR5 receptor antagonist may be in coated or uncoated form, as desired. Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

"Metastasis", as used herein, is defined as the transfer of malignant tumor cells, or neoplasm, via the circulatory or lymphatic systems or via natural body cavities, usually from the primary site of neoplasia to a distant site in the body, and subsequent development of secondary tumors or colonies in the new location. In some exemplary embodiments of the methods of the present invention, metastasis comprises a tumor metastasis in or more organs selected from the group consisting of liver, brain, bladder, lung, adrenal gland, kidney, bone, skin or pancreas or control kidney and combinations thereof.

In another aspect, the present invention provides a method of identifying a compound that reduces or prevents or treats cancer metastasis. In one embodiment, the method identifies a candidate compound that selectively interferes with proliferation or viability of neoplastic cells that over express CCR5 and/or over express at least one of CCR5 receptor ligand. In one embodiment, the method identifies a candidate compound that selectively blocks activity of CCR5 and/or at least one of CCR5 receptor ligand in neoplastic cells that over express CCR5 and/or over express at least one of CCR5 receptor ligand. In one exemplary embodiment, the method for identifying a candidate compound that reduces or prevents or treats cancer metastasis in neoplastic cells that over express CCR5 and/or over express at least one of CCR5 receptor ligand, comprises (a) contacting a one or more neoplastic cells that over express CCR5 and/or over express at least one of CCR5 receptor ligand with one or more candidate compounds; and (b) detecting activity of and/or proliferation or viability of the one or more neoplastic cells that over express CCR5 and/or over express at least one of CCR5 receptor ligand, wherein decreased activity and/or decreased proliferation and/or decreased viability of the one or more neoplastic cells (relative to as compared to a control sample) identifies the candidate compound as a compound that that selectively reduces or prevents or treats cancer metastasis in neoplastic cells that over express CCR5 and/or over express at least one of CCR5 receptor ligand. In one embodiment, if proliferation of the one or more neoplastic cells is decreased/depressed compared to untreated (control) neoplastic cells that over express CCR5 and/or over express at least one of CCR5 receptor ligand, the candidate compound is identified as a compound that selectively reduces or prevents or treats metastasis of a neoplasm cells that over express CCR5 and/or over express at least one of CCR5 receptor ligand. In one embodiment, if viability of the one or more neoplastic cells is decreased/depressed compared to untreated (control) neoplastic cells that over express CCR5 and/or over express at least one of CCR5 receptor ligand, the candidate compound is identified as a compound that that selectively reduces or prevents or treats metastasis of a neoplasm cells that over express CCR5 and/or over express at least one of CCR5 receptor ligand. In one embodiment, the one or more CCR5 receptor ligands comprise CCL5. In one embodiment, the one or more CCR5 receptor ligands comprise CCL8. In one embodiment, the one or more CCR5 receptor ligands comprise CCL7.

For the study disclosed herein, CCL5 and CCR5 expression in human breast cancer cell lines were investigated as well as the effect of CCR5 antagonists in vitro and in vivo. An interrogation was conducted using a microarray dataset to evaluate CCR5 and CCL5 expression in the context of 2,254 patient breast cancer samples. Samples in the dataset were assigned to five breast cancer subtypes, including luminal A, luminal B, normal-like, basal and HER-2 overexpressing disease. The analysis revealed an increased expression of CCL5 and CCR5 in patients with basal and HER-2 subtypes. 58% the cancer samples indicated a positive CCR5 and CCL5 signature. It was found that oncogenes turn on the CCR5 receptor in normal breast cells as they became transformed into cancer cells. Metastasis those cells was also found to be regulated by CCR5.

To evaluate the functional relevance of CCR5 in cellular migration and invasion in vitro, the drugs were tested in 3-D invasion assays with two different cell lines. It was found that both antagonists inhibited breast cancer cell invasiveness.

To evaluate the functional relevance of CCR5 in cellular migration and invasion in vivo, mice were injected with the antagonists and invasiveness of the basal breast cancer cells to other tissue, i.e. lung, was tracked with bioluminescence imaging. It was found that mice treated with the drug showed a more than 90% reduction in both the number and size of pulmonary metastases compared to untreated mice. This and the other preclinical studies provide the rational basis for studying the use of CCR5 antagonists as new treatments to block the dissemination of basal breast cancers. These findings may also have implications for other cancers where CCR5 promotes metastasis, such as prostate and gastric.

Referring to the drawings in detail, wherein like reference numerals indicate like elements throughout, there are exemplary embodiments of the present invention shown in FIGS. 1A-14D.

Referring to FIG. 1A, there is shown a heatmap of the expression of CCL5 and its receptor CCR5 in samples from patients with breast cancer divided by molecular subtypes of breast cancer, namely luminal A, luminal B, basal, normal-like, and Her-2, based on their gene expression pattern. The heatmap shows that relative abundances of CCL5 and CCR5 are increased (over expressed) in patients with the basal and HER-2 breast cancer subtypes. The heatmap also shows that CCL5 and CCR5 are over expressed in the Her-2 breast cancer subtype.

Referring to FIGS. 1B1 to 1B5, there is shown fluorescence-activated cell sorting (FACS) scatter plots and correlation analysis (Student t test) of the expression of CCL5 and CCR5 among the breast cancer molecular subtypes whose expression of CCL5 and its receptor CCR5 is shown FIG. 1A. Consistent with the expression of CCL5 and its receptor CCR5 observed in A, the scatter plots show CCL5 and CCR5 are over expressed in patients with the basal and HER-2 breast cancer subtypes.

Figure 1C:
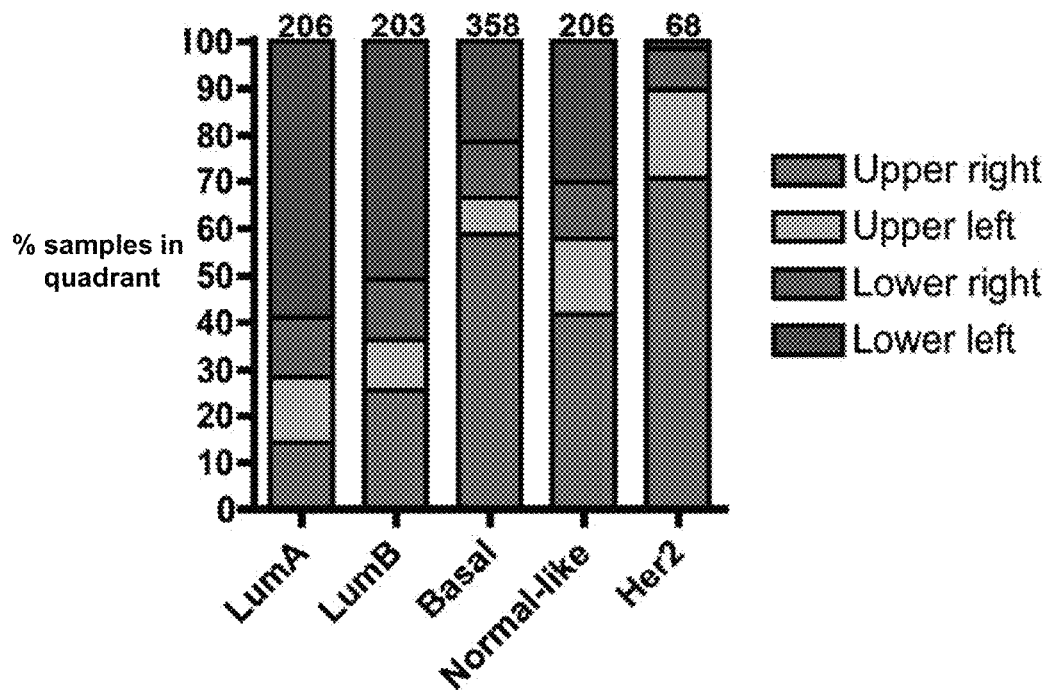
FIG. 1C illustrates quantification of the proportions of the breast cancer samples overexpressing CCL5 and CCR5, fraction of the bars representing upper right quadrants of the scatter plots shown in FIG. B.

Referring to FIG. 1C, there is shown quantification of the proportions of the breast cancer samples overexpressing CCL5 and CCR5 (fraction of the bars representing upper right quadrants of the scatter plots shown in FIGS. 1B1 to 1B5) displayed in FIGS. 1B1 to 1B5. The number of samples in each subtype is indicated at the top of the bar.

Figure 1D:
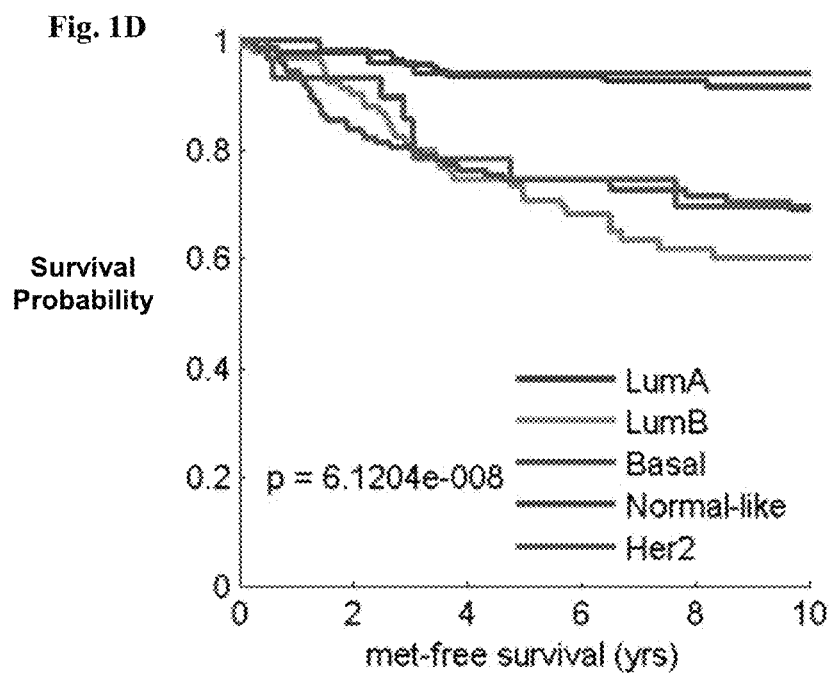
FIG. 1D illustrates metastasis-free Kaplan-Meier plots and log-rank analysis for the different molecular subtypes of breast cancer in the analyzed database, which is described in Materials and Methods section of this of this application.

Referring to FIG. 1D, there is shown metastasis-free Kaplan-Meier plots and log-rank analysis for the different genetic subtypes in the analyzed database described in Materials and Methods section of the present disclosure. The metastasis-free Kaplan-Meier plots show that patients with the basal or HER-2 subtypes of breast cancer display increased probability to develop metastasis.

Figure 2C:
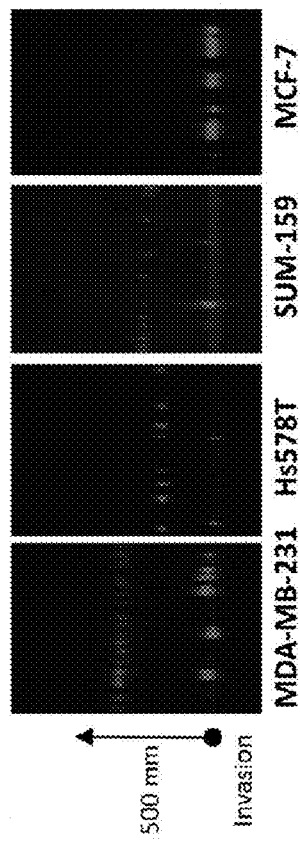
FIG. 2C illustrates 3D invasion into collagen gels by breast cancer cell lines, using CCL5 (15 μg/mL) as chemoattractant.
Figure 2D:
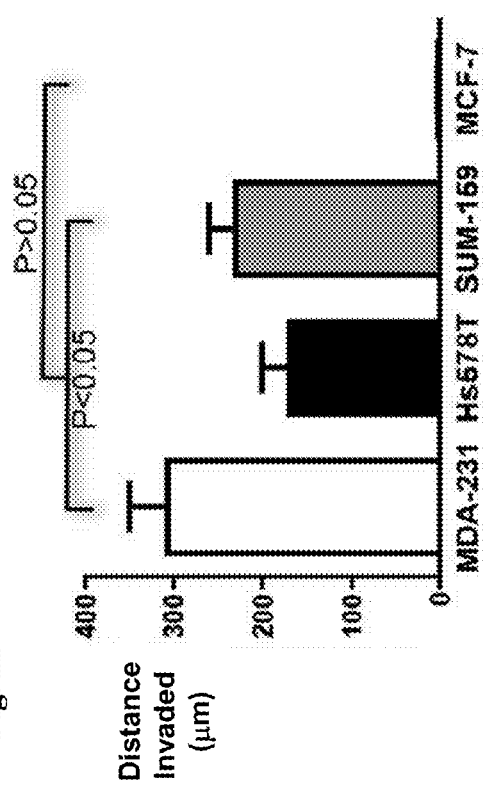
FIG. 2D illustrates mean distances of invasion±SEM from 3 independent experiments.
Figure 2E:
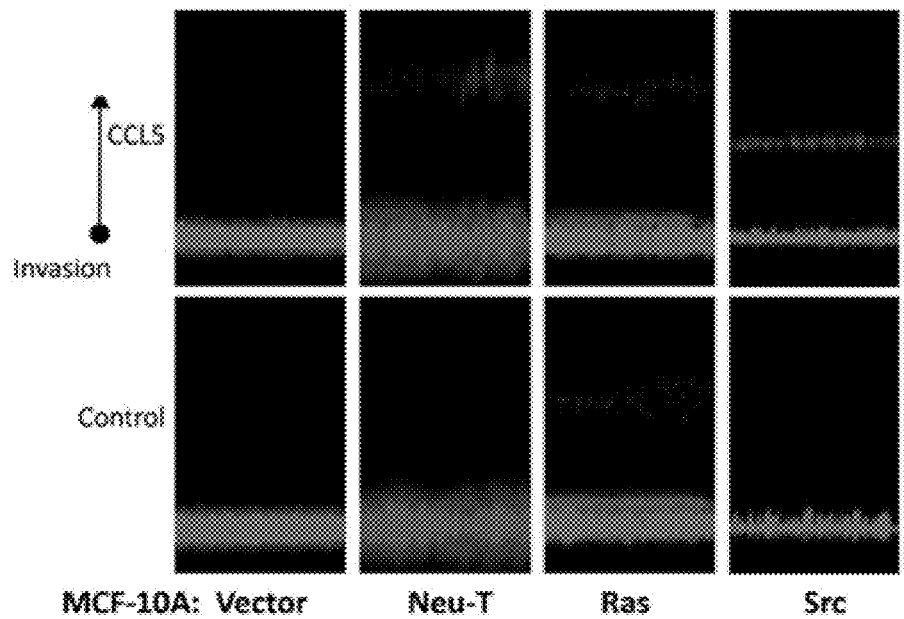
Figure 2F:
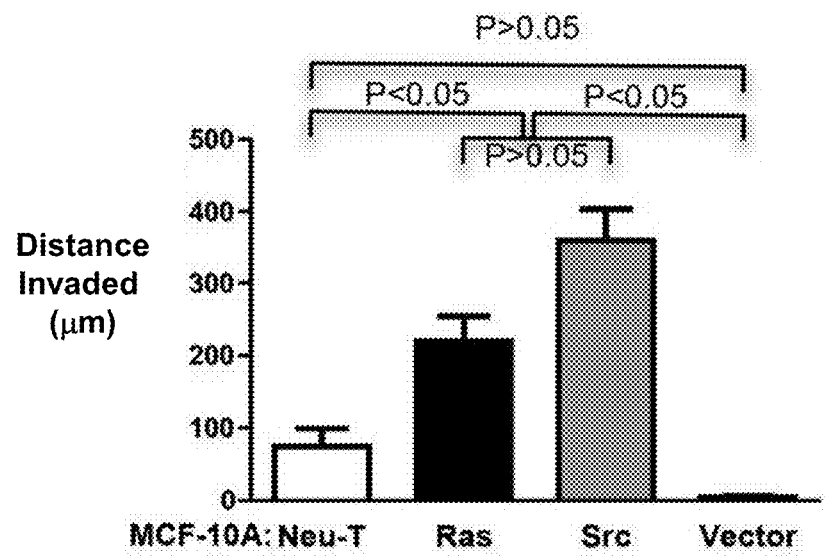
FIG. 2F illustrates quantification (F, mean±SEM, n=3) 3D invasion assays for MCF-10A cells and MCF-10A-NeuT, -Ras, and -Src derivatives showing that CCL5-induced invasion is activated by oncogenic transformation shown in FIG. 2E.
Figure 2G:
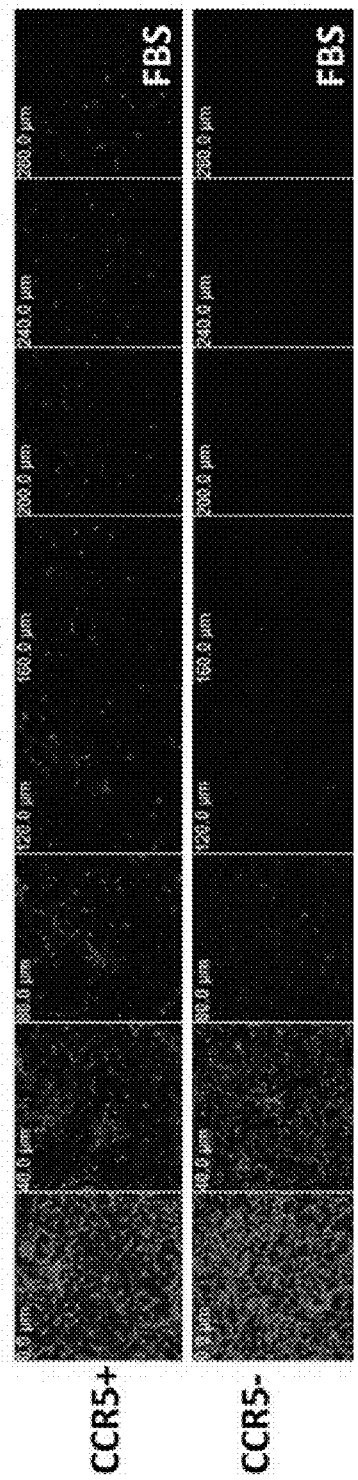
FIG. 2G illustrates CCR5+ and CCR5− subpopulations from SUM-159 cell line that were isolated by FACS and their respected invasion into collagen gels evaluated using fetal bovine serum (FBS) as chemoattractant.
Figure 2H:
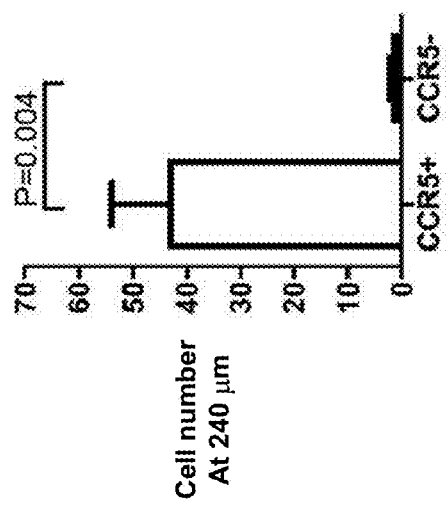
FIG. 2H illustrates quantification of the invasion of CCR5+ and CCR5− subpopulations into collagen as mean±SEM of the two independent experiments shown in FIG. 2G.

FIGS. 2A-2H, show that human breast cancer cell lines that express CCR5 respond to CCL5. In FIG. 1A, flow cytometric histograms of the CCR5 expression in MDA-MB-231 breast cancer cells identified a subpopulation of CCR5+ cells. In FIGS. 2B and 2B2, induction of calcium signaling in cells loaded with Fluo-4-AM before the sequential addition of CCL5 (60 μg/mL) and FBS (5%) is shown. A fraction of cells responded to CCL5 (closed arrowheads in the middle of micrographs) whereas the rest did not (open arrowheads). The average changes in fluorescence on 5 responsive (green line) and 5 nonresponsive (red line) cells are represented in the far right graphs. Data shown are representative of 3 to 5 independent experiments for each cell line (Bar, 100 μm). In FIG. 2C, 3D invasion into collagen gels by breast cancer cell lines, using CCL5 (15 μg/mL) as chemoattractant is shown. FIG. 2D shows mean distances of invasion±SEM from 3 independent experiments whose 3D invasion are shown in FIG. 2C. FIG. 2E shows 3D invasion assays, and their corresponding quantification shown in FIG. 2F (mean±SEM, n=3), for MCF-10A cells and MCF-10A-NeuT, -Ras, and -Src derivatives showing that CCL5-induced invasion is activated by oncogenic transformation. FIG. 2G shows CCR5+ cells display increased invasiveness. CCR5+ and CCR5− subpopulations from SUM-159 cell line were isolated by FACS and invasion into collagen gels was evaluated using FBS as chemoattractant. Quantification of FACS and invasion into collagen gels experiments of the samples in FIG. 2G is shown in FIG. 2H as mean±SEM of 2 independent experiments. Statistical analysis was conducted using the Student t test.

FIGS. 3A1-3D show that CCR5 antagonists block CCL5-induced calcium signaling. In FIGS. 3A1 to 3A4, there is shown intensity versus time analysis of Fluo-4 AM-loaded MDA-MB-231 cells treated with the CCR5 antagonists maraviroc or vicriviroc (100 nmol/L) for 30 minutes before the addition of CCL5 (60 μg/mL). Micrographs illustrate the axis (x-x') of the pseudoline scan plot. Those axes were used to construct the adjacent intensity versus time plots. In FIG. 3B, there is shown comparison of the fraction of cells with increased fluorescence intensity upon addition of CCL5. In FIGS. 3C1 to 3C4, CCL5-induced calcium signaling was also blocked by CCR5 antagonists in Hs578T cells. The corresponding quantification is shown in FIG. 3D. The data in FIGS. 3B and 3D are mean±SEM of 3 to 4 independent experiments. Statistical analysis was conducted using the Student t test.

Figure 4A:
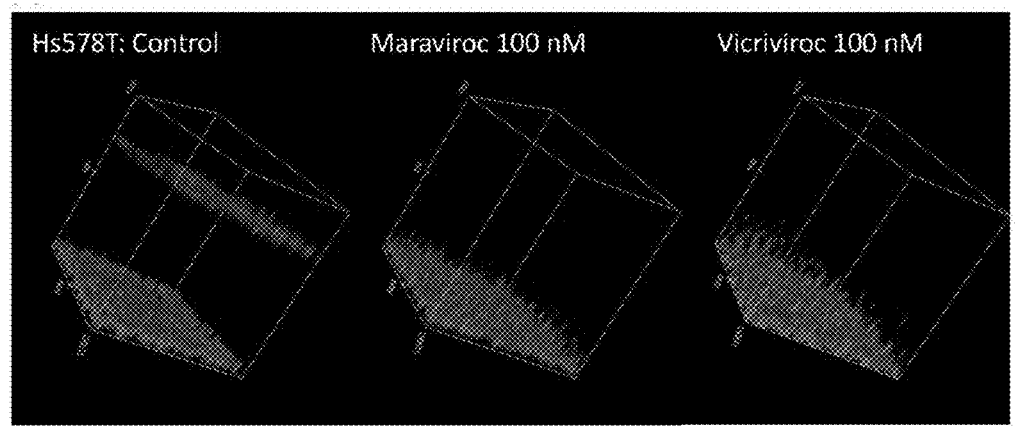
FIG. 4A illustrates 3D reconstruction of FBS-induced invasion into collagen gels by Hs578T breast cancer cells in presence of CCR5 antagonists (100 nmol/L)
Figure 4B:
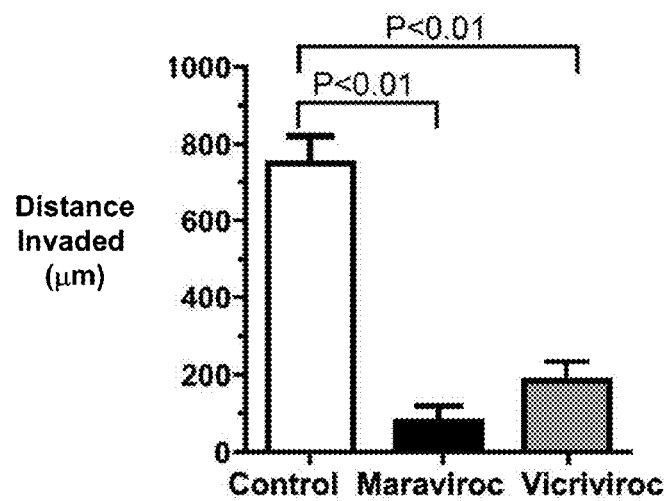
FIG. 4B illustrates quantifications (mean±SEM, n=3) and analysis (Bonferroni t test) of the FBS-induced invasion into collagen gels by Hs578T breast cancer cells shown in FIG. 4A.
Figure 4C:
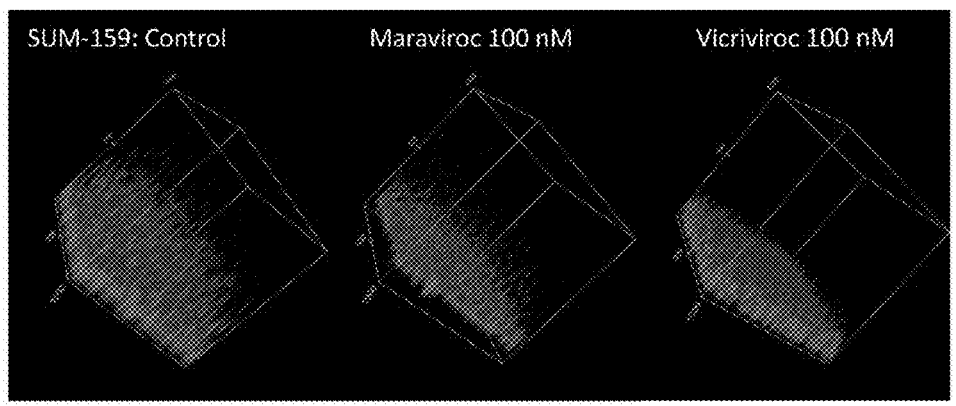
FIG. 4C illustrates 3D reconstruction of FBS-induced invasion into collagen gels by SUM-159 breast cancer cells in presence of CCR5 antagonists (100 nmol/L)
Figure 4D:
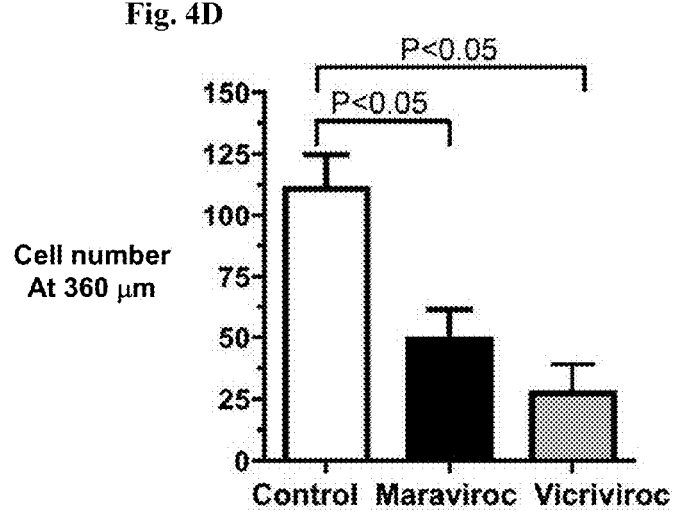
FIG. 4D illustrates quantifications (mean±SEM, n=3) and analysis (Bonferroni t test) of the FBS-induced invasion into collagen gels by SUM-159 breast cancer cells shown in FIG. 4A.

FIGS. 4A-4D show that CCR5 antagonists block FBS-induced breast cancer cell invasion. In FIG. 4A, there is shown 3D reconstruction of FBS-induced invasion into collagen gels by Hs578T breast cancer cells in presence of CCR5 antagonists (100 nmol/L). In FIG. 3C there is shown 3D reconstruction of FBS-induced invasion into collagen gels by SUM-159 breast cancer cells in presence of CCR5 antagonists (100 nmol/L). The corresponding quantifications (mean±SEM, n=3) and analysis (Bonferroni t test) are displayed in FIGS. 4B and 4D.

Figure 5A:
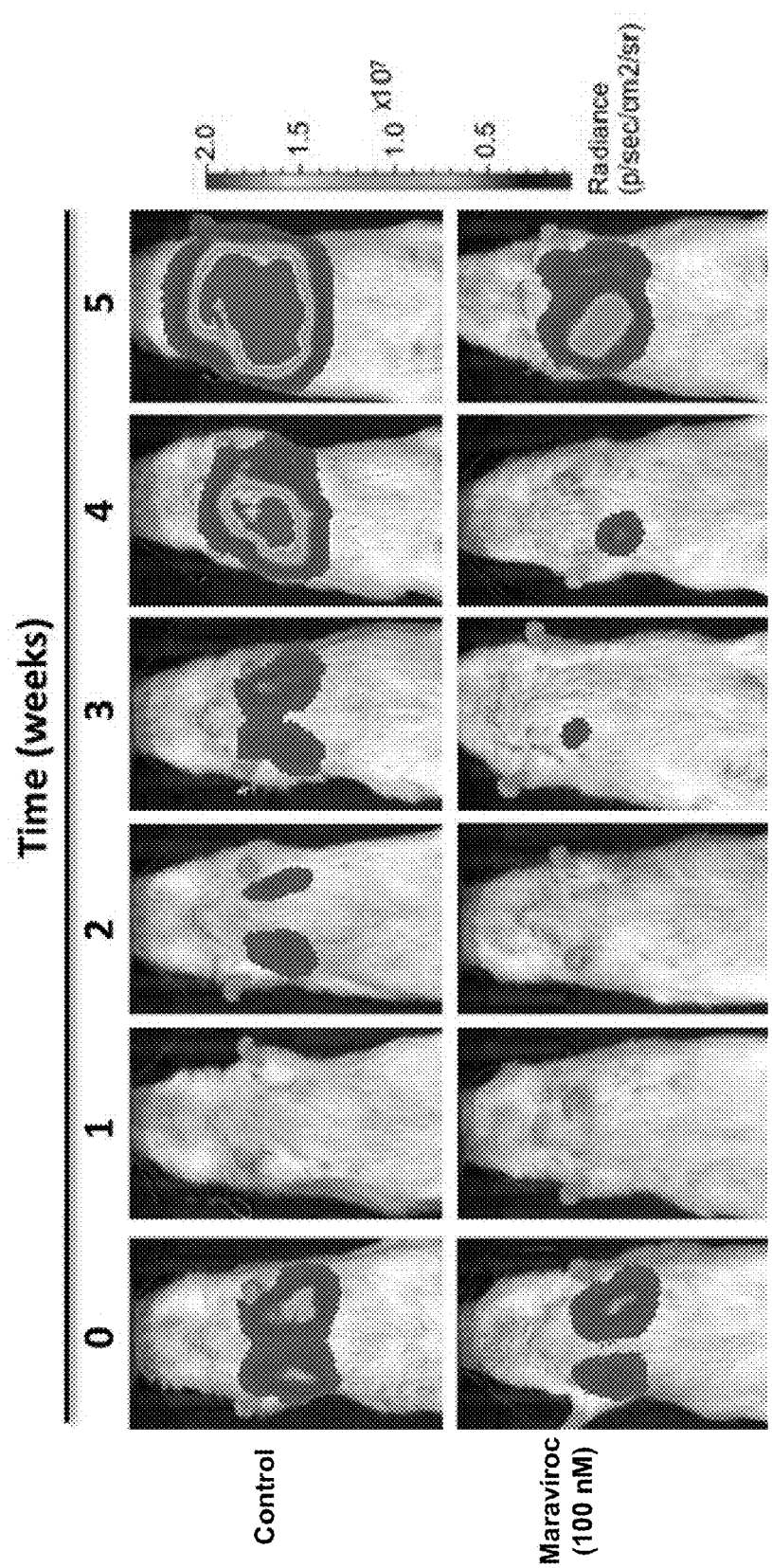
FIG. 5A shows exemplary in vivo bioluminescent images (BLIs) of vehicle- or maraviroc-treated (8 mg/kg every 12 hours) of nonobese diabetic (NOD)/severe combined immunodeficiency (SCID) mice (hereinafter abbreviated as NOD/SCID mice)
Figure 5D:
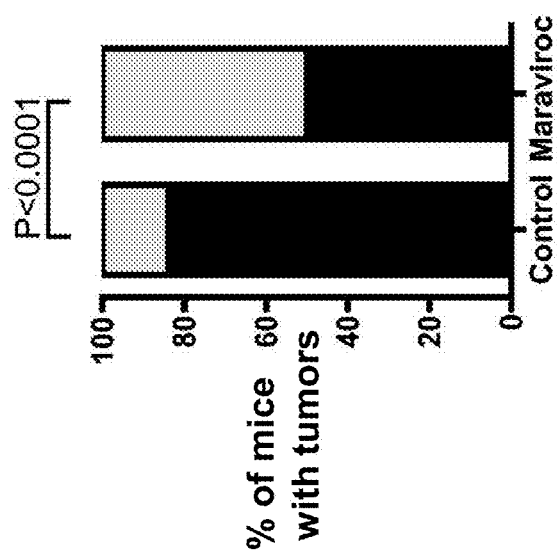
FIG. 5D showing the fraction of mice with metastatic tumors being significantly larger in the control group (P<0.0001, Fisher exact test)
Figure 5E:
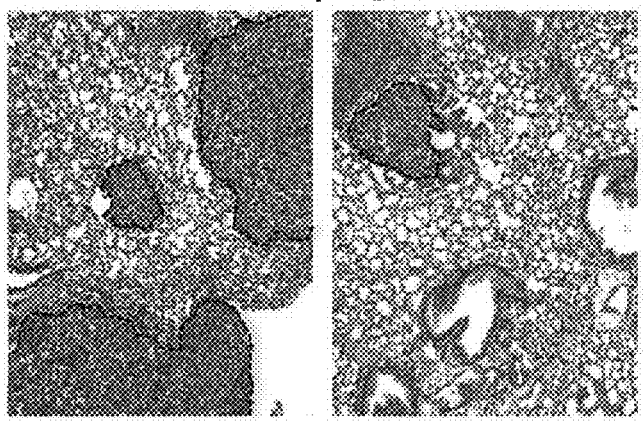
FIG. 5E showing histological analysis (hematoxylin and eosin staining, ×100) of the area covered by metastatic tumors in lung slides.

Referring to FIGS. 5A-5F, the data presented show that the CCR5 antagonist maraviroc inhibits lung metastases in vivo. In FIG. 5A, MDA-MB-231 cells transduced with Luc2-eGFP fusion protein were injected into the tail vein of NOD/SCID mice and the in vivo bioluminescent signal was quantified weekly. Representative in vivo images of vehicle- or maraviroc-treated (8 mg/kg every 12 hours) mice are shown in FIG. 5A. In FIG. 5B, there is shown quantification (mean±SEM, n=6) of BLI in the control (red line) and treated groups (blue line. Statistical comparison (*, P=0.048) was carried out using Student t test with Welch correction for heterogeneous variances. As shown in FIGS. 5C1 and 5C2, the presence of pulmonary tumors and the differences between treatments were corroborated by ex vivo imaging (left) and India ink staining (right). As shown in FIG. 5D, the fraction of mice with metastatic tumors was significantly larger in the control group (P<0.0001, Fisher exact test). FIG. 5E shows histologic analysis (hematoxylin and eosin staining, ×100) and the corresponding quantification (shown in FIG. 5F) of the area covered by metastatic tumors in lung slides. Tumor area was quantified with the Nikon Elements BR 3.0 software analyzing at low magnification (×40) 2 random fields of 2 different histologic sections (separated 600 µm from each other) per mouse. Statistical analysis was conducted using the Student t test with Welch correction for heterogeneous variances (n=33 and 12 for control and treated groups, respectively).

Figure 6A:
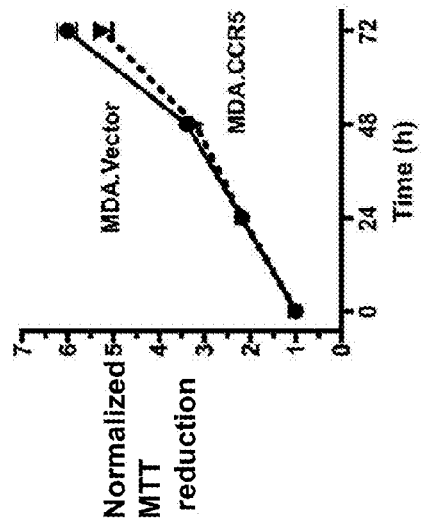
FIG. 6A, effect of CCR5 antagonist on breast cancer cell viability. MDA-MB-231 cells were exposed to increasing concentrations of maraviroc (inverted triangles) or vicriviroc (squares) for 48 hours and the cell viability was evaluated by MTT assay.
Figure 6B:
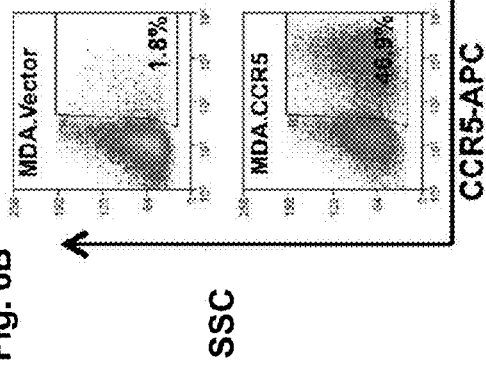
FIG. 6B illustrates flow cytometric analysis showing CCR5 expression in MDA-MB-231 cells stably transfected with pcDNA3.1$^+$/Zeo$^+$ (MDA.Vector) or human CCR5 cloned into pCDNA3$^+$Zeo$^+$ (MDA.CCR5).
Figure 6C:
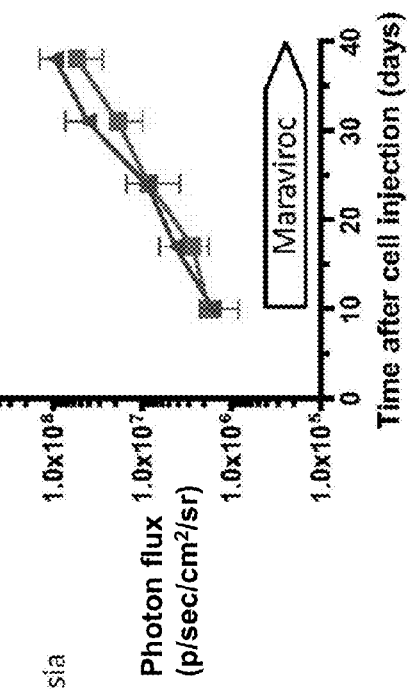
FIG. 6C illustrates a comparison of in vitro proliferation rates of MDA-MB-231 in MDA.Vector and MDA.CCR5.
Figure 6D:
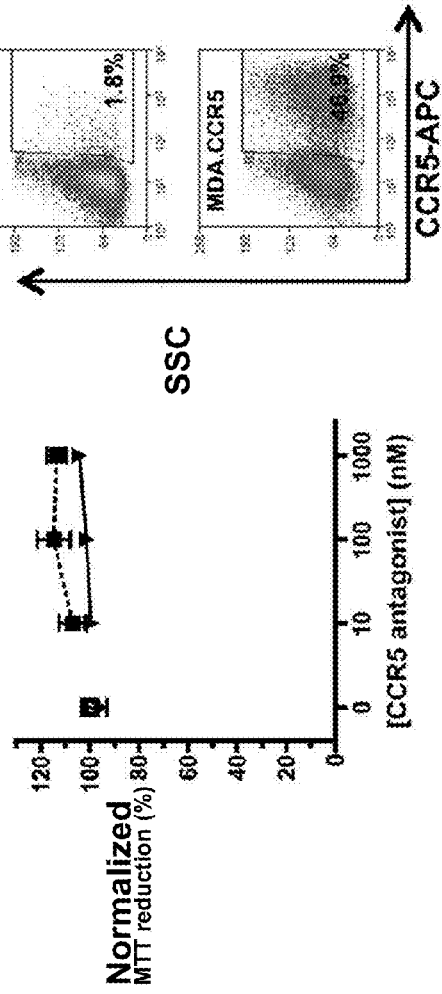
FIG. 6D illustrates evaluation of the in vivo effect of maraviroc on growth of established metastasis in mice, wherein treatment of mice was initiated 10 days after injection of MDA.pFULG cells as illustrated, and in vivo bio luminescence imaging (BLI) of the mice for evaluating the efficacy of the treatment was carried out in days: 0, 10, 17, 24, 31 and 38.
Figure 6E:
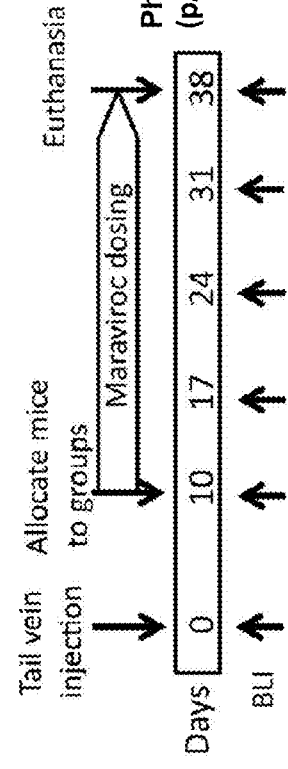
FIG. 6E illustrates quantification (mean±SEM, n=5) of in vivo BLI in the control (red/squares) and treated groups (blue/triangles) showed no differences in the growth rate.
Figure 6H:
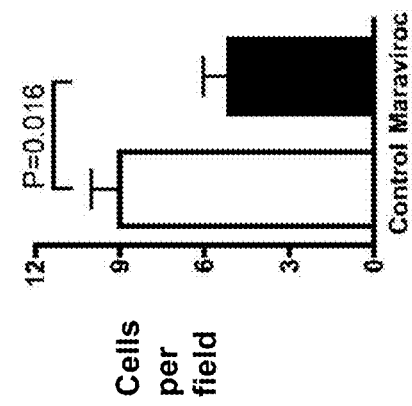
FIG. 6H illustrates quantification (H) of the number of eGFP$^+$ cells in lungs of mice 24 hours after injection of the mice with MDA.pFULG cells, wherein cells expressing eGFP were counted in 3 random fields of 2 different histologic sections (separated 700 μm from each other) per mouse (n=5 mice per group)
Figure 6F:
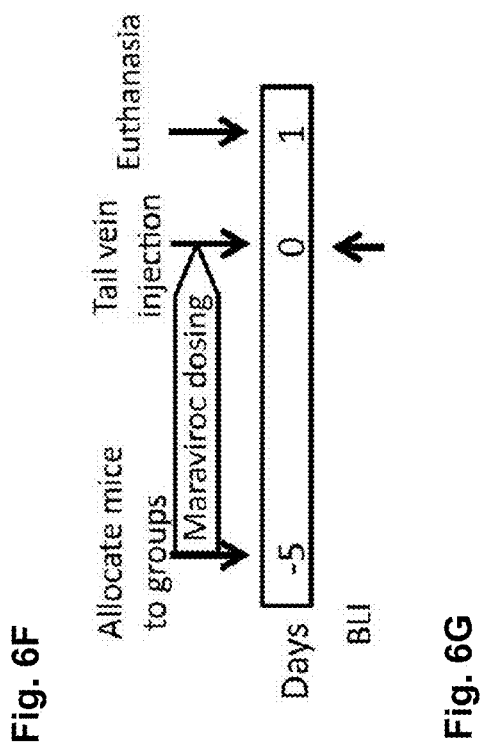
FIG. 6F illustrates an schema of the experimental design used to evaluate CCR5 role in lung colonization by MDA-MB-231 cells.
Figure 6G:
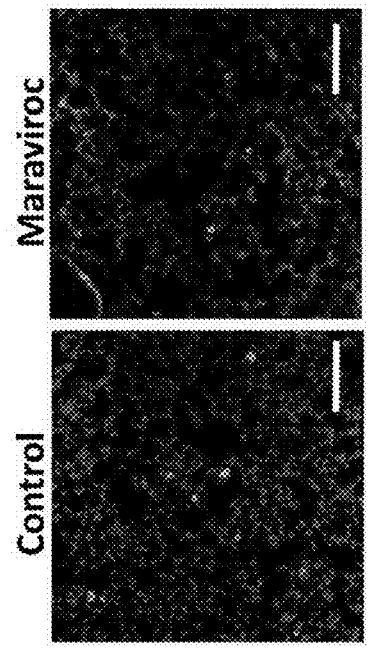
FIG. 6G illustrates exemplary confocal images of eGFP$^+$ cells in lungs of mice 24 hours after injection of the mice with MDA.pFULG cells, wherein cells expressing eGFP were counted in 3 random fields of 2 different histologic sections (separated 700 μm from each other) per mouse (n=5 mice per group)

Referring to FIGS. 6A-6H, it is shown that maraviroc reduces lung colonization but does not modify cell proliferation. In FIG. 6A, there is shown the effect of CCR5 antagonist on breast cancer cell viability. MDA-MB-231 cells were exposed to increasing concentrations of maraviroc (inverted triangles) or vicriviroc (squares) for 48 hours and the cell viability was evaluated by MTT assay. Graph is from a representative experiment carried out by sextuplicate. No statistical differences were found (ANOVA) in 3 independent experiments. In FIG. 6B, there is shown CCR5 expression in MDA-MB-231 cells stably transfected with pcDNA3.1+/Zeo+ (MDA.Vector) or human CCR5 cloned into pCDNA3+Zeo+ (MDA.CCR5). In FIG. 6C, comparison of in vitro proliferation rates of MDA. Vector versus MDA.CCR5 showed no differences (ANOVA). Representative experiment from 2 carried out by sextuplicate. In FIG. 6D, to evaluate the in vivo effect of maraviroc on growth of established metastasis, treatment of mice was initiated 10 days after injection of MDA.pFULG cells as illustrated. In FIG. 6E, quantification (mean±SEM, n=5) of in vivo BLI in the control (red/squares) and treated groups (blue/triangles) showed no differences in the growth rate. There is no effect of maraviroc of the growth rate of the tumors once established in the lungs. Thus, the reduction in tumor mass in the lungs is due to the inhibition of "homing" or spread of tumors to the lung. FIG. 6F shows schema of the experimental design used to evaluate CCR5 role in lung colonization. FIG. 6G shows representative confocal images and quantification (FIG. 6H) of the number of eGFP+ cells in lungs 24 hours after injection of MDA.pFULG cells. Cells expressing eGFP were counted in 3 random fields of 2 different histologic sections (separated 700 µm from each other) per mouse (n=5 mice per group). Statistical analysis was conducted using Student t test. Bar in micrographs, 100 µm.

Figure 7A:
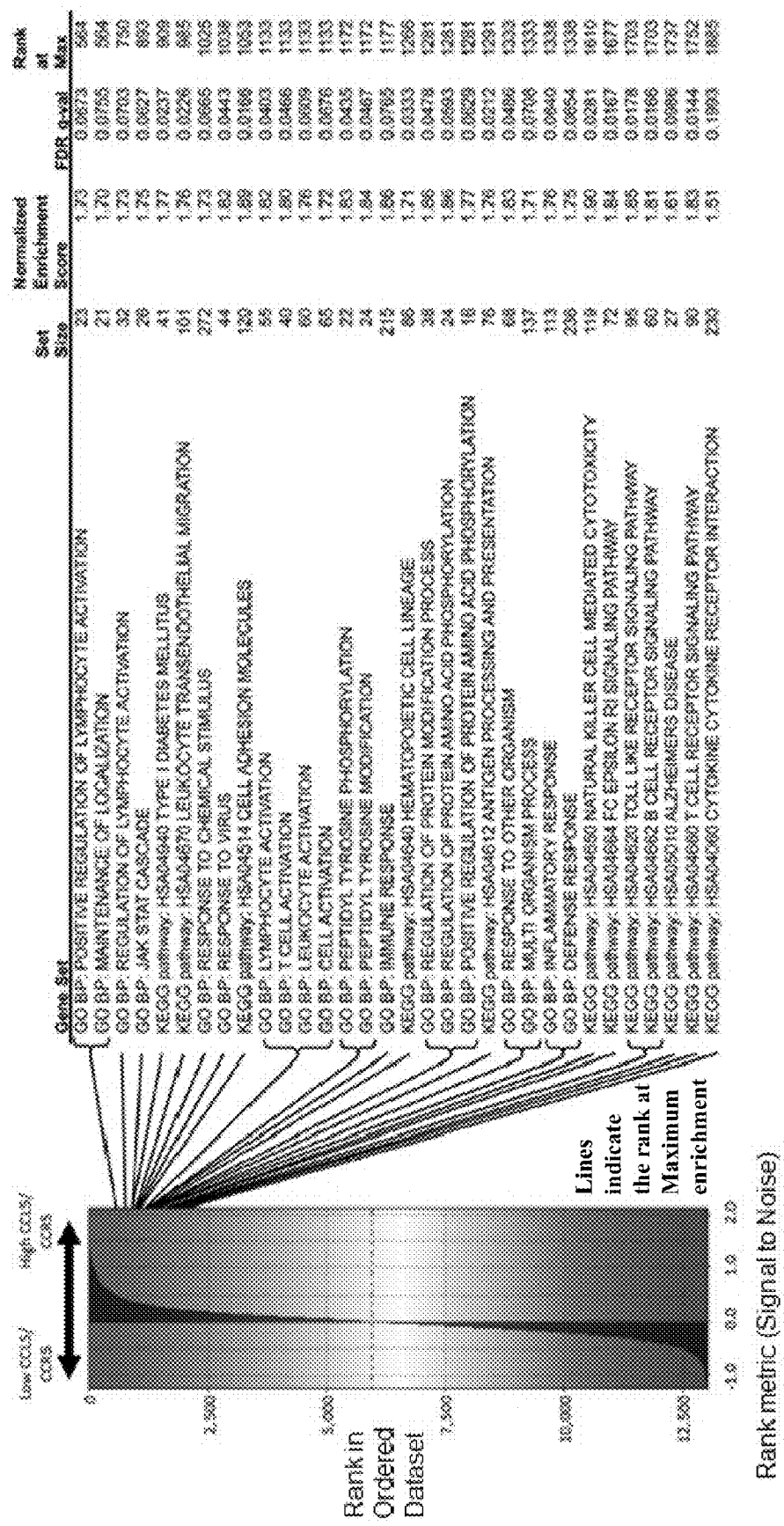
FIG. 7A illustrates GSEA analysis using KEGG and GO of tumor samples to determine the gene expression signaling pathway associated with enrichment of CCR5 and CCL5, wherein genes in the examined breast cancer dataset are ranked by a signal-to-noise metric representing their differential expression in highest 2.5% CCL5/CCR5-expressing samples versus lowest (2.5%) CCL5/CCR5 expressing samples (N=54), depicted with a color gradient, where red indicates positive correlation with CCL5/CCR5 expression and blue represents negative correlation with CCL5/CCR5 expression.

Reference is now made to FIGS. 7A1-7D2. To determine the gene expression signaling pathway associated with enrichment of CCR5 and CCL5, GSEA analysis using KEGG and GO was conducted of the tumor samples discussed herein. FIG. 7A shows the GSEA analysis. These studies showed enrichment for gene expression of pathways including lymphocyte activation, Janus-activated kinase (JAK)-STAT signaling, and Toll-like receptor activation. The receptors for CCL5 include CCR1 and CCR3. Increased expression of CCL5 associated with increased CCR1, but not CCR3, in the basal and HER-2 genetic tumor type (FIGS. 7B1-7B5 and 7C1 to 7C5). In ER-negative patients receiving chemotherapy, there was an insignificant trend toward reduced metastasis-free survival and relapse-free survival in the increased CCR5 population, compared with the population with reduced CCR5 expression (FIGS. 7D1 and 7D2).

Figure 8A:
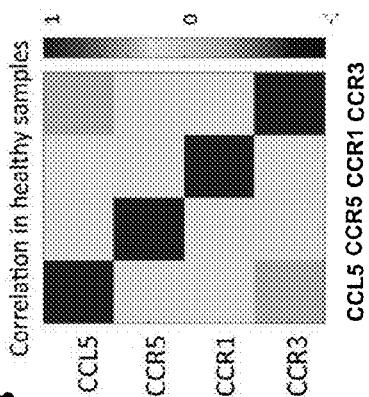
FIG. 8A illustrates heat map of CCL5 expression and its receptors CCR5, CCR1 and CCR3 in healthy population.
Figure 8B:
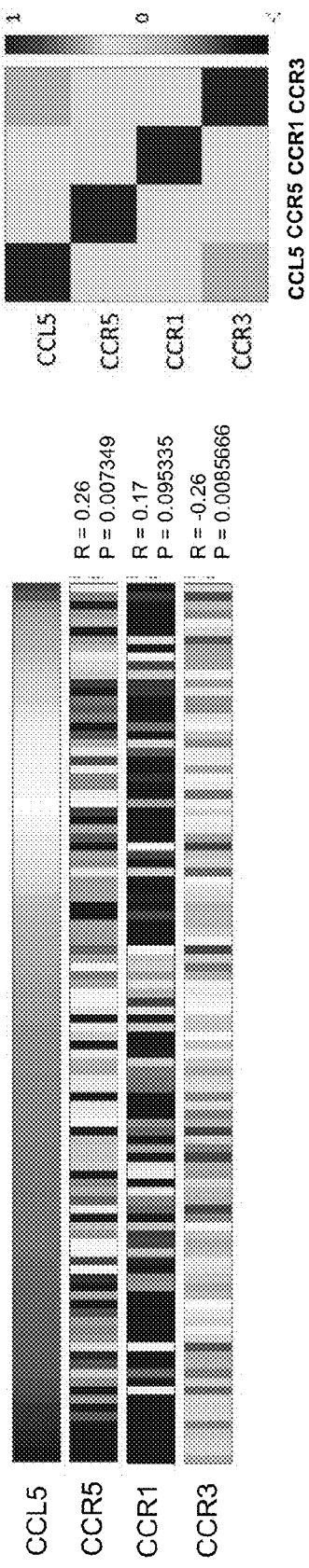
FIG. 8B illustrates heat map representing cross correlation of CCL5 expression and its receptors CCR5, CCR1 and CCR3 amongst healthy population.
Figure 8C:
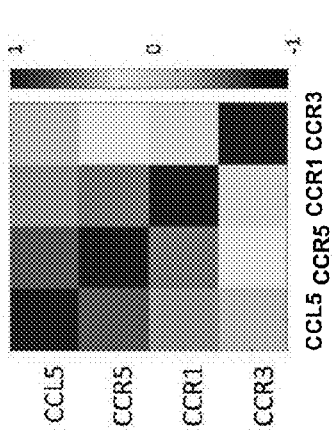
FIGS. 8C and 8D illustrate heat map representing cross correlation of CCL5 expression and its receptors CCR5, CCR1 and CCR3 amongst breast cancer patients derived from a collection of 2550 breast cancers.
Figure 8D:
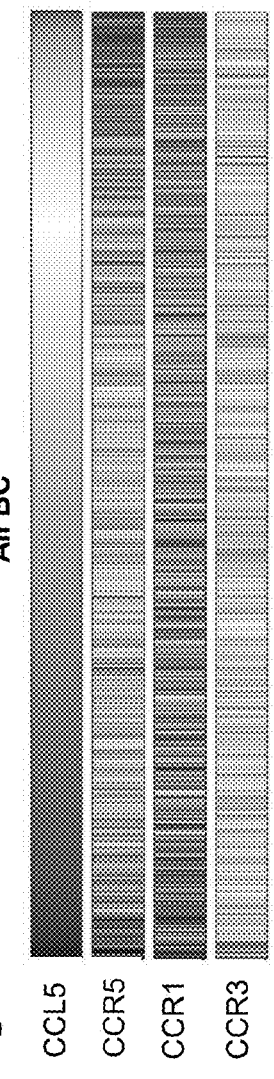

In FIGS. 8A-8D, a comparison of expression levels for CCL5 versus CCR5, CCR1, and CCR3, comparing normal breast with breast cancer showed increased correlation between receptor and ligand expression levels in tumors compared with healthy breast tissue. FIG. 8A illustrates heatmap of CCL5 expression and its receptors CCR5, CCR1 and CCR3 in healthy population. The healthy population was previously described as part of a collection of 2550 breast cancers (Ertel, A., Dean, J. L., Rui, H., Liu, C, Witkiewicz, A. K., Knudsen, K. E., and Knudsen, E. S. RB-pathway disruption in breast cancer: differential association with disease subtypes, disease-specific prognosis and therapeutic response. Cell Cycle, 9: 4153-4163, 2010.).

Referring to FIGS. 9A-9D2, three human breast cancer cell lines with a basal phenotype and molecular signature: MDA-MB-231, Hs578T, and SUM-159 (34-37) were used as models in the studies. Analysis of CCR5 expression by FACS showed that a small subpopulation of cells were positive for the receptor in all 3 cell lines (FIG. 2A for MDA-MB-231 and FIG. 9A and FIG. 9C for Hs578T and SUM-159). Because CCR5 activation induces calcium flux (38, 39), the activation of calcium signaling was assessed by CCL5. Addition of CCL5 to the cultures induced immediate calcium fluxes in a subpopulation of cells (FIG. 2B for MDA-MB-231 and FIGS. 9B and 9D for Hs578T and SUM-159), providing evidence that CCR5 is functional in basal breast cancer cells. As a positive control, the same cultures were exposed to 5% FBS (40). Calcium flux, assessed by relative fluorescence intensity, increased in more than 95% of the cells after FBS addition (FIG. 2B and FIGS. 9B, 9D1, and 9D2). To further distinguish CCL5-dependent signaling, SUM 159 cells were stably transduced with a CCR5 expression vector and the $Ca^{+2}$ response to CCL5 versus FBS was conducted (FIGS. 10C and 10D vs. FIGS. 10E and 10F). CCR5 induced $Ca^{+2}$ signaling in the CCR5-overexpressing cells, whereas both lines responded similarly to FBS induced $Ca^{+2}$ activation (FIGS. 10A1-10F).

Figure 5F:
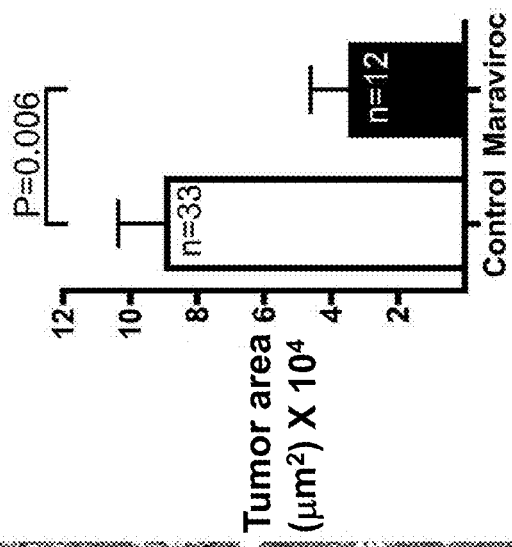
FIG. 5F shows quantification of the area covered by metastatic tumors in lung slides shown in FIG. 5E.

In view of the finding that CCR5 inhibition by CCR5 antagonists reduced calcium signaling and cell invasion, the in vivo effect of maraviroc on lung metastasis was determined. MDA-MB-231 cells were transduced within the Luc2-eGFP lentiviral vector (MDA.pFULG cells) in an experimental metastasis model. The Luc2 gene is a codon-optimized version of Luc and cells expressing this reporter were 10 to 100 times brighter than the unmodified Luc gene (30). After injection of MDA.pFULG cells into the tail vein of mice, noninvasive BLI enabled the early detection of breast cancer metastasis (41). Weekly BLI was conducted for 5 weeks and the radiance antemortem was used as a surrogate measurement of tumor burden. Mice treated with maraviroc (8 mg/kg twice daily) showed a significant reduction in both the number and the size of pulmonary metastases compared with vehicle-treated mice (FIGS. 5A and 5B, FIGS. 11A and 11B). To avoid the possibility that metastases were missed because of inappropriate imaging, ex vivo imaging, India ink staining (FIGS. 5C1 and 5C2), and histology (FIG. 5E) of the lungs were conducted. Histologic analysis corroborated that tumor burden corresponds to bioluminescence, as previously shown (30). Metastatic tumors were still detectable in 50% of the maraviroc-treated mice, but their mean size was reduced by 65% (FIGS. 5D and 5F). Interestingly, analysis of CCR5 expression in lungs from control mice showed an 8-fold enrichment of the CCR5+ fraction (FIGS. 12A to 12G). Collectively, these results provide evidence that CCR5 antagonists reduce breast cancer metastasis in vivo.

Given the aggressive clinical behavior of basal breast cancer and the lack of targeted therapies for it, the importance of the CCL5/CCR5 was evaluated in invasion and metastasis in the human breast cancer cell lines MDA-MB-231, Hs578T and SUM-159. These cell lines reflect the clinicopathologic features of the basal subtype of breast cancer (including the lack of HER-2, ER, and progesterone receptor), a basal-like molecular signature, the activation of specific signaling pathways (e.g., hypoxic or EGF receptor responses) and over expression of epithelial-mesenchymal transition proteins (FN, VIM, ad matrix metalloproteinase 2; refs. 34-37). Only a small fraction of cells within the cell lines used in this study expressed CCR5 as evaluated by FACS analysis. The studies confirmed the expression of CCR5 in MDA-MB-23 cells by reverse transcriptase PCR and showed the presence of the CCR5 protein by FACS analysis (FIGS. 13A1-13D1), and showed that CCR5 immunohistochemical staining was localized primarily to the breast cancer epithelial cell, compared with normal breast tissue (FIGS. 14A-14D).

The results disclosed herein show that CCL5 activates calcium flux in basal-like human breast cancer cells. By using the selective CCR5-antagonists maraviroc and vicriviroc (both with IC50 below 30 nmol/L; refs. 44, 45), it was shown that CCL5-activated signaling is mediated by CCR5. However, the fraction of CCL5-responsive cells (10% and 12% for MDA-MB-231 and Hs578T cells, respectively) is higher than the percentage of CCR5-expressing cells determined by FACS. This may be due to the greater sensitivity of the Ca2+ activation assays compared with the sensitivity of analysis by FACS. In addition, CCL5-induced calcium redistribution is not completely blocked by CCR5 antagonists. This may be caused by the expression of other receptors to CCL5, namely CCR1 and CCR3. CCR5 has been identified as the main CCL5 receptor in MDA-MB-231 cells (13) and CCR1 and CCR3 transcripts are absent in both MDA-MB-231 or Hs578T cell lines (8) and breast tumor samples (11). CCR1 and CCR3 were able to be detected by FACS (FIGS. 13A1-13D), suggesting a possible mechanism for the incomplete response to the CCR5 antagonist.

In one aspect, the present invention provides an in vivo method for identifying a candidate compound that down regulate expression of CCR5 and/or one or more of its ligand in tumor cells overexpressing endogenous or virally transduced oncogene selected from the group consisting of NeuT, Ha-Ras, c-Src and combinations thereof. In one embodiment, the method comprises (a) administering a candidate compound to an animal model of the tumor cells; (b) and measuring the level of CCR5 RNA or protein expression in the animal model, wherein if the level of CCR5 RNA or protein expression in the animal model is decreased compared to the level of CCR5 RNA or protein expression in untreated animal model, then the candidate compound is identified as a compound that down regulates expression of CCR5 and/or one or more of its ligand in tumor cells overexpressing endogenous or virally transduced oncogene selected from the group consisting of NeuT, Ha-Ras, c-Src and combinations thereof. In one embodiment, the tumor cells comprise mammalian prostate cancer cells. In one embodiment, tumor cells comprise mammalian prostate cancer cell line having at least one or more of a set of primary mammalian epithelial cells which have been infected with a retroviral vector carrying an oncogene selected from the group consisting of NeuT, Ha-Ras, c-Src and combinations thereof.

An exemplary mammalian prostate cancer cell lines suitable for use in the present invention include, but are not limited to, mammalian prostate cancer cell lines disclosed in U.S. Provisional Patent Application No. 61/646,586, filed May 14, 2012, whose contents are incorporated by reference herein in their entirety. In one embodiment, the mammalian prostate cancer cell line comprises at least one or more of a set of primary mammalian epithelial cells which have been infected with a retroviral vector carrying an oncogene. In one embodiment, the oncogene is selected from the group consisting of c-Myc, Ha-Ras, NeuT, c-Src and combinations thereof. In one embodiment of the mammalian prostate cancer cell line, an oncogene selected from the group consisting of c-Myc, Ha-Ras, NeuT, c-Src and combinations thereof is expressed. The mammalian prostate cancer cell line can include any suitable mammalian cell, including primary murine epithelial cells. In some embodiments, the primary mammalian epithelial cells are derived from any immune competent mammal. In one embodiment, the primary mammalian epithelial cells are derived from an immune competent mammal selected from the group consisting of rodents, including rats and mice.

In some embodiments, the suitable animal model of cancer comprises an immune competent mammal implanted with a cancer cell line transformed with one or more of a set of oncogenes selected from the group consisting of c-Myc, Ha-Ras, NeuT, c-Src and combinations thereof. In one embodiment, the animal model of cancer is an immunocompetent transgenic mouse created using the mammalian prostate cancer cell line of the present invention develops a prostate tumor capable of producing a detectable molecular genetic signature based on an expression level of one or more of a set of oncogenes selected from the group consisting of c-Myc, Ha-Ras, NeuT, c-Src and combinations thereof.

In some embodiments, the suitable animal model of cancer is produced by an in vitro method. In one embodiment, in vitro method for producing the suitable animal model includes production of immortalized primary mammalian epithelial cells. In one embodiment, the method for the in vitro production of immortalized primary mammalian epithelial cells, comprises infecting primary mammalian epithelial cells with a retroviral vector carrying an oncogene selected from the group consisting of c-Myc, Ha-Ras, NeuT, c-Src and combinations thereof to provide infected cells, wherein the primary mammalian epithelial cells are capable of being infected by said retroviral vector and under conditions whereby the c-Myc, Ha-Ras, NeuT, c-Src and combinations thereof are expressed in said infected cells.

I. EXAMPLES

A. Materials and Methods

A.1. Breast Cancer Patients Data Set and Statistical Analysis

A microarray data set that was previously compiled (21) from the public repositories Gene Expression Omnibus (23) and ArrayExpress (24) was used to evaluate CCR5 and CCL5 expression in the context of clinical samples. Samples in this data set were assigned to 5 canonical breast cancer subtypes, including luminal A, luminal B, normal-like, basal, and HER-2-overexpressing disease. The classification of microarray samples among these 5 subtypes was achieved by computing their correlation against an expression profile centroid representative of each subtype and assigning samples to the subtype with the highest corresponding correlation coefficient (25). Samples with a maximum correlation coefficient below 0.3 were considered unclassified. Analysis of CCL5 and CCR5 transcript was then conducted specifically among the luminal A, luminal B, basal, normal-like, and HER-2 subtypes. Differential expression of the averaged gene signature magnitude among these sample subsets was evaluated using 2-tailed Student t test. Kaplan-Meier analysis was used to evaluate survival trends within the sample subsets. Scatter plots of CCL5 versus CCR5 samples were also generated to observe coregulation patterns specific to each subtype. For these scatter plots, gene profiles were median-centered and scaled to unitary SD.

A.2. Cell Lines and Cell Culture

MDA-MB-231, MCF-7, and Hs578T cells were maintained in Dulbecco's Modified Eagle's Medium (DMEM) supplemented with 10% FBS. SUM-159 cells (kindly provided by Dr. Stephen Ethier, Wayne State University, Detroit, Mich.) were maintained in Ham's F-12 supplemented with 4 µg/mL of insulin, 1 µg/mL of hydrocortisone, and 5% FBS. Oncogene-transformed derivatives of MCF-10A cells (MCF10A-NeuT, MCF10A-Src, and MCF10A-Ras; ref. 26) were maintained in DMEM:Ham's F-12 (50 of 50) supplemented with 4 mg/mL of insulin, 10 ng/mL of EGF, and 1 mg/mL of hydrocortisone. A total of 100 µg/mL of each penicillin and streptomycin were included in all media. Cells were cultured in 5% $CO_2$ at 37° C. For in vitro treatments, maraviroc was dissolved in dimethyl sulfoxide (DMSO) and diluted in culture medium. The final concentration of DMSO in treated and control cultures was 0.5%. Vicriviroc was dissolved in culture medium.

A.3. Fluorescence-Activated Cell-Sorting Analysis

Cell labeling and fluorescence-activated cell-sorting (FACS) analysis for CCR5 were based on prior publications (27) with minor modifications. Before labeling, the cells were blocked with normal mouse IgG (1 of 100) and purified rat anti-mouse Fcγ III/II receptor antibody (1 of 100; Pharmingen) for 30 minutes and then incubated with allophycocyanin (APC)-labeled CCR5 antibody (R&D Systems). All experiments were conducted at 4° C. Sample analysis was conducted on FACSCalibur flow cytometer (BD Biosciences). These data were analyzed with FlowJo software (Tree Star, Inc.).

A.4. Invasion Assay

The 3-dimensional invasion assay was conducted as previously reported (12). Briefly, 100 µL of 1.67 mg/mL Rat Tail collagen type I (BD Biosciences) was pipetted into the top chamber of a 24-well 8-µm pore Transwell (Corning). The Transwell was incubated at 37° C. overnight to allow the collagen to solidify. A total of 30,000 cells were then seeded on the bottom of the Transwell membrane and allowed to attach. Serum-free growth medium was placed into the bottom chamber, whereas 15 ng/mL CCL5 or 5% FBS was used as a chemoattractant in the medium of the upper chamber. The cells were then chemoattracted across the filter through the collagen above for 3 days. Cells were fixed in 4% formaldehyde, permeabilized with 0.2% Triton-X in PBS, and then stained with 40 µg/mL propidium iodide (PI) for 2 hours. Fluorescence was analyzed by confocal z-sections (one section every 20 µm) at ×10 magnification from the bottom of the filter using a Zeiss LSM 510 Meta inverted confocal microscope at the Kimmel Cancer Center Bioimaging Facility.

A.5. Intracellular Calcium Assay

Calcium responses induced either by CCL5 or FBS in human cancer cell lines were monitored under fluorescence confocal microscope as previously reported (28). Briefly, breast cancer cells were seeded in 4-well labtek chambers (Nunc) at $10^4$ cells/cm$^2$ and incubated for 1 day. After 12-hour starvation, cells were labeled by incubating them with 2 mmol/L Fluo-4-AM (Molecular Probes) in HBSS for 30 minutes, washed twice, and incubated for additional 30 minutes before imaging under the microscope. Time-lapse images were collected using a Zeiss LSM 510 Meta inverted confocal microscope with the incubator at 37° C. Relative intracellular $Ca^{2+}$ concentration was determined by the changes in fluorescent intensity (FI) of Fluo-4-AM upon the addition of CCL5 (60 ng/mL) or FBS (5%) and was calculated as $(FI_t-FI_0)/FI_0$.

A.6. MTT Assay

The MTT assay is a colorimetric assay for measuring the activity of cellular enzymes that reduce the tetrazolium dye, 3-(4,5-Dimethylthiazol-2-yl)-2,5-diphenyltetrazolium bromide, a yellow tetrazole (MTT), to its insoluble formazan, giving a purple color. These assay measures cellular metabolic activity via NAD(P)H-dependent cellular oxidoreductase enzymes and may, under defined conditions, reflect the number of viable cells (cell proliferation). Tetrazolium dye assay can also be used to measure cytotoxicity (loss of viable cells) or cytostatic activity (shift from proliferative to resting status) of potential medicinal agents and toxic materials. MTT Assay usually done in the dark because MTT reagent is sensitive to light.

The effects of CCR5 antagonists on cell viability and proliferation rate were estimated using the soluble tetrazolium salt MTT assay (29). MTT is reduced by the mitochondria of viable cells, and the amount of reduced formazan is proportional to the number of viable cells. After 72 hours of exposure to the drugs, cells were incubated with 1 mg/mL of MTT for 90 minutes. Then, the reduced (insoluble and colored) formazan was dissolved in DMSO and measured spectrophotometrically at 570 nm. The effect of CCR5 over expression in breast cancer cell proliferation was studied in MDA-MB-231 cells transfected with full-length human CCR5 subcloned into pcDNA3.1$^+$/Zeo$^+$ vector (kindly provided by Dr. Eleanor Fish, University of Toronto, Toronto, ON, Canada) and selected with Zeocin (200 µg/mL) as previously described (18). MTT assays were conducted in sextuplicate using 96-well microplates.

A.7. Viral Cell Transduction

A lentiviral vector encoding firefly luciferase 2 (Luc2)-eGFP fusion protein was a generous gift from Dr. Sanjiv S. Gambhir (School of Medicine, Stanford University, Stanford, Calif.; ref. 30). Lentivirus propagation was conducted following the protocol described by Zahler and colleagues (31). Breast cancer cell lines were transduced at a multiplicity of infection of 20 in the presence of 8 mg/mL polybrene (Sigma) for 24 hours (30, 31).

A.8. Experimental Metastasis Assay and Bioluminescence Imaging

MB-MDA-231 cells expressing Luc2-eGFP (called MDA.pFLUG for the rest of the article) were detached with a nonenzymatic cell dissociation buffer (4 mmol/L EDTA in Ca and $Mg^{2+}$-free PBS), resuspended in Dulbecco's PBS without $Ca^{2+}$ and $Mg^{2+}$ and immediately injected into the tail vein of 8-week-old, female nonobese diabetic/severe combined immunodeficient (NOD/SCID) mice (NCI, Bethesda Md.). Each mouse received $10^6$ cells. Mice were treated by oral gavage with maraviroc (8 mg/kg every 12 hours) or vehicle (5% DMSO in acidified water; ref. 32).

Treatment was started immediately after injection or 10 days later for the experiments analyzing the proliferation of established metastasis. For in vivo bioluminescence imaging (BL1), mice were given an intraperitoneal (i.p.) injection with 200 μL of d-luciferin (30 mg/mL). Mice were anesthetized with isoflurane (2% in 1 L/min oxygen), and bioluminescence images were acquired 10 to 15 minutes after d-luciferin injection using the IVIS XR system (Caliper Life Sciences). Acquisition times ranged from 10 seconds (for later time points) to 5 minutes (for early time points). Data are expressed as total photon flux and were analyzed using Living Image 3.0 software (Caliper Life Sciences). For ex vivo BLI, d-luciferin was diluted in PBS to a final concentration of 300 μg/mL and used to soak freshly isolated lungs for 2 to 3 minutes before imaging. Some lungs were stained with India ink, as previously reported (33), or processed and stained with hematoxylin and eosin to corroborate the presence of pulmonary tumors. For homing assays, mice were euthanized 24 hours after the intravenous injection of MDA.pFULG cells. Lungs were perfused with PBS, fixed with freshly prepared formaldehyde (4% in PBS), and frozen in optimum cutting temperature (Sakura Finetek). Cryosections (10 μm) were counterstained with 4',6-diamidino-2-phenylindole analyzed by confocal microscopy. Animal experiments were approved by the Thomas Jefferson University's Institutional Animal Care and Use Committee.

A.9. Reagents And Antibodies

CCL5 (catalog no. 278-RN) and anti-CCR5 APC antibody (catalog no. FAB 1802A) were purchased from R&D Systems. A rabbit anti-human CCR5 polyclonal antibody (GenScipt; catalog no. A00979) was used for immunohistochemical staining. Rat tail collagen type I was purchased from BD Biosciences. Vicriviroc and maraviroc were obtained from Selleck Chemicals. Luciferin was obtained from Gold Biotechnology.

B. Results

B.1. Active CCL5/CCR5 Signaling in Basal Breast Cancer

To examine the relative abundance of CCL5 and its receptor CCR5 by genetic subtype, interrogation was conducted within a combined microarray database comprising 2,254 human breast cancer samples from 27 independent studies (21). The relative abundances of CCL5 and CCR5 were significantly increased in the basal and HER-2 subtypes compared with the normal-like, luminal A and luminal B subtypes (FIG. 1A). The increased expression of CCL5 and CCR5 correlated positively in individual breast cancer samples and the correlation was highly significant in the basal and HER-2 subtypes (FIGS. 1B1 to 1B5). The proportion of patients with a CCL5/CCR5-positive signature was more than 58% in the basal and HER-2 subtypes (FIG. 1C). In agreement with previous reports, clinical information of the cases in this database showed that the probability to develop metastasis is increased in the basal, luminal B, and HER-2 subtypes (FIG. 1D).

To determine the gene expression signaling pathway associated with enrichment of CCR5 and CCL5, GSEA analysis using KEGG and GO was conducted of these tumor samples (FIG. 7A). These studies showed enrichment for gene expression of pathways including lymphocyte activation, Janus-activated kinase (JAK)-STAT signaling, and Toll-like receptor activation (FIG. 7A). The receptors for CCL5 include CCR1 and CCR3. Increased expression of CCL5 associated with increased CCR1, but not CCR3, in the basal and HER-2 genetic tumor type (FIGS. 7B1 to 7B5 and 7C1 to 7C5). In ER-negative patients receiving chemotherapy, there was an insignificant trend toward reduced metastasis-free survival and relapse-free survival in the increased CCR5 population, compared with the population with reduced CCR5 expression (FIGS. 7D1 and 7D2). A comparison of expression levels for CCL5 versus CCR5, CCR1, and CCR3, comparing normal breast with breast cancer showed increased correlation between receptor and ligand expression levels in tumors compared with healthy breast tissue (FIG. 8A).

B.2. Ccl5 Promotes Breast Cancer $Ca^{2+}$ Signaling and Cellular Invasion

Figure 10B:
FIG. 10B illustrates schematic representation of the timeline for induction of calcium signaling in which CCL5 is added to the SUM159-vector control cells or the SUM 159 cells stably overexpressing the CCR5 receptor at 60 seconds and FBS is added at 320 seconds.
Figure 10C:
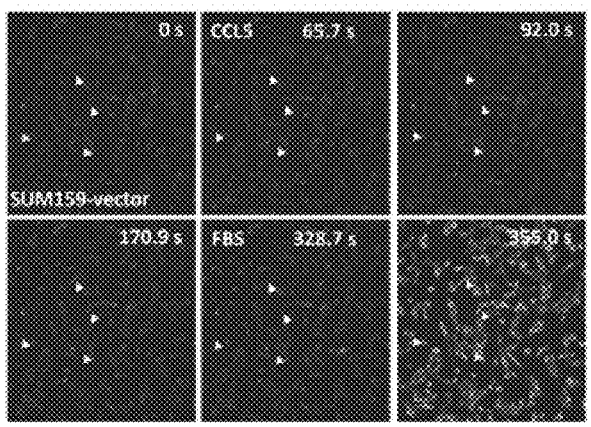
FIG. 10C illustrates induction of calcium signaling (the $Ca^{+2}$ response to CCL5 versus FBS) in the SUM159-vector control cells loaded with Fluo-4-AM before and upon the addition of CCL5 or FBS.
Figure 10D:
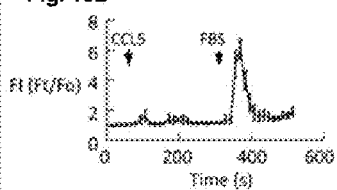
FIG. 10D illustrates the average fluorescence for the population of SUM159-vector control cells.
Figure 10E:
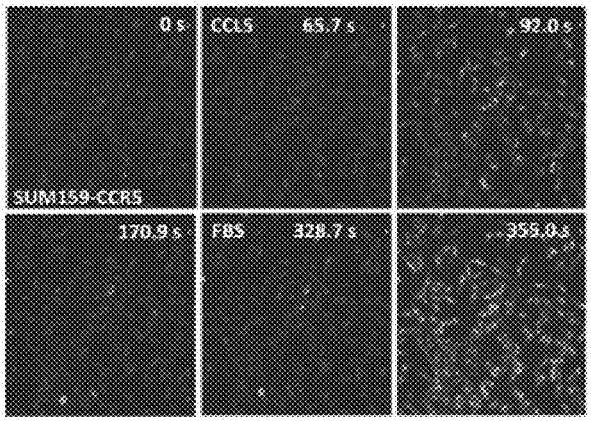
FIG. 10E illustrates induction of calcium signaling (the $Ca^{+2}$ response to CCL5 versus FBS) in the SUM 159 cells stably overexpressing the CCR5 receptor at 60 seconds and FBS is added at 320 second.
Figure 10F:
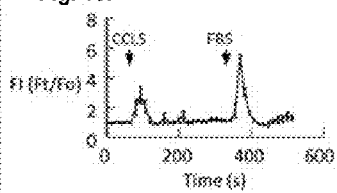
FIG. 10F illustrates the average fluorescence for the population of SUM159-CCR5 cells.

Three human breast cancer cell lines with a basal phenotype and molecular signature: MDA-MB-231, Hs578T, and SUM-159 (34-37) were used as models in the studies described herein. Analysis of CCR5 expression by FACS showed that a small subpopulation of cells were positive for the receptor in all 3 cell lines (FIG. 2A for MDA-MB-231 and FIGS. 9A and 9C for Hs578T and SUM-159). Because CCR5 activation induces calcium flux (38, 39), the activation of calcium signaling was assessed by CCL5. Addition of CCL5 to the cultures induced immediate calcium fluxes in a subpopulation of cells (FIG. 2B for MDA-MB-231 and FIGS. 9B1/9B2 and 9D1/9D2 for Hs578T and SUM-159), providing evidence that CCR5 is functional in basal breast cancer cells. As a positive control, the same cultures were exposed to 5% FBS (40). Calcium flux, assessed by relative fluorescence intensity, increased in more than 95% of the cells after FBS addition (FIG. 2B1/2B2 and FIGS. 9B1/9B2 and 9D1/9D2). To further distinguish CCL5-dependent signaling, SUM159 cells were stably transduced with a CCR5 expression vector and the $Ca^{+2}$ response to CCL5 versus FBS was conducted (FIGS. 10C and 10D vs. 10E and 10F). CCR5 induced $Ca^{+2}$ signaling in the CCR5-overexpressing cells, whereas both lines responded similarly to FBS induced $Ca^{+2}$ activation (FIGS. 10A1-10F).

Next, the effect of CCR5 activation on breast cancer cell invasion was assessed using 3D migration assays. CCL5 induced invasion of the basal MDA-MB-231, Hs578T, SUM-159 but not the luminal MCF-7 cells (FIGS. 2C and 2D). CCL5 promoted invasion of MCF-10A cells engineered to express either NeuT, H-Ras, or c-Src oncogenes, compared with MCF10A vector-transduced cells (FIGS. 2E and 2F), suggesting that CCL5 responsiveness may be acquired during transformation and requires specific cooperative oncogenic signals. The finding that CCL5 induced cellular invasion led us to examine the migratory capacity of CCR5$^+$ cells versus that of CCR5$^-$ cells. Within the same SUM-159 breast cancer cell line, CCR5$^+$ cells showed an approximately 40-fold greater cellular invasiveness (FIGS. 2G and 2H), indicating that the expression of CCR5 correlates with a proinvasive phenotype.

B.3. CCR5 Antagonists Block Breast Cancer Calcium Signaling and Cell Invasion

The importance of CCR5 in HIV infection led to the development of different drugs that target this receptor. Therefore, examination of whether the CCR5 antagonists maraviroc and vicriviroc were capable of blocking the CCL5/CCR5 signaling in basal breast cancer cells were conducted. Both CCR5 antagonists blocked CCL5-induced calcium mobilization. In MDA-MB-231 cells, maraviroc and vicriviroc inhibited calcium responses by 65% and 90%, respectively (FIGS. 3A and 3B). Similar observations were made with both drugs in Hs578T cells (FIGS. 3C1 to 3C4 and 3D), indicating that CCR5 expressed in different basal breast cancer cells is sensitive to pharmacologic inhibition.

To evaluate the functional relevance of CCR5 in cellular migration and invasion, the effects of maraviroc and vicriviroc were tested in 3D invasion assays. Using 2 different cell lines, it was found that both CCR5 antagonists inhibited FBS-induced breast cancer cell invasion at the clinically relevant concentration of 100 nmol/L (FIGS. 4A-4D). Thus, the proinvasive effect of CCR5 can be abrogated by using specific antagonists.

B.4. CCR5 Inhibition Blocks Breast Cancer Metastasis In Vivo

In view of the finding that CCR5 inhibition by CCR5 antagonists reduced calcium signaling and cell invasion, the in vivo effect of maraviroc on lung metastasis was determined. MDA-MB-231 cells transduced within the Luc2-eGFP lentiviral vector (MDA.pFULG cells) were used in an experimental metastasis model. The Luc2 gene is a codon-optimized version of Luc and cells expressing this reporter were 10 to 100 times brighter than the unmodified Luc gene (30). After injection of MDA.pFULG cells into the tail vein of mice, noninvasive BLI enabled the early detection of breast cancer metastasis (41). Weekly BLI was conducted for 5 weeks and the radiance antemortem was used as a surrogate measurement of tumor burden. Mice treated with maraviroc (8 mg/kg twice daily) showed a significant reduction in both the number and the size of pulmonary metastases compared with vehicle-treated mice (FIGS. 5A and B, FIGS. 11A and 11B). To avoid the possibility that metastases were missed because of inappropriate imaging, ex vivo imaging, India ink staining (FIGS. 5C1 and 5C2), and histology (FIG. 5E) of the lungs were conducted. Histologic analysis corroborated that tumor burden corresponds to bioluminescence, as previously shown (30). Metastatic tumors were still detectable in 50% of the maraviroc-treated mice, but their mean size was reduced by 65% (FIGS. 5D and 5F). Interestingly, analysis of CCR5 expression in lungs from control mice showed an 8-fold enrichment of the CCR5$^+$ fraction (FIGS. 12A to 12G). Collectively, these results provide evidence that CCR5 antagonists reduce breast cancer metastasis in vivo.

B.5. CCR5 Antagonist Impairs Lung Colonization But Not Cell Proliferation or Tumor Growth It was determined whether the reduction in metastatic tumors by maraviroc involved changes in cellular proliferation and/or target organ colonization. The effect of CCR5 inhibition on cell viability and proliferation both in vitro and in vivo was analyzed. Maraviroc or vicriviroc treatment of MDA-MB-231 cells for 48 hours did not affect the MTT reduction, which was used as a surrogate measurement of cancer cell number (FIG. 6A). In agreement, over expression of CCR5 in MDA-MB-231 cells did not modify their proliferation rate compared with cells transfected with the empty vector (FIGS. 6B and 6C). Finally, maraviroc treatment of mice with established pulmonary metastasis did not modify tumor growth (FIGS. 6D and 6E), indicating that CCR5 activation does not promote the proliferation of basal breast cancer cells in vitro nor in the pulmonary microenvironment of immunocompromised mice.

On a different in vivo experiment, the effect of maraviroc on breast cancer cell homing to lungs was examined. To reach a steady-state concentration in plasma and tissues, mice were given 10 administrations of maraviroc (twice a day for 5 days) before the intravenous injection of MDA.pFULG cells (FIG. 6F). Inoculation of equal numbers of MDA.pFULG cells in control and treated groups was corroborated by BLI immediately after injection. Maraviroc reduced the number of eGFP$^+$ cells in the lungs by 40% (FIGS. 6G and 6H), suggesting that the in vivo antimetastatic effect of maraviroc is caused by a reduction in the number of cancer cells that colonize the target organ from the circulation.

C. Discussion

The current studies show for the first time that: (i) enrichment of CCL5/CCR5 expression occurs in patients with basal and Her2 positive genetic subtypes of breast cancer; (ii) oncogenic transformation of immortalized human breast cells by distinct oncogenes induces CCL5 responsiveness; and (iii) maraviroc, an FDA-approved drug for the treatment of CCR5-trophic HIV infection, reduce metastatic tumor burden in vivo.

Previous studies showed that CCL5 levels are elevated in breast primary and metastatic tumors (9-11), suggesting a role of CCL5 in the acquisition of malignancy. The present disclosure show that increased expression of CCL5 and CCR5 are associated and that CCL5/CCR5 expression levels are different among the different genetic subtypes of breast cancer. Increased expression of CCL5 and CCR5 is found in the basal and HER-2 subtypes. In agreement, increased CCL5 expression has been found predominantly in ER-negative patients (42). Increased CCL5 also correlated with increased CCR1 in basal and Her2 genetic subtypes of breast cancer. A trend toward reduced metastasis-free survival and relapse-free survival was observed among the CCR5-overexpressing tumors in patients who received chemotherapy.

Given the aggressive clinical behavior of basal breast cancer and the lack of targeted therapies for it, the importance of the CCL5/CCR5 axis in invasion and metastasis was evaluated in the human breast cancer cell lines MDA-MB-231, Hs578T and SUM-159. These cell lines reflect the clinicopathologic features of the basal subtype of breast cancer (including the lack of HER-2, ER, and progesterone receptor), a basal-like molecular signature, the activation of specific signaling pathways (e.g., hypoxic or EGF receptor responses) and over expression of epithelial-mesenchymal transition proteins (FN, VIM, and matrix metalloproteinase 2; refs. 34-37). Only a small fraction of cells within the cell lines used in this study expressed CCR5 as evaluated by FACS analysis. Our findings are consistent with studies by Müller and colleagues who showed CCR5 expression in MDA-MB-231 by quantitative real-time PCR (8). These studies confirmed the expression of CCR5 in MDA-MB-23 cells by reverse transcriptase PCR and showed the presence of the CCR5 protein by FACS analysis (FIGS. 13A1-13D), and showed that CCR5 immunohistochemical staining was localized primarily to the breast cancer epithelial cell, compared with normal breast tissue (FIGS. 14A-14D).

The results herein show that CCL5 activates calcium flux in basal-like human breast cancer cells, as previously described in cells of the immune system (39, 43) and CCR5-transfected cells (27, 44, 45). By using the selective CCR5-antagonists maraviroc and vicriviroc (both with $IC_{50}$ below 30 nmol/L; refs. 44, 45), it was shown that CCL5-activated signaling is mediated by CCR5. However, the fraction of CCL5-responsive cells (10% and 12% for MDA-MB-231 and Hs578T cells, respectively) is higher than the percentage of CCR5-expressing cells determined by FACS. This may be due to the greater sensitivity of the $Ca^{2+}$ activation assays compared with the sensitivity of analysis by FACS. In addition, CCL5-induced calcium redistribution is not completely blocked by CCR5 antagonists. This may be caused by the expression of other receptors to CCL5, namely CCR1 and CCR3. CCR5 has been identified as the main CCL5 receptor in MDA-MB-231 cells (13) and CCR1 and CCR3 transcripts are absent in both MDA-MB-231 or Hs578T cell lines (8) and breast tumor samples (11). CCR1 and CCR3 were able to be detected by FACS (FIGS.

13A1-13D), suggesting a possible mechanism for the incomplete response to the CCR5 antagonist.

It was observed that the subpopulation of CCR5+ cells displayed increased invasiveness, indicating that CCR5 favors cell migration and invasion in basal-like breast cancer cells. The failure of luminal-like MCF-7 cells to respond to CCL5 is in agreement with previous publications (12). These studies also showed that CCR5 inhibition with either maraviroc or vicriviroc reduced in vitro FBS-induced breast cancer cellular invasion without affecting cellular viability. The finding that CCR5 antagonists block FBS-induced invasion is novel and suggested that CCR5 activation contribute to the production of metastasis in vivo where different chemotactic and growth signals are present. The mechanisms involved in CCR5 regulation of FBS-activated invasiveness are uncharacterized but they may include heterodimerization and ligand affinity regulation of other GPCRs (46), or the transactivation of growth factor receptor (47) or integrin-mediated signaling (48), as described in noncancerous cells.

The in vivo antimetastatic effect of maraviroc was shown by injecting MDA.pFULG cells into the circulation of immunodeficient mice and treating them with clinically relevant doses of the drug. In humans, oral doses of 300 mg produce an average $C_{max}$ of 1,200 nmol/L (49), whereas in mice 16 mg/kg produce an average $C_{max}$ of 1,045 nmol/L (32). Because the drug is taken twice a day in the clinical setting, 16 mg/kg/d divided into 2 doses and administered during the experiments described herein. Maraviroc significantly reduced the pulmonary tumor burden. Although it has been proposed that pharmacologic CCR5 inhibition may be beneficial for patients with breast cancer, to our knowledge this is the first study showing that systemic administration of a CCR5 antagonist reduces metastatic colonization of basal breast cancer cells.

The antimetastatic effect of maraviroc is not caused by alterations in growth of established metastasis. CCR5 activation by CCL5 drives proliferation in CCR5-transfected MCF-7 breast cancer cells (18) and prostate cancer cells (50), but this study and others (13) showed that the CCL5/CCR5 axis does not play a role in cell proliferation or survival in the basal-like MDA-MB-231 cells. Furthermore, inhibition of CCR5 surface expression through a dominant-negative form of CCR5 (CCR5Δ32) in MDA-MB-231 cells does not change in vivo proliferation or apoptotic response (17). On the other hand, it was found that maraviroc reduced lung colonization by MDA.pFULG cancer cells. This result is consistent with previous studies in which inhibition of CCR5 expression within breast cancer cells or administration of anti-CCL5 neutralizing antibody to tumor-bearing mice reduced the enhanced metastatic capability induced by coinjection of mesenchymal stem cells (MSC; ref. 13). The authors identified cancer cell extravasation as the crucial metastatic step affected by CCL5/CCR5 inhibition (13). Together, these data support a role for CCR5 antagonists in blocking the ability of basal breast cancer cells to reach the metastatic sites instead of inhibiting their proliferation or survival after arrival. Blocking the homing of cancer cells to metastatic sites is a desirable characteristic in a true antimetastatic drug (51). Therefore, CCR5 antagonists may be useful as adjuvant therapy for breast basal tumors with CCR5 over expression or other tumor types where CCR5 promotes metastasis, such as prostate cancer (50) or gastric cancer (52).

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

All references, including publications, patent applications, and patents, cited herein are hereby incorporated by reference to the same extent as if each reference were individually and specifically indicated to be incorporated by reference and were set forth in its entirety herein.

II. REFERENCES

1. Parkin D M, Fernandez L M. Use of statistics to assess the global burden of breast cancer. Breast J 2006; 12 Suppl 1: S70-80.
2. Group EBCTC. Effects of chemotherapy and hormonal therapy for early breast cancer on recurrence and 15-year survival: an overview of the randomised trials. Lancet 2005; 365: 1687-717.
3. Meyers M O, Klauber-Demore N, Ollila D W, Amos K D, Moore D T, Drobish A A, et al. Impact of breast cancer molecular subtypes on locoregional recurrence in patients treated with neoadjuvant chemotherapy for locally advanced breast cancer. Ann Surg Oncol 2011; 18:2851-7.
4. Kennecke H, Yerushalmi R, Woods R, Cheang M C, Voduc D, Speers C H, et al. Metastatic behavior of breast cancer subtypes. J Clin Oncol 2010; 28: 3271-7.
5. Perou C M, Sorlie T, Eisen M B, van de Rijn M, Jeffrey S S, Rees C A, et al. Molecular portraits of human breast tumours. Nature 2000; 406: 747-52.
6. Reis-Filho J S, Lakhani S R. Breast cancer special types: why bother? J Pathol 2008; 216: 394-8.
7. Kakinuma T, Hwang S T. Chemokines, chemokine receptors, and cancer metastasis. J Leukoc Biol 2006; 79: 639-51.
8. Muller A, Homey B, Soto H, Ge N, Catron D, Buchanan M E, et al. Involvement of chemokine receptors in breast cancer metastasis. Nature 2001; 410: 50-6.
9. Luboshits G, Shina S, Kaplan O, Engelberg S, Nass D, Lifshitz-Mercer B, et al. Elevated expression of the CC chemokine regulated on activation, normal T cell expressed and secreted (RANTES) in advanced breast carcinoma. Cancer Res 1999; 59: 4681-7.
10. Niwa Y, Akamatsu H, Niwa H, Sumi H, Ozaki Y, Abe A. Correlation of tissue and plasma RANTES levels with disease course in patients with breast or cervical cancer. Clin Cancer Res 2001; 7:285-9.
11. Zhang Y, Yao F, Yao X, Yi C, Tan C, Wei L, et al. Role of CCL5 in invasion, proliferation and proportion of CD44+/CD24− phenotype of MCF-7 cells and correlation of CCL5 and CCR5 expression with breast cancer progression. Oncol Rep 2009; 21: 1113-21. Medline
12. Jiao X, Katiyar S, Willmarth N E, Liu M, Ma X, Flomenberg N, et al. c-Jun induces mammary epithelial cellular invasion and breast cancer stem cell expansion. J Biol Chem 2010; 285: 8218-26.
13. Karnoub A E, Dash A B, Vo A P, Sullivan A, Brooks M W, Bell G W, et al. Mesenchymal stem cells within tumour stroma promote breast cancer metastasis. Nature 2007; 449: 557-63.
14. Locati M, Deuschle U, Massardi M L, Martinez F O, Sironi M, Sozzani S, et al. Analysis of the gene expression profile activated by the CC chemokine ligand 5/RANTES and by lipopolysaccharide in human monocytes. J Immunol 2002; 168: 3557-62.
15. Robinson S C, Scott K A, Balkwill F R. Chemokine stimulation of monocyte matrix metalloproteinase-9 requires endogenous TNF-alpha. Eur J Immunol 2002; 32: 404-12.
16. Robinson S C, Scott K A, Wilson J L, Thompson R G, Proudfoot A E, Balkwill F R. A chemokine receptor antagonist inhibits experimental breast tumor growth. Cancer Res 2003; 63: 8360-5.
17. Manes S, Mira E, Colomer R, Montero S, Real L M, Gomez-Mouton C, et al. CCR5 expression influences the progression of human breast cancer in a p53-dependent manner. J Exp Med 2003; 198: 1381-9.
18. Murooka T T, Rahbar R, Fish E N. CCL5 promotes proliferation of MCF-7 cells through mTOR-dependent mRNA translation. Biochem Biophys Res Commun 2009; 387: 381-6.
19. Stormes K A, Lemken C A, Lepre J V, Marinucci M N, Kurt R A. Inhibition of metastasis by inhibition of tumor-derived CCL5. Breast Cancer Res Treat 2005; 89: 209-12.
20. Jayasinghe M M, Golden J M, Nair P, O'Donnell C M, Werner M T, Kurt R A. Tumor-derived CCL5 does not contribute to breast cancer progression. Breast Cancer Res Treat 2008; 111: 511-21.
21. Ertel A, Dean J L, Rui H, Liu C, Witkiewicz A K, Knudsen K E, et al. RB-pathway disruption in breast cancer: differential association with disease subtypes, disease-specific prognosis and therapeutic response. Cell Cycle 2010; 9: 4153-63.
22. Wilkin T J, Su Z, Krambrink A, Long J, Greaves W, Gross R, et al. Three-year safety and efficacy of vicriviroc, a CCR5 antagonist, in HIV-1-infected treatment-experienced patients. J Acquir Immune Defic Syndr 2010; 54: 470-6.
23. Barrett T, Troup D B, Wilhite S E, Ledoux P, Rudnev D, Evangelista C, et al. NCBI GEO: mining tens of millions of expression profiles-database and tools update. Nucleic Acids Res 2007; 35: D760-5.
24. Brazma A, Parkinson H, Sarkans U, Shojatalab M, Vilo J, Abeygunawardena N, et al. ArrayExpress-a public repository for microarray gene expression data at the EBI. Nucleic Acids Res 2003; 31: 68-71.
25. Hu Z, Fan C, Oh D S, Marron J S, He X, Qaqish B F, et al. The molecular portraits of breast tumors are conserved across microarray platforms. BMC Genomics 2006; 7: 96.
26. Liu M, Casimiro M C, Wang C, Shirley L A, Jiao X, Katiyar S, et al. p21CIP1 attenuates Ras- and c-Myc-dependent breast tumor epithelial mesenchymal transition and cancer stem cell-like gene expression in vivo. Proc Natl Acad Sci USA 2009; 106: 19035-9.
27. Nguyen D H, Taub D. Cholesterol is essential for macrophage inflammatory protein 1 beta binding and conformational integrity of CC chemokine receptor 5. Blood 2002; 99: 4298-306.
28. Janowski E, Jiao X, Katiyar S, Lisanti M P, Liu M, Pestell R G, et al. c-Jun is required for TGF-beta-mediated cellular migration via nuclear Ca(2) signaling. Int J Biochem Cell Biol 2011; 43: 1104-13.
29. Velasco-Velazquez M A, Agramonte-Hevia J, Barrera D, Jimenez-Orozco A, Garcia-Mondragon M J, Mendoza-Patino N, et al. 4-Hydroxycoumarin disorganizes the actin cytoskeleton in B16-F10 melanoma cells but not in B82 fibroblasts, decreasing their adhesion to extracellular matrix proteins and motility. Cancer Lett 2003; 198: 179-86.
30. Liu H, Patel M R, Prescher J A, Patsialou A, Qian D, Lin J, et al. Cancer stem cells from human breast tumors are involved in spontaneous metastases in orthotopic mouse models. Proc Natl Acad Sci USA 2010; 107: 18115-20.
31. Zahler M H, Irani A, Malhi H, Reutens A T, Albanese C, Bouzahzah B, et al. The application of a lentiviral vector for gene transfer in fetal human hepatocytes. J Gene Med 2000; 2: 186-93.
32. Walker D K, Abel S, Comby P, Muirhead G J, Nedderman A N, Smith D A. Species differences in the disposition of the CCR5 antagonist, UK-427,857, a new potential treatment for HIV. Drug Metab Dispos 2005; 33: 587-95.
33. Wu K, Katiyar S, Li A, Liu M, Ju X, Popov V M, et al. Dachshund inhibits oncogene-induced breast cancer cellular migration and invasion through suppression of interleukin-8. Proc Natl Acad Sci USA 2008; 105: 6924-9.
34. Charafe-Jauffret E, Ginestier C, Monville F, Finetti P, Adelaide J, Cervera N, et al. Gene expression profiling of breast cell lines identifies potential new basal markers. Oncogene 2006; 25: 2273-84.
35. Riaz M, Elstrodt F, Hollestelle A, Dehghan A, Klijn J G, Schutte M. Low-risk susceptibility alleles in 40 human breast cancer cell lines. BMC Cancer 2009; 9: 236.
36. Hollestelle A, Nagel J H, Smid M, Lam S, Elstrodt F, Wasielewski M, et al. Distinct gene mutation profiles among luminal-type and basal-type breast cancer cell lines. Breast Cancer Res Treat 2010; 121: 53-64.
37. Kao J, Salari K, Bocanegra M, Choi Y L, Girard L, Gandhi J, et al. Molecular profiling of breast cancer cell lines defines relevant tumor models and provides a resource for cancer gene discovery. PLoS ONE 2009; 4: e6146.
38. Mueller A, Mahmoud N G, Goedecke M C, McKeating J A, Strange P G. Pharmacological characterization of the chemokine receptor, CCR5. Br J Pharmacol 2002; 135: 1033-43.
39. Petkovic V, Moghini C, Paoletti S, Uguccioni M, Gerber B. I-TAC/CXCL11 is a natural antagonist for CCR5. J Leukoc Biol 2004; 76: 701-8.
40. Miyashita M, Smith M W, Willey J C, Lechner J F, Trump B F, Harris C C. Effects of serum, transforming growth factor type beta, or 12-O-tetradecanoyl-phorbol- 13-acetate on ionized cytosolic calcium concentration in normal and transformed human bronchial epithelial cells. Cancer Res 1989; 49:63-7.
41. Prescher J A, Contag C H. Guided by the light: visualizing biomolecular processes in living animals with bioluminescence. Curr Opin Chem Biol 2010; 14: 80-9.
42. Yaal-Hahoshen N, Shina S, Leider-Trejo L, Barnea I, Shabtai E L, Azenshtein E, et al. The chemokine CCL5 as a potential prognostic factor predicting disease progression in stage II breast cancer patients. Clin Cancer Res 2006; 12: 4474-80.
43. Shideman C R, Hu S, Peterson P K, Thayer S A. CCL5 evokes calcium signals in microglia through a kinase-, phosphoinositide-, and nucleotide-dependent mechanism. J Neurosci Res 2006; 83:1471-84.
44. Dorr P, Westby M, Dobbs S, Griffin P, Irvine B, Macartney M, et al. Maraviroc (UK-427,857), a potent, orally bioavailable, and selective small-molecule inhibitor of chemokine receptor CCR5 with broad-spectrum anti-human immunodeficiency virus type 1 activity. Antimicrob Agents Chemother 2005; 49: 4721-32.
45. Strizki J M, Tremblay C, Xu S, Wojcik L, Wagner N, Gonsiorek W, et al. Discovery and characterization of vicriviroc (SCH 417690), a CCR5 antagonist with potent activity against human immunodeficiency virus type 1. Antimicrob Agents Chemother 2005; 49: 4911-9.
46. Isik N, Hereld D, Jin T. Fluorescence resonance energy transfer imaging reveals that chemokine-binding modulates heterodimers of CXCR4 and CCR5 receptors. PLoS ONE 2008; 3: e3424.
47. Mira E, Lacalle R A, Gonzalez M A, Gomez-Mouton C, Abad J L, Bernad A, et al. A role for chemokine receptor transactivation in growth factor signaling. EMBO Rep 2001; 2: 151-6.
48. Thirkill T L, Lowe K, Vedagiri H, Blankenship T N, Barakat A I, Douglas G C. Macaque trophoblast migration is regulated by RANTES. Exp Cell Res 2005; 305: 355-64.
49. Abel S, van der Ryst E, Rosario M C, Ridgway C E, Medhurst C G, Taylor-Worth R J, et al. Assessment of the pharmacokinetics, safety and tolerability of maraviroc, a novel CCR5 antagonist, in healthy volunteers. Br J Clin Pharmacol 2008; 65 Suppl 1: 5-18.
50. Vaday G G, Peehl D M, Kadam P A, Lawrence D M. Expression of CCL5 (RANTES) and CCR5 in prostate cancer. Prostate 2006; 66: 124-34.
51. Perret G Y, Crepin M. New pharmacological strategies against metastatic spread. Fundam Clin Pharmacol 2008; 22: 465-92.
52. Sugasawa H, Ichikura T, Tsujimoto H, Kinoshita M, Morita D, Ono S, et al. Prognostic significance of expression of CCL5/RANTES receptors in patients with gastric cancer. J Surg Oncol 2008; 97: 445-50.

The invention claimed is:

1. A method of treating a subject who has or is at risk for metastasis of a basal breast cancer, the method comprising:
   a) providing a tumor sample from the subject;
   b) measuring the level of expression of CCR5 in the sample, wherein the measuring is performed by i) an RNA-based assay selected from the group consisting reverse transcription polymerase chain reaction or a microarray assay; or ii) an immunoassay selected from the group consisting of immunohistochemical staining or fluorescence activated cell sorting;
   c) comparing the expression level of CCR5 in the tumor sample with the expression level of CCR5 in a control sample;
   d) detecting an elevated expression level of CCR5 in the tumor sample as compared to the expression level of CCR5 in a control sample; and
   e) administering a small-molecule CCR5 antagonist to the subject with elevated expression level of CCR5 in the tumor sample when compared to the expression level of CCR5 in a control sample, wherein said CCR5 antagonist is selected from the group consisting of 4,4-difluoro-N-[(1 S)-3-[(1R,5S)-3-(3-methyl-5-propan-2-yl-1,2,4-triazol-4-yl)-8-azabicyclo[3.2.1]octan-8-yl]-1-phenylpropyl]cyclohexane-1-carboxamide ("Maraviroc") and (4,6-dimethylpyrimidin-5-yl)-[4-[(3S)-4-[(1R)-2-methoxy-1-[4-(trifluoromethyl)phenyl]ethyl]-3-methylpiperazin-1-yl]-4-methylbiberidin-1-yl]methanone ("Vicriviroc").

2. The method of claim 1, wherein the CCR5 antagonist blocks metastasis of the cancer.

3. The method of claim 1, wherein the CCR5 antagonist is administered to the subject in addition to a primary, main or initial treatment for the cancer.

4. The method of claim 2, wherein the metastasis is a tumor metastasis in one or more organs selected from the group consisting of liver, brain, bladder, lung, adrenal gland, kidney, and bone.

5. The method of claim 1, wherein the CCR5 antagonist is administered concomitantly or concurrently with other therapies for cancer.

6. The method of claim 1, wherein the CCR5 antagonist is administered concurrently with other adjuvant therapies or following other adjuvant therapies.

7. The method of claim 1, wherein the CCR5 receptor antagonist improves prognosis in the subject having cancer.

8. The method of claim 1, wherein the CCR5 receptor antagonist improves therapeutic effect of the concomitantly or concurrently administered cancer therapy by blocking metastasis of the cancer being treated, thereby contributing to improving clinical outcome of the cancer therapy.

9. A method of treating a subject having basal breast cancer, the method comprising:
administering to the subject having basal breast cancer a therapeutically effective amount of a synthetic small molecule CCR5 antagonist, thereby treating or managing cancer metastasis, wherein the CCR5 antagonist is selected from the group consisting of 4,4-difluoro-N-[(1S)-3-[(1R,5S)-3-(3-methyl-5-propan-2-yl-1,2,4-triazol-4-yl)-8-azabicyclo[3.2.1]octan-8-yl]-1-phenylpropyl]cyclohexane-1-carboxamide ("Maraviroc") or a pharmaceutically acceptable salt thereof and (4,6-dimethylpyrimidin-5-yl)-[4-[(3 S)-4-[(1R)-2-methoxy-1-[4-(trifluoromethyl)phenyl]ethyl]-3-methylpiperazin-1-yl]-4-methylpiperidin-1-yl]methanone ("Vicriviroc") or a pharmaceutically acceptable salt thereof.

10. The method of claim 9, wherein the tumor metastasis comprises a tumor metastasis in one or more organs selected from the group consisting of liver, brain, bladder, lung, adrenal gland, kidney, bone, skin or pancreas and kidney.

11. The method of claim 9, further comprising administering a conventional cancer treatment.

12. The method of claim 11, wherein the conventional cancer treatment is chemotherapy, hormonal therapy, radiation therapy or surgery.

13. The method of claim 9, wherein the CCR5 antagonist is administered until the metastatic burden is reduced.

14. The method of claim 1, wherein the tumor sample comprises a tumor cell in the circulatory or lymphatic system.

* * * * *